United States Patent
Green et al.

(10) Patent No.: US 12,365,900 B2
(45) Date of Patent: Jul. 22, 2025

(54) MIRNA SWITCHES FOR RNA-TRIGGERED CONTROL OF RNA INTERFERENCE

(71) Applicants: TRUSTEES OF BOSTON UNIVERSITY, Boston, MA (US); UNIVERSITY OF FLORIDA RESEARCH FOUNDATION, INCORPORATED, Gainsville, FL (US)

(72) Inventors: Alexander Arthur Green, Chestnut Hill, MA (US); Yu Zhou, Gainesville, FL (US); Peike Sheng, Gainesville, FL (US); Mingyi Xie, Gainesville, FL (US)

(73) Assignees: TRUSTEES OF BOSTON UNIVERSITY, Boston, MA (US); UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 18/393,408

(22) Filed: Dec. 21, 2023

(65) Prior Publication Data
US 2024/0247261 A1    Jul. 25, 2024

Related U.S. Application Data

(60) Provisional application No. 63/434,292, filed on Dec. 21, 2022.

(51) Int. Cl.
| | |
|---|---|
| C12N 15/113 | (2010.01) |
| C12N 9/22 | (2006.01) |
| C12N 15/11 | (2006.01) |

(52) U.S. Cl.
CPC .............. *C12N 15/113* (2013.01); *C12N 9/22* (2013.01); *C12N 15/11* (2013.01); *C12N 2310/141* (2013.01); *C12N 2310/20* (2017.05); *C12N 2310/531* (2013.01); *C12N 2320/32* (2013.01); *C12N 2320/50* (2013.01)

(58) Field of Classification Search
CPC ........ C12N 15/113; C12N 9/22; C12N 15/11; C12N 2310/141; C12N 2310/20; C12N 2310/531; C12N 2320/32; C12N 2320/50
See application file for complete search history.

(56) References Cited

U.S. PATENT DOCUMENTS

| | | |
|---|---|---|
| 9,518,263 B2 | 12/2016 | Han et al. |
| 9,550,987 B2 | 1/2017 | Green et al. |
| 10,550,440 B2 | 2/2020 | Green et al. |
| 11,773,430 B2 | 10/2023 | Green et al. |
| 11,802,318 B2 | 10/2023 | Green et al. |
| 2006/0178327 A1 | 8/2006 | Yeung |
| 2006/0252722 A1 | 11/2006 | Lollo et al. |
| 2021/0095286 A1* | 4/2021 | Weiss ................... C12N 15/111 |
| 2022/0170116 A1 | 6/2022 | Green et al. |

FOREIGN PATENT DOCUMENTS

WO    2021062096 A1    4/2021

OTHER PUBLICATIONS

Treiber, T., Treiber, N. & Meister, G. Regulation of microRNA biogenesis and its crosstalk with other cellular pathways. Nat Rev Mol Cell Biol 20, 5-20 (2019). https://doi.org/10.1038/s41580-018-0059-1 (Year: 2019).*
Combinatorially Inducible RNA Interference Triggered by Chemically Modified Oligonucleotides Deepak Kumar, Sang Hoon Kim, and Yohei Yokobayashi Journal of the American Chemical Society 2011 133 (8), 2783-2788 DOI: 10.1021/ja1107436 (Year: 2011).*
Gao Z, Herrera-Carrillo E, Berkhout B. Delineation of the Exact Transcription Termination Signal for Type 3 Polymerase III. Mol Ther Nucleic Acids. Mar. 2, 2018;10:36-44. doi: 10.1016/j.omtn.2017.11.006. Epub Nov. 21, 2017. PMID: 29499947; PMCID: PMC5725217. (Year: 2017).*
Svoboda P, Di Cara A (2006) Hairpin RNA: a secondary structure of primary importance. Cell Mol Life Sci 63(7-8):901-908 (Year: 2006).*
Zhang, Q., Ma, D., Wu, F. et al. Predictable control of RNA lifetime using engineered degradation-tuning RNAs. Nat Chem Biol 17, 828-836 (2021). (Year: 2021).*
Hwang, Y., Kim, S.G., Jang, S et al. Signal amplification and optimization of riboswitch-based hybrid inputs by modular and titratable toehold switches. J Biol Eng 15, 11 (2021). (Year: 2021).*

(Continued)

*Primary Examiner* — Richard A Schnizer
*Assistant Examiner* — Amanda M Zahorik
(74) *Attorney, Agent, or Firm* — MARSHALL, GERSTEIN & BORUN LLP

(57) ABSTRACT

Provided herein are methods, compositions and systems comprising synthetic nucleic acid molecules that enable inducible or conditional pri-miRNA processing, preferably in mammalian cells in vivo. Provided herein are synthetic nucleic acid molecules referred to as Orthogonal RNA Interference induced by Trigger RNA (ORIENTR) that switches between an inactive form and an active form upon interaction with one or more specific RNA-trigger molecules, which can be e.g., a synthetic RNA-trigger, or a disease-specific RNA signals, such as disease-specific mRNA, miRNA, or other cellular RNA products with sequences that characterize a disease state of a cell. The interaction between the RNA-trigger molecules and the ORIENTR is preferably mediated by hybridization, which exposes, facilitates the formation, and/or allows the formation of a correctly folded pri-miRNA scaffold substrate that can be processed by proteins of the RNAi pathway (such as Dicer), leading to RNAi-mediated repression of a target gene. Also provided herein are methods of using such ORIENTR molecules for the treatment or prevention of a disease in a subject, as well as detecting the presence or absence of a target RNA in a biological sample or in vivo.

26 Claims, 28 Drawing Sheets

Specification includes a Sequence Listing.

(56) References Cited

OTHER PUBLICATIONS

An et al. Trinh, V. B. & Yokobayashi, Y. Artificial control of gene expression in mammalian cells by modulating RNA interference through aptamer-small molecule interaction. RNA 12, 710-716 (2006).
Beisel et al. Design of small molecule-responsive microRNAs based on structural requirements for Drosha processing. Nucleic Acids Res 39, 2981-2994 (2011).
Borel et al. Recombinant AAV as a Platform for Translating the Therapeutic Potential of RNA Interference. Molecular Therapy 22, 692 (2014).
Chandran et al. Inducible and reversible phenotypes in a novel mouse model of Friedreich's Ataxia. Elife 6, e30054 (2017).
Fu et al. Recent progress in microRNA-based delivery systems for the treatment of human disease. ExRNA 1, 1-14 (2019).
Green et al. Toehold Switches: De-Novo-Designed Regulators of Gene Expression. Cell 159, 925-939 (2014).
Griffiths-Jones et al. miRBase: microRNA sequences, targets and gene nomenclature. Nucleic Acids Res 34, D140-D144 (2006).
Grimm et al. Fatality in mice due to oversaturation of cellular microRNA/short hairpin RNA pathways. Nature 441, 537-541 (2006).
Grimm The dose can make the poison: lessons learned from adverse in vivo toxicities caused by RNAi overexpression. Silence 2, 1-6 (2011).
Gruber et al. The Vienna RNA Websuite. Nucleic Acids Res 36, w70-w74 (2008).
Ha et al. Regulation of microRNA biogenesis. Nature Reviews Molecular Cell Biology vol. 15, 509-524 (2014).
Harper. Progress and Challenges in RNA Interference Therapy for Huntington Disease. Arch Neurol 66, 933-938 (2009).
Hennig et al. Selective inhibition of miRNA processing by a herpesvirus-encoded miRNA. Nature 605, 539-544 (2022).
Hochrein et al. Signal Transduction in Human Cell Lysate via Dynamic RNA Nanotechnology. ACS Synth Biol 7, 2796-2802 (2018).
Hochrein et al. Conditional Dicer Substrate Formation via Shape and Sequence Transduction with Small Conditional RNAs. J Am Chem Soc 135, 17322-17330 (2013).
Hocquemiller et al. Adeno-Associated Virus-Based Gene Therapy for CNS Diseases. Hum Gene Ther 27, 478 (2016).
Jiang et al. Programmable eukaryotic protein synthesis with RNA sensors by harnessing ADAR. Nat Biotechnol 41, 698-707 (2022).
Jin et al. Structural Basis for pri-miRNA Recognition by Drosha. Mol Cell 78, 423-433.e5 (2020).
Kaseniit et al. Modular, programmable RNA sensing using ADAR editing in living cells. Nat Biotechnol 41, 482-487 (2022).
Kim et al. De novo-designed translation-repressing riboregulators for multi-input cellular logic. Nat Chem Biol 15, 1173-1182 (2019).
Kim et al. A quantitative map of human primary microRNA processing sites. Mol Cell 81, 3422-3439 (2021).
Kumar et al. Conditional RNA Interference Mediated by Allosteric Ribozyme. J Am Chem Soc 131, 13906-13907 (2009).
Macrae et al. Structural basis for double-stranded RNA processing by Dicer. Science (1979) 311, 195-198 (2006).
Macrae et al. A. Structural determinants of RNA recognition and cleavage by Dicer. Nat Struct Mol Biol 14, 934-940 (2007).
Mcjunkin et al. Reversible suppression of an essential gene in adult mice using transgenic RNA interference. Proc Natl Acad Sci USA 108, 7113-7118 (2011).
Miller et al. Near-infrared fluorescent northern blot. RNA 24, 1871-1877 (2018).
Nguyen et al. Functional Anatomy of the Human Microprocessor. Cell 161, 1374-1387 (2015).
Oesinghaus et al. Controlling Gene Expression in Mammalian Cells Using Multiplexed Conditional Guide RNAs for Cas12a**. Angew. Chem. Int. Ed 60, 23894-23902 (2021).
Qian et al. Programmable RNA sensing for cell monitoring and manipulation. Nature 610, 713 (2022).
Rao et al. Tissue-specific and cell type-specific RNA interference in vivo. Nat Protoc 1, 1494-1501 (2006).
Setten et al. The current state and future directions of RNAi-based therapeutics. Nature Reviews Drug Discovery 2019 18:6 18, 421-446 (2019).
Tatiparti et al. siRNA Delivery Strategies: A Comprehensive Review of Recent Developments. Nanomaterials 7, 77 (2017).
Wang et al. Efficient and Precise Processing of the Optimized Primary Artificial MicroRNA in a Huntingtin-Lowering Adeno-Associated Viral Gene Therapy in Vitro and in Mice and Nonhuman Primates. Hum Gene Ther 33, 37-60 (2022).
Wiznerowicz et al. Tuning silence: conditional systems for RNA interference. Nat Methods 3, 682-688 (2006).
Xie et al. The host Integrator complex acts in transcription-independent maturation of herpesvirus microRNA 3' ends. Genes Dev 29, 1552-1564 (2015).
Yan et al. Cas13d Is a Compact RNA-Targeting Type VI CRISPR Effector Positively Modulated by a WYL-Domain- Containing Accessory Protein. Mol Cell 70, 327-339.e5 (2018).
Yan et al. Rapid and Multiplexed Nucleic Acid Detection using Programmable Aptamer-Based RNA Switches. medRxiv preprint (2023) doi: 10.1101/2023.06.02.23290873.
Zadeh et al. NUPACK: Analysis and design of nucleic acid systems. J Comput Chem 32, 170-173 (2011).

* cited by examiner

| ORIENTR component | INACTIVE ORIENTR configuration 5' → 3'(ORIENTR-OFF) | Structure/domain configuration of INACTIVE ORIENTR | ACTIVE ORIENTR configuration (ORIENTR-ON): in a COMPLEX with RNA-TRIGGER 5' → 3' | 2nd Structures/domains of ACTIVE ORIENTR in complex with RNA-TRIGGER molecule |
|---|---|---|---|---|
| ORIENTR molecule; RNA-trigger molecule | See FIG. 5A and FIG. 1C for configuration of the ORIENTR in the ORIENTR-OFF state. See FIG. 5B for conformation of RNA-trigger | ORIENTR Secondary Structures (INACTIVE): (1)Toehold domain (2) sequestering-loop domain, and (3) output domain, optionally: (4) leak-reduction domain ⬇ Output domain is not accessible and/or not able to be processed by Microprocessor so output miR not produced. ⬇ NO RNAi of target | See FIG. 5C and FIG. 1C for configuration of ORIENTR-RNA trigger complex (ORIENTR-ON state) | ORIENTR Secondary Structures (ACTIVE): (1) sensing domain (2) reconfiguration domain, (3) output domain ⬇ the reconfiguration domain and the output domain together, form a pri-miRNA scaffold that can be recognized by Microprocessor to process the pri-miRNA to pre-miRNA ⬇ RNAi can occur |
| 3' GGG (optional) | Single stranded | | Single stranded | |

*FIG. 9*

| 5' Toehold region | 16nt single stranded RNA | Part of RNA-trigger sensing domain | 5' toehold forms d.s. duplex with cognate RNA sequence of trigger | Forms SENSING DOMAIN |
|---|---|---|---|---|
| 3' sequestering arm | forms duplex with 3' flanking sequence forming the base of the *sequestering-loop domain* | | 3' sequestering arm forms d.s. duplex with 5' portion of cognate RNA sequence of trigger → Sequestering-loop domain is dismantled | |
| d.s. Hairpin loop (optional) | d.s. hairpin loop at top of the *sequestering-loop domain* | | d.s. Hairpin loop (optional) | Located between sensing domain and reconfiguration domain |
| 3' flanking sequence | forms d.s. RNA duplex with 3' sequestering arm, forming the base of the *sequestering-loop domain* | Each are part of Sequestering-loop domain on INACTIVE-ORIENTR | Exists as single stranded sequence and is no longer as part of the sequestering hairpin loop; | is s.s. RNA located between hairpin loop and reconfiguration domain |
| 5' basal stem | forms d.s. RNA duplex with a 5' portion with the 3' sequestering arm | | Forms d.s. duplex with 3' basal step to form the RECONFIGURATION domain | |

FIG. 9 (cont.)

| | | | | |
|---|---|---|---|---|
| Guide strand | forms d.s. RNA duplex with the passenger strand | forms OUTPUT domain, but cannot be recognized by Microprocessor | OUTPUT domain is NOW able to be recognized by Microprocessor due to presence of basal stem RECONFIGURATION domain | Together the RECONFIGURATION domain and the OUTPUT domain form a Pri-miRNA scaffold that can be recognized by Microprocessor |
| Apical loop sequence | | | | |
| Passenger strand | forms d.s. RNA duplex with the Guide strand | | | |
| 3' basal stem | Single stranded OR: forms part of the d.s. stem of leak-reduction motif | | Forms d.s. duplex with 5' basal stem to form the RECONFIGURATION domain (if d.s. leak-reduction motif was present, 5' basal stem is released from hairpin) | |
| Optional: Leak-reduction motif | If present, forms part of d.s. duplex with 3' basal stem | Leak-reduction motif | If present, releases 3' basal stem strand and exists as single stranded | Single stranded (leak-reduction hairpin disassembled) |
| Spacer sequence | Single stranded | n/a | Single stranded | n/a |
| 3' Pol III terminal | Single stranded | n/a | Single stranded | n/a |

FIG. 9 (cont.)

SEQUENCE LISTING

```
Sequence total quantity: 97
SEQ ID NO: 1           moltype = RNA  length = 11
FEATURE                Location/Qualifiers
source                 1..11
                       mol_type = other RNA
                       organism = synthetic construct
SEQUENCE: 1
cttgttccac t                                                          11

SEQ ID NO: 2           moltype = RNA  length = 11
FEATURE                Location/Qualifiers
source                 1..11
                       mol_type = other RNA
                       organism = synthetic construct
SEQUENCE: 2
agtgtgacag g                                                          11

SEQ ID NO: 3           moltype = RNA  length = 11
FEATURE                Location/Qualifiers
source                 1..11
                       mol_type = other RNA
                       organism = synthetic construct
SEQUENCE: 3
agccataact c                                                          11

SEQ ID NO: 4           moltype = RNA  length = 11
FEATURE                Location/Qualifiers
source                 1..11
                       mol_type = other RNA
                       organism = synthetic construct
SEQUENCE: 4
gagtcatggc t                                                          11
```

-continued

```
SEQ ID NO: 5            moltype = RNA   length = 33
FEATURE                 Location/Qualifiers
source                  1..33
                        mol_type = other RNA
                        organism = synthetic construct
SEQUENCE: 5
ggaaacccct accaactggt cggggtttga aac                                33

SEQ ID NO: 6            moltype = DNA   length = 33
FEATURE                 Location/Qualifiers
source                  1..33
                        mol_type = other DNA
                        organism = synthetic construct
SEQUENCE: 6
ggaaacccct accaactggt cggggtttga aac                                33

SEQ ID NO: 7            moltype = RNA   length = 22
FEATURE                 Location/Qualifiers
source                  1..22
                        mol_type = other RNA
                        organism = synthetic construct
SEQUENCE: 7
accgtgttgc tacagctata ag                                            22

SEQ ID NO: 8            moltype = RNA   length = 19
FEATURE                 Location/Qualifiers
source                  1..19
                        mol_type = other RNA
                        organism = synthetic construct
SEQUENCE: 8
tagtgaaata tatattaaa                                                19

SEQ ID NO: 9            moltype = RNA   length = 22
FEATURE                 Location/Qualifiers
source                  1..22
                        mol_type = other RNA
                        organism = synthetic construct
SEQUENCE: 9
catatagctg atgcaacacg ga                                            22

SEQ ID NO: 10           moltype = RNA   length = 29
FEATURE                 Location/Qualifiers
source                  1..29
                        mol_type = other RNA
                        organism = synthetic construct
SEQUENCE: 10
nnnnnnnnnn nngatacagc aactttttt                                     29

SEQ ID NO: 11           moltype =   length =
SEQUENCE: 11
000

SEQ ID NO: 12           moltype = RNA   length = 114
FEATURE                 Location/Qualifiers
source                  1..114
                        mol_type = other RNA
                        organism = synthetic construct
SEQUENCE: 12
gaactgacat acttgttcca ctcaccgtgt tgctcagcta taagtagtga aatatatatt   60
aaacatatag ctgatgcaac acggatagtg tgacagggat acagcaactt tttt        114

SEQ ID NO: 13           moltype = DNA   length = 154
FEATURE                 Location/Qualifiers
source                  1..154
                        mol_type = other DNA
                        organism = synthetic construct
SEQUENCE: 13
gcgctaatac gactcactat agggataaac atacatgcgc aactgacata cttgttccac   60
tctagcagca cgtaaatatt ggcgtagtga aatatatatt aaacaccaat attactgtgc  120
tgctttagtg tgacagggat acagcaactt tttt                              154

SEQ ID NO: 14           moltype = DNA   length = 154
FEATURE                 Location/Qualifiers
source                  1..154
                        mol_type = other DNA
                        organism = synthetic construct
SEQUENCE: 14
gcgctaatac gactcactat agggataaac atacatgcgc aactgacata cttgttccac   60
tcaccgtgtt gctacagcta taagtagtga aatatatatt aaacatatag ctgatgcaac  120
```

```
acggatagtg tgacagggat acagcaactt tttt                               154

SEQ ID NO: 15              moltype = DNA   length = 164
FEATURE                    Location/Qualifiers
source                     1..164
                           mol_type = other DNA
                           organism = synthetic construct
SEQUENCE: 15
ggtcagttcg cgctaatacg actcactata gggataaaca tacatgcgcg aactgacata   60
cttgttccac tcaccgtgtt gctacagcta taagtagtga aatatatatt aaacatatag   120
ctgatgcaac acggatagtg tgacagggat acagcaactt tttt                   164

SEQ ID NO: 16              moltype = DNA   length = 155
FEATURE                    Location/Qualifiers
source                     1..155
                           mol_type = other DNA
                           organism = synthetic construct
SEQUENCE: 16
gcgctaatac gactcactat agggataaac atacatgcgc cctcaacgat acttgttcca   60
ctcaccgtgt tgctacagct ataagtagtg aaatatatat taaacatata gctgatgcaa   120
cacgatagt gtgacaggga tacagcaact ttttt                              155

SEQ ID NO: 17              moltype = DNA   length = 164
FEATURE                    Location/Qualifiers
source                     1..164
                           mol_type = other DNA
                           organism = synthetic construct
SEQUENCE: 17
gcgttgaggg cgctaatacg actcactata gggataaaca tacatgcgcc ctcaacgata   60
cttgttccac tcaccgtgtt gctacagcta taagtagtga aatatatatt aaacatatag   120
ctgatgcaac acggatagtg tgacagggat acagcaactt tttt                   164

SEQ ID NO: 18              moltype = DNA   length = 155
FEATURE                    Location/Qualifiers
source                     1..155
                           mol_type = other DNA
                           organism = synthetic construct
SEQUENCE: 18
gcgctaatac gactcactat agggataaac atacatgcgc aactgacata agccataact   60
ccaccgtgtt gctacagcta taagtagtga aatatatatt aaacatatag ctgatgcaac   120
acggatagtg tgacagggat acagcaactt ttttt                             155

SEQ ID NO: 19              moltype = DNA   length = 155
FEATURE                    Location/Qualifiers
source                     1..155
                           mol_type = other DNA
                           organism = synthetic construct
SEQUENCE: 19
gcgctaatac gactcactat agggataaac atacatgcgc aactgacata cttgttccac   60
tcaccgtgtt gctacagcta taagtagtga aatatatatt aaacatatag ctgatgcaac   120
acggatgagt catggctgat acagcaactt ttttt                             155

SEQ ID NO: 20              moltype = DNA   length = 155
FEATURE                    Location/Qualifiers
source                     1..155
                           mol_type = other DNA
                           organism = synthetic construct
SEQUENCE: 20
gcgctaatac gactcactat agggataaac atacatgcgc aactgacata agccataact   60
ccaccgtgtt gctacagcta taagtagtga aatatatatt aaacatatag ctgatgcaac   120
acggatgagt catggctgat acagcaactt ttttt                             155

SEQ ID NO: 21              moltype = DNA   length = 186
FEATURE                    Location/Qualifiers
source                     1..186
                           mol_type = other DNA
                           organism = synthetic construct
SEQUENCE: 21
gggtgaaatg aaatgaaagc agagtgacaa tagaggtaag acgcagtatc tgtatcccga   60
cagatactgc aacttacctc cattgtcact ctgcaccgtg ttgctacagc tataagtagt   120
gaaatatata ttaaacatat agctgatgca acacggaaca gaatgacaag atacagcaac   180
tttttt                                                             186

SEQ ID NO: 22              moltype = DNA   length = 186
FEATURE                    Location/Qualifiers
source                     1..186
                           mol_type = other DNA
                           organism = synthetic construct
SEQUENCE: 22
```

```
gggtgagatg gatgtgattg ataggtaaga ttgtattgct cctcgccgac gcctccatct   60
gcgtcggcga caagcaatac tatcttacct atcaaccgtg ttgctacagc tataagtagt  120
gaaatatata ttaaacatat agctgatgca acacggagga taagtaagag atacagcaac  180
tttttt                                                             186

SEQ ID NO: 23          moltype = DNA   length = 186
FEATURE                Location/Qualifiers
source                 1..186
                       mol_type = other DNA
                       organism = synthetic construct
SEQUENCE: 23
gggtgatgga gtagagaatg tattaggagt tagaattaga ctacgaggct gctgctcgtc   60
gcagcctcgt tttctaattc taactcctaa tacaaccgtg ttgctacagc tataagtagt  120
gaaatatata ttaaacatat agctgatgca acacggaagt atgaggagtg atacagcaac  180
tttttt                                                             186

SEQ ID NO: 24          moltype = DNA   length = 186
FEATURE                Location/Qualifiers
source                 1..186
                       mol_type = other DNA
                       organism = synthetic construct
SEQUENCE: 24
gggtgaataa gaatgaaagt atggaagatg tagtcgtgta acggatatgc aactgcggct   60
ttgcatatcc tatacacgac aacatcttcc ataccgtg ttgctacagc tataagtagt  120
gaaatatata ttaaacatat agctgatgca acacggaata tgcaagatgg atacagcaac  180
tttttt                                                             186

SEQ ID NO: 25          moltype = DNA   length = 186
FEATURE                Location/Qualifiers
source                 1..186
                       mol_type = other DNA
                       organism = synthetic construct
SEQUENCE: 25
gggtcgaatg ttagtgtgcg ctgttgaggt atgtagttga tattccgggc agaaacatga   60
ctgcccggaa cctcaactac ctacctcaac agcgaccgtg ttgctacagc tataagtagt  120
gaaatatata ttaaacatat agctgatgca acacggaagc tggtgaggtg atacagcaac  180
tttttt                                                             186

SEQ ID NO: 26          moltype = DNA   length = 186
FEATURE                Location/Qualifiers
source                 1..186
                       mol_type = other DNA
                       organism = synthetic construct
SEQUENCE: 26
gggtgatgag agtaaatgga cgaaatgtag taagtaatga tatcttccat ccaaatcaaa   60
ggatggaaga cttcattact aactacattt cgtcaccgtg ttgctacagc tataagtagt  120
gaaatatata ttaaacatat agctgatgca acacggacac gacatgtagg atacagcaac  180
tttttt                                                             186

SEQ ID NO: 27          moltype = DNA   length = 186
FEATURE                Location/Qualifiers
source                 1..186
                       mol_type = other DNA
                       organism = synthetic construct
SEQUENCE: 27
gggtcgaatg gtagtaagtt aaggataatg taatgtgtct cacgaggctc tgtggcttac   60
cagagcctcg atagacacat aacattatcc ttaaaccgtg ttgctacagc tataagtagt  120
gaaatatata ttaaacatat agctgatgca acacggaata agaataatgg atacagcaac  180
tttttt                                                             186

SEQ ID NO: 28          moltype = DNA   length = 186
FEATURE                Location/Qualifiers
source                 1..186
                       mol_type = other DNA
                       organism = synthetic construct
SEQUENCE: 28
gggtgaatgg cgtaagtaga tggtaggatg acagttgagt tcgcagtgga aacctactat   60
tttccactgc acactcaact ctcatcctac catcaccgtg ttgctacagc tataagtagt  120
gaaatatata ttaaacatat agctgatgca acacggagat ggcaggatgg atacagcaac  180
tttttt                                                             186

SEQ ID NO: 29          moltype = DNA   length = 186
FEATURE                Location/Qualifiers
source                 1..186
                       mol_type = other DNA
                       organism = synthetic construct
SEQUENCE: 29
gggtcgttag ttattagagg tatgcttaag ttcgtatagt cctcggtctc gaccggatca   60
tcgagaccga ttactatacg cacttaagca taccaccgtg ttgctacagc tataagtagt  120
```

```
gaaatatata ttaaacatat agctgatgca acacggaagt atacttaagg atacagcaac    180
tttttt                                                              186

SEQ ID NO: 30           moltype = DNA   length = 186
FEATURE                 Location/Qualifiers
source                  1..186
                        mol_type = other DNA
                        organism = synthetic construct
SEQUENCE: 30
gggtgagagc atagagacgt gaagatggga taggaagtga catggcgtct ctacgttgta    60
agagacgcca cttcacttcc catcccatct tcacaccgtg ttgctacagc tataagtagt    120
gaaatatata ttaaacatat agctgatgca acacggaatg aacatgggag atacagcaac    180
tttttt                                                              186

SEQ ID NO: 31           moltype = DNA   length = 186
FEATURE                 Location/Qualifiers
source                  1..186
                        mol_type = other DNA
                        organism = synthetic construct
SEQUENCE: 31
gggtgattag ttgaaagata tagaaagcga agtcggtaaa tccgcggtaa gctggtgagg    60
gcttaccgcg tctttaccga attcgctttc tataaccgtg ttgctacagc tataagtagt    120
gaaatatata ttaaacatat agctgatgca acacggacat agcaagcgag atacagcaac    180
tttttt                                                              186

SEQ ID NO: 32           moltype = DNA   length = 186
FEATURE                 Location/Qualifiers
source                  1..186
                        mol_type = other DNA
                        organism = synthetic construct
SEQUENCE: 32
gggtgccctg tcgttctagt atgtagcttg tcgtgttagt gactctacca ctggctgggt    60
agtggtagag cgactaacac tacaagctac atacaccgtg ttgctacagc tataagtagt    120
gaaatatata ttaaacatat agctgatgca acacggatta tgaagcttgg atacagcaac    180
tttttt                                                              186

SEQ ID NO: 33           moltype = DNA   length = 186
FEATURE                 Location/Qualifiers
source                  1..186
                        mol_type = other DNA
                        organism = synthetic construct
SEQUENCE: 33
gggtcattat gttatttcgc taatcaggca cggtgtagtt ccgcatagcc caactttccg    60
tgggctatgc ataactacac agtgcctgat tagcaccgtg ttgctacagc tataagtagt    120
gaaatatata ttaaacatat agctgatgca acacggatct aagcaggcag atacagcaac    180
tttttt                                                              186

SEQ ID NO: 34           moltype = DNA   length = 186
FEATURE                 Location/Qualifiers
source                  1..186
                        mol_type = other DNA
                        organism = synthetic construct
SEQUENCE: 34
gggtgagggc aaattgaggc gcgtttaggc tggttagatt attggctgga aatcagcaca    60
tttccagcca cgaatctaac gagcctaaac gcgcaccgtg ttgctacagc tataagtagt    120
gaaatatata ttaaacatat agctgatgca acacggaacg cggttaggcg atacagcaac    180
tttttt                                                              186

SEQ ID NO: 35           moltype = DNA   length = 186
FEATURE                 Location/Qualifiers
source                  1..186
                        mol_type = other DNA
                        organism = synthetic construct
SEQUENCE: 35
gggtgataat agaataatgg agtaaacgaa tgcgctagaa cccggttact catctgaatg    60
tgagtaaccg acttctagcg aattcgttta ctccaccgtg ttgctacagc tataagtagt    120
gaaatatata ttaaacatat agctgatgca acacggacga gttaacgaag atacagcaac    180
tttttt                                                              186

SEQ ID NO: 36           moltype = DNA   length = 186
FEATURE                 Location/Qualifiers
source                  1..186
                        mol_type = other DNA
                        organism = synthetic construct
SEQUENCE: 36
gggtgccttt agcttgcaat gtcgtttctg ttcgtgttag aacgtgaagc ttgcagaaca    60
aagcttcacg gcctaacacg cacagaaacg acataccgtg ttgctacagc tataagtagt    120
gaaatatata ttaaacatat agctgatgca acacggactg tcatttctgg atacagcaac    180
tttttt                                                              186
```

```
SEQ ID NO: 37           moltype = DNA   length = 186
FEATURE                 Location/Qualifiers
source                  1..186
                        mol_type = other DNA
                        organism = synthetic construct
SEQUENCE: 37
gggtgattag atgacatacc cttaacgaac cgggatttag tcggatggct cgaccggatc    60
cgagccatcc atctaaatcc aggttcgtta agggaccgtg ttgctacagc tataagtagt   120
gaaatatata ttaaacatat agctgatgca acacggaacc tttacgaacg atacagcaac   180
tttttt                                                              186

SEQ ID NO: 38           moltype = DNA   length = 186
FEATURE                 Location/Qualifiers
source                  1..186
                        mol_type = other DNA
                        organism = synthetic construct
SEQUENCE: 38
gggtctctac gccgcttcga atgtttatgt tatcgcttgt aaccagcgct ccgtttaagt    60
ggagcgctgg acacaagcga caacataaac attcaccgtg ttgctacagc tataagtagt   120
gaaatatata ttaaacatat agctgatgca acacggacaa tgattatgtg atacagcaac   180
tttttt                                                              186

SEQ ID NO: 39           moltype = DNA   length = 186
FEATURE                 Location/Qualifiers
source                  1..186
                        mol_type = other DNA
                        organism = synthetic construct
SEQUENCE: 39
gggtcatata ggttaggcag caggtatcac agtgtatctc tgagatgtat agccatagca    60
ctatacatct atgagataca atgtgatacc tgctaccgtg ttgctacagc tataagtagt   120
gaaatatata ttaaacatat agctgatgca acacggatgc agctatcacg atacagcaac   180
tttttt                                                              186

SEQ ID NO: 40           moltype = DNA   length = 71
FEATURE                 Location/Qualifiers
source                  1..71
                        mol_type = other DNA
                        organism = synthetic construct
SEQUENCE: 40
gggcccatag gattttacct atgggaaact tacctctatt gtcactctgc tttcatttca    60
ttcattttt t                                                          71

SEQ ID NO: 41           moltype = DNA   length = 71
FEATURE                 Location/Qualifiers
source                  1..71
                        mol_type = other DNA
                        organism = synthetic construct
SEQUENCE: 41
gggctcgata gcgcagacta tcgagacaag caatacaatc ttacctatca atcacatcca    60
tctcattttt t                                                         71

SEQ ID NO: 42           moltype = DNA   length = 71
FEATURE                 Location/Qualifiers
source                  1..71
                        mol_type = other DNA
                        organism = synthetic construct
SEQUENCE: 42
gggcacgttc cttagttgga acgtgatttc taattctaac tcctaataca ttctctactc    60
catcattttt t                                                         71

SEQ ID NO: 43           moltype = DNA   length = 71
FEATURE                 Location/Qualifiers
source                  1..71
                        mol_type = other DNA
                        organism = synthetic construct
SEQUENCE: 43
gggcctaagt tgagaataac ttaggaatta cacgactaca tcttccatac tttcattctt    60
attcattttt t                                                         71

SEQ ID NO: 44           moltype = DNA   length = 71
FEATURE                 Location/Qualifiers
source                  1..71
                        mol_type = other DNA
                        organism = synthetic construct
SEQUENCE: 44
gggaggtcgt gcaataacac gacctacttc aactacatac ctcaacagcg cacactaaca    60
ttcgattttt t                                                         71
```

```
SEQ ID NO: 45            moltype = DNA   length = 71
FEATURE                  Location/Qualifiers
source                   1..71
                         mol_type = other DNA
                         organism = synthetic construct
SEQUENCE: 45
gggctcagcc agcactgtgg ctgagcgttc attacttact acatttcgtc catttactct     60
catcattttt t                                                          71

SEQ ID NO: 46            moltype = DNA   length = 71
FEATURE                  Location/Qualifiers
source                   1..71
                         mol_type = other DNA
                         organism = synthetic construct
SEQUENCE: 46
gggcgcagtt atttgcttaa ctgcggacag acacattaca ttatccttaa cttactacca     60
ttcgattttt t                                                          71

SEQ ID NO: 47            moltype = DNA   length = 71
FEATURE                  Location/Qualifiers
source                   1..71
                         mol_type = other DNA
                         organism = synthetic construct
SEQUENCE: 47
gggagccatg acccttatca tggctcttac tcaactgtca tcctaccatc tacttacgcc     60
attcattttt t                                                          71

SEQ ID NO: 48            moltype = DNA   length = 71
FEATURE                  Location/Qualifiers
source                   1..71
                         mol_type = other DNA
                         organism = synthetic construct
SEQUENCE: 48
gggccataga tatttcaatc tatggaatac tatacgaact taagcatacc tctaataact     60
aacgattttt t                                                          71

SEQ ID NO: 49            moltype = DNA   length = 71
FEATURE                  Location/Qualifiers
source                   1..71
                         mol_type = other DNA
                         organism = synthetic construct
SEQUENCE: 49
gggcctttgg catccctgcc aaaggcattc acttcctatc ccatcttcac gtctctatgc     60
tctcattttt t                                                          71

SEQ ID NO: 50            moltype = DNA   length = 71
FEATURE                  Location/Qualifiers
source                   1..71
                         mol_type = other DNA
                         organism = synthetic construct
SEQUENCE: 50
gggccaactc ataactatga gttggaactt taccgacttc gctttctata tctttcaact     60
aatcattttt t                                                          71

SEQ ID NO: 51            moltype = DNA   length = 71
FEATURE                  Location/Qualifiers
source                   1..71
                         mol_type = other DNA
                         organism = synthetic construct
SEQUENCE: 51
gggacggcac tgggacaagt gccgtataac taacacgaca agctacatac tagaacgaca     60
gggcattttt t                                                          71

SEQ ID NO: 52            moltype = DNA   length = 71
FEATURE                  Location/Qualifiers
source                   1..71
                         mol_type = other DNA
                         organism = synthetic construct
SEQUENCE: 52
gggagccgac gaccgaccgt cggctaagaa ctacaccgtg cctgattagc gaaataacat     60
aatgattttt t                                                          71

SEQ ID NO: 53            moltype = DNA   length = 71
FEATURE                  Location/Qualifiers
source                   1..71
                         mol_type = other DNA
                         organism = synthetic construct
SEQUENCE: 53
gggacgtctg ctacgctgca gacgtctgaa tctaaccagc ctaaacgcgc tcaatttgc      60
```

```
cctcattttt t                                                          71

SEQ ID NO: 54           moltype = DNA   length = 71
FEATURE                 Location/Qualifiers
source                  1..71
                        mol_type = other DNA
                        organism = synthetic construct
SEQUENCE: 54
gggcaccaga gctgcgcctc tggtgatttt ctagcgcatt cgtttactcc attattctat     60
tatcattttt t                                                          71

SEQ ID NO: 55           moltype = DNA   length = 71
FEATURE                 Location/Qualifiers
source                  1..71
                        mol_type = other DNA
                        organism = synthetic construct
SEQUENCE: 55
gggacctgcg aacgaggtcg caggtaaact aacacgaaca gaaacgacat tgcaagctaa     60
aggcattttt t                                                          71

SEQ ID NO: 56           moltype = DNA   length = 71
FEATURE                 Location/Qualifiers
source                  1..71
                        mol_type = other DNA
                        organism = synthetic construct
SEQUENCE: 56
gggtgccggt cttatgcgac cggcacatct aaatcccggt tcgttaaggg tatgtcatct     60
aatcattttt t                                                          71

SEQ ID NO: 57           moltype = DNA   length = 71
FEATURE                 Location/Qualifiers
source                  1..71
                        mol_type = other DNA
                        organism = synthetic construct
SEQUENCE: 57
gggtgccctc gcggagtcga gggcatgaac aagcgataac ataaacattc gaagcggcgt     60
agagattttt t                                                          71

SEQ ID NO: 58           moltype = DNA   length = 71
FEATURE                 Location/Qualifiers
source                  1..71
                        mol_type = other DNA
                        organism = synthetic construct
SEQUENCE: 58
gggcccttac ctgtttaggt aagggactga gatacactgt gatacctgct gcctaaccta     60
tatgattttt t                                                          71

SEQ ID NO: 59           moltype = DNA   length = 64
FEATURE                 Location/Qualifiers
source                  1..64
                        mol_type = other DNA
                        organism = synthetic construct
SEQUENCE: 59
gggccgtact aaggtgctag tacggcatac taactctacc ttaccttcac ttacttcat     60
tttt                                                                  64

SEQ ID NO: 60           moltype = DNA   length = 161
FEATURE                 Location/Qualifiers
source                  1..161
                        mol_type = other DNA
                        organism = synthetic construct
SEQUENCE: 60
gggtgagatg gatgtgattg ataggtaaga ttgtattgct cctacaagca atactatctt     60
acctatcaac cgtgttgcta cagctataag tagtgaaata tatattaaac atatagctga    120
tgcaacacgg aggataagta agagatacag caactttttt t                        161

SEQ ID NO: 61           moltype = DNA   length = 168
FEATURE                 Location/Qualifiers
source                  1..168
                        mol_type = other DNA
                        organism = synthetic construct
SEQUENCE: 61
gggtgagatg gatgtgattg ataggtaaga ttgtattgct ctgatttcac tcagagcaat     60
actatcttac ctatcaaccg tgttgctaca gctataagta gtgaaatata tattaaacat    120
atagctgatg caacacggag gataagtaag agatacagca acttttttt                168

SEQ ID NO: 62           moltype = DNA   length = 173
FEATURE                 Location/Qualifiers
source                  1..173
```

```
                                   mol_type = other DNA
                                   organism = synthetic construct
SEQUENCE: 62
gggtgagatg gatgtgattg ataggtaaga ttgtattgct ctgatttcac taaaatcaga    60
gcaacccaat cttacctatc aaccgtgttg ctacagctat aagtagtgaa atatatatta   120
aacatatagc tgatgcaaca cggaggataa gtaagagata cagcaacttt ttt          173

SEQ ID NO: 63           moltype = DNA   length = 168
FEATURE                 Location/Qualifiers
source                  1..168
                        mol_type = other DNA
                        organism = synthetic construct
SEQUENCE: 63
gggtgagatg gatgtgattg ataggtaaga ttgtattgct cctacaagca atactatctt    60
acctatcaac cgtgttgcta cagctataag tagtgaaata tatattaaac atatagctga   120
tgcaacacgg aggataagta agagatacag caaccttatc attttttt                168

SEQ ID NO: 64           moltype = DNA   length = 168
FEATURE                 Location/Qualifiers
source                  1..168
                        mol_type = other DNA
                        organism = synthetic construct
SEQUENCE: 64
gggtgagatg gatgtgattg ataggtaaga ttgtattgct cctacaagca atactatctt    60
acctatcaac cgtgttgcta cagctataag tagtgaaata tatattaaac atatagctga   120
tgcaacacgg aggataagta agagatacag caaccttatc attttttt                168

SEQ ID NO: 65           moltype = DNA   length = 193
FEATURE                 Location/Qualifiers
source                  1..193
                        mol_type = other DNA
                        organism = synthetic construct
SEQUENCE: 65
gggtcattat gttatttcgc taatcaggca cggtgtagtt ccgcatagcc caactttccg    60
tgggctatgc ataactacac agtgcctgat tagcaccgtg ttgctacagc tataagtagt   120
gaaatatata ttaaacatat agctgatgca acacggatct aagcaggcag atacagcaac   180
gcttagtttt ttt                                                      193

SEQ ID NO: 66           moltype = DNA   length = 195
FEATURE                 Location/Qualifiers
source                  1..195
                        mol_type = other DNA
                        organism = synthetic construct
SEQUENCE: 66
gggtcgttag ttattagagg tatgcttaag ttcgtatagt cctcggtctc gaccggatca    60
tcgagaccga ttactatacg cacttaagca taccaccgtg ttgctacagc tataagtagt   120
gaaatatata ttaaacatat agctgatgca acacggaagt atacttaagg atacagcaac   180
gtatactatt ttttt                                                    195

SEQ ID NO: 67           moltype = DNA   length = 194
FEATURE                 Location/Qualifiers
source                  1..194
                        mol_type = other DNA
                        organism = synthetic construct
SEQUENCE: 67
gggtcgaatg gtagtaagtt aaggataatg taatgtgtct cacgaggctc tgtggcttac    60
cagagcctcg atagacacat aacattatcc ttaaaccgtg ttgctacagc tataagtagt   120
gaaatatata ttaaacatat agctgatgca acacggaata agaataatgg atacagcaac   180
ttcttaattt tttt                                                     194

SEQ ID NO: 68           moltype = DNA   length = 194
FEATURE                 Location/Qualifiers
source                  1..194
                        mol_type = other DNA
                        organism = synthetic construct
SEQUENCE: 68
gggtgattag ttgaaagata tagaaagcga agtcggtaaa tccgcggtaa gctggtgagg    60
gcttaccgcg tctttaccga attcgctttc tataaccgtg ttgctacagc tataagtagt   120
gaaatatata ttaaacatat agctgatgca acacggacat agcaagcgag atacagcaac   180
tgctatattt tttt                                                     194

SEQ ID NO: 69           moltype = DNA   length = 194
FEATURE                 Location/Qualifiers
source                  1..194
                        mol_type = other DNA
                        organism = synthetic construct
SEQUENCE: 69
gggtgatgag agtaaatgga cgaaatgtag taagtaatga tatcttccat ccaaatcaaa    60
ggatggaaga cttcattact aactacattt cgtcaccgtg ttgctacagc tataagtagt   120
```

```
gaaatatata ttaaacatat agctgatgca acacggacac gacatgtagg atacagcaac    180
tgtcgtattt tttt                                                      194

SEQ ID NO: 70            moltype = DNA   length = 21
FEATURE                  Location/Qualifiers
source                   1..21
                         mol_type = other DNA
                         organism = synthetic construct
SEQUENCE: 70
ttatagctgt agcaacacgg t                                              21

SEQ ID NO: 71            moltype = RNA   length = 21
FEATURE                  Location/Qualifiers
source                   1..21
                         mol_type = other RNA
                         organism = synthetic construct
SEQUENCE: 71
accgtgttgc tacagctata a                                              21

SEQ ID NO: 72            moltype = DNA   length = 21
FEATURE                  Location/Qualifiers
source                   1..21
                         mol_type = other DNA
                         organism = synthetic construct
misc_feature             21
                         note = 3AzideN at the 3' end of the probe.
SEQUENCE: 72
ttatagctgt agcaacacgg t                                              21

SEQ ID NO: 73            moltype = DNA   length = 30
FEATURE                  Location/Qualifiers
source                   1..30
                         mol_type = other DNA
                         organism = synthetic construct
misc_feature             30
                         note = 3AzideN at the 3' end of the probe.
SEQUENCE: 73
gcagggcca tgctaatctt ctctgtatcg                                      30

SEQ ID NO: 74            moltype = DNA   length = 22
FEATURE                  Location/Qualifiers
source                   1..22
                         mol_type = other DNA
                         organism = synthetic construct
misc_feature             22
                         note = 3AzideN at the 3' end of the probe.
SEQUENCE: 74
gtgaagtgaa ggtaaggtag ag                                             22

SEQ ID NO: 75            moltype = DNA   length = 24
FEATURE                  Location/Qualifiers
source                   1..24
                         mol_type = other DNA
                         organism = synthetic construct
misc_feature             24
                         note = 3AzideN is at the 3' end of the probe.
SEQUENCE: 75
aacaacaaaa tcactagtct tcca                                           24

SEQ ID NO: 76            moltype = DNA   length = 77
FEATURE                  Location/Qualifiers
source                   1..77
                         mol_type = other DNA
                         organism = synthetic construct
SEQUENCE: 76
ggaaacccct accaactggt cggggtttga aacagcaata caatcttacc tatcaatcac    60
atccatctca ttttttt                                                   77

SEQ ID NO: 77            moltype = DNA   length = 77
FEATURE                  Location/Qualifiers
source                   1..77
                         mol_type = other DNA
                         organism = synthetic construct
SEQUENCE: 77
ggaaacccct accaactggt cggggtttga acaactaca ccgtgcctga ttagcgaaat     60
aacataatga ttttttt                                                   77

SEQ ID NO: 78            moltype = AA    length = 4
FEATURE                  Location/Qualifiers
```

|   |   |   |
|---|---|---|
| source | 1..4<br>mol_type = protein<br>organism = synthetic construct | |
| SEQUENCE: 78<br>AAAA | | 4 |
| SEQ ID NO: 79<br>FEATURE<br>source | moltype = AA  length = 4<br>Location/Qualifiers<br>1..4<br>mol_type = protein<br>organism = synthetic construct | |
| SEQUENCE: 79<br>CCCC | | 4 |
| SEQ ID NO: 80<br>FEATURE<br>source | moltype = AA  length = 4<br>Location/Qualifiers<br>1..4<br>mol_type = protein<br>organism = synthetic construct | |
| SEQUENCE: 80<br>GGGG | | 4 |
| SEQ ID NO: 81<br>FEATURE<br>source | moltype = AA  length = 5<br>Location/Qualifiers<br>1..5<br>mol_type = protein<br>organism = synthetic construct | |
| SEQUENCE: 81<br>UUUUU | | 5 |
| SEQ ID NO: 82<br>FEATURE<br>source | moltype = AA  length = 6<br>Location/Qualifiers<br>1..6<br>mol_type = protein<br>organism = synthetic construct | |
| SEQUENCE: 82<br>KKKKKK | | 6 |
| SEQ ID NO: 83<br>FEATURE<br>source | moltype = AA  length = 7<br>Location/Qualifiers<br>1..7<br>mol_type = protein<br>organism = synthetic construct | |
| SEQUENCE: 83<br>MMMMMMM | | 7 |
| SEQ ID NO: 84<br>FEATURE<br>source | moltype = AA  length = 7<br>Location/Qualifiers<br>1..7<br>mol_type = protein<br>organism = synthetic construct | |
| SEQUENCE: 84<br>RRRRRRR | | 7 |
| SEQ ID NO: 85<br>FEATURE<br>source | moltype = AA  length = 7<br>Location/Qualifiers<br>1..7<br>mol_type = protein<br>organism = synthetic construct | |
| SEQUENCE: 85<br>SSSSSSS | | 7 |
| SEQ ID NO: 86<br>FEATURE<br>source | moltype = AA  length = 7<br>Location/Qualifiers<br>1..7<br>mol_type = protein<br>organism = synthetic construct | |
| SEQUENCE: 86<br>WWWWWWW | | 7 |
| SEQ ID NO: 87<br>FEATURE<br>source | moltype = AA  length = 7<br>Location/Qualifiers<br>1..7<br>mol_type = protein<br>organism = synthetic construct | |
| SEQUENCE: 87<br>YYYYYYY | | 7 |
| SEQ ID NO: 88 | moltype = RNA  length = 96 | |

```
FEATURE                 Location/Qualifiers
source                  1..96
                        mol_type = other RNA
                        organism = synthetic construct
SEQUENCE: 88
acttgttcca ctctagcagc acgtaaatat tggcgtagtg aaatatatat taaacaccaa    60
tattactgtg ctgctttagt gtgacaggga tacagc                             96

SEQ ID NO: 89           moltype = RNA   length = 96
FEATURE                 Location/Qualifiers
source                  1..96
                        mol_type = other RNA
                        organism = synthetic construct
SEQUENCE: 89
acttgttcca ctcaccgtgt tgctacagct ataagtagtg aaatatatat taaacatata    60
gctgatgcaa cacggatagt gtgacaggga tacagc                             96

SEQ ID NO: 90           moltype = RNA   length = 121
FEATURE                 Location/Qualifiers
source                  1..121
                        mol_type = other RNA
                        organism = synthetic construct
SEQUENCE: 90
ataaacatac atgcgcaact gacatacttg ttccactcac cgtgttgcta cagctataag    60
tagtgaaata tatattaaac atatagctga tgcaacacgg atagtgtgac agggatacag   120
c                                                                  121

SEQ ID NO: 91           moltype = RNA   length = 155
FEATURE                 Location/Qualifiers
source                  1..155
                        mol_type = other RNA
                        organism = synthetic construct
SEQUENCE: 91
ggtcagttcg cgctaatacg actcactata gggataaaca tacatgcgcg aactgacata    60
cttgttccac tcaccgtgtt gctacagcta taagtagtga aatatatatt aaacatatag   120
ctgatgcaac acggatagtg tgacagggat acagc                             155

SEQ ID NO: 92           moltype = RNA   length = 146
FEATURE                 Location/Qualifiers
source                  1..146
                        mol_type = other RNA
                        organism = synthetic construct
SEQUENCE: 92
gcgctaatac gactcactat agggataaac atacatgcgc cctcaacgat acttgttcca    60
ctcaccgtgt tgctacagct ataagtagtg aaatatatat taaacatata gctgatgcaa   120
cacggatagt gtgacaggga tacagc                                       146

SEQ ID NO: 93           moltype = RNA   length = 155
FEATURE                 Location/Qualifiers
source                  1..155
                        mol_type = other RNA
                        organism = synthetic construct
SEQUENCE: 93
gcgttgaggg cgctaatacg actcactata gggataaaca tacatgcgcc ctcaacgata    60
cttgttccac tcaccgtgtt gctacagcta taagtagtga aatatatatt aaacatatag   120
ctgatgcaac acggatagtg tgacagggat acagc                             155

SEQ ID NO: 94           moltype = RNA   length = 124
FEATURE                 Location/Qualifiers
source                  1..124
                        mol_type = other RNA
                        organism = synthetic construct
SEQUENCE: 94
ataaacatac atgcgcaact gacatacttg ttccactcta gcagcacgta aatattggcg    60
tagtgaaata tatattaaac accaatatta ctgtgctgct ttagtgtgac agggatacag   120
caac                                                               124

SEQ ID NO: 95           moltype = RNA   length = 96
FEATURE                 Location/Qualifiers
source                  1..96
                        mol_type = other RNA
                        organism = synthetic construct
SEQUENCE: 95
aagccataac tccaccgtgt tgctacagct ataagtagtg aaatatatat taaacatata    60
gctgatgcaa cacggatagt gtgacaggga tacagc                             96

SEQ ID NO: 96           moltype = RNA   length = 96
FEATURE                 Location/Qualifiers
source                  1..96
```

```
                        mol_type = other RNA
                        organism = synthetic construct
SEQUENCE: 96
acttgttcca ctcaccgtgt tgctacagct ataagtagtg aaatatatat taaacatata    60
gctgatgcaa cacggatgag tcatggctga tacagc                              96

SEQ ID NO: 97           moltype = RNA   length = 96
FEATURE                 Location/Qualifiers
source                  1..96
                        mol_type = other RNA
                        organism = synthetic construct
SEQUENCE: 97
aagccataac tccaccgtgt tgctacagct ataagtagtg aaatatatat taaacatata    60
gctgatgcaa cacggatgag tcatggctga tacagc                              96
```

MIRNA SWITCHES FOR RNA-TRIGGERED CONTROL OF RNA INTERFERENCE

CROSS-REFERENCE TO RELATED APPLICATIONS

This application claims benefit under 35 U.S.C. § 119(e) of U.S. Provisional Application Ser. No. 63/434,292 filed Dec. 21, 2022, the contents of each are incorporated herein in their entirety by reference.

GOVERNMENT SUPPORT

This invention was made with government support under GM126892 and GM128753 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Dec. 21, 2023, is named 701586-000109WOPT.xml and is 95,302 bytes in size.

TECHNICAL FIELD

The technology described herein relates generally to methods, compositions, systems and kits for a conditional, inducible miRNA system, comprising an engineered chimeric pri-miRNA construct that adopts an inactive secondary structure, which can be activated by a trigger RNA molecule to reconfigure it from an inactive secondary structure into an active functional pri-miRNA structure that can initiate miRNA biogenesis.

BACKGROUND

RNA interference (RNAi) has been actively studied over the years and has proven to be a powerful tool for target gene knock-down in both fundamental biological research and medical applications. miRNAs can selectively silence target gene expression by post-transcriptional regulation without perturbing the genome. (RNAi) is a powerful tool for sequence-specific knockdown of gene expression in therapeutic and research applications. However, constitutively active, unregulated RNAi suffers from several drawbacks that limit the range of potential applications. First, delivered RNAi competes with endogenous RNAi, potentially diverting cellular resources in detrimental ways and reducing exogenous RNAi potency. Second, in therapeutic applications, RNAi delivery and activity in nontargeted cells or tissues leads to undesirable off-target effects. Third, unregulated RNAi is challenging to apply to essential genes since knock-down of these genes in the wrong tissues can prove lethal. miRNAs that can be switched on only when they are required provide a potential opportunity for dealing with these issues. Such miRNAs would only compete with endogenous transcripts once activated and could reduce off-target effects and be applied to essential genes. Therefore, spatiotemporal control of RNAi is extremely useful to decrease nonspecific targeting, potential toxicity, and allow targeting of essential genes with minimal side-effects.

RNA switch technology holds great promise in transducing an RNA input signal to an RNAi output signal as a means of precisely regulating activity of a gene of interest. The high programmability and structural predictability of RNA enables automated de novo design for constructing sensing elements and logic circuits with the potential to be interfaced with endogenous biological pathways[15-17]. In recent years, RNA switch techniques have been successfully employed in mammalian cells to upregulate transgene activity. For instance, the eToehold achieved RNA-specific transgene translational activation through regulating RNA structure at internal ribosome entry sites (IRESs)[18]. Several studies have established programmable RNA-sensing-dependent protein translation technologies in which specific RNA base-pairing motifs recruit ADARs to edit RNA for transgene translational activation[19-21]. However, downregulation of endogenous genes in mammalian cells through programmable RNA switch techniques remains largely unexplored despite many potential applications where conditional gene silencing is desired[22].

In the canonical pathway, miRNA biogenesis is initiated in the nucleus by the Microprocessor complex, which is comprised of the nuclear RNase III Drosha and two DGCR8 proteins as cofactors. Microprocessor searches through the RNA transcripts to identify and cleave primary (pri-) miRNAs, releasing hairpin-shaped precursor (pre-) miRNAs that are then exported into the cytoplasm for further cleavage by Dicer into mature miRNA[23,24]. Both Microprocessor and Dicer recognize substrate RNAs by conserved RNA motifs and specific secondary structures, thus providing the opportunity to regulate substrate RNA accessibility by disruption of Microprocessor or Dicer recognition elements[25-27]. Prior efforts to conditionally regulate RNAi activity have focused on Dicer substrate RNA formation[13,14]; however, Dicer substrate RNA requires characteristic double-stranded RNA helical ends with 5' phosphate and a 3' 2-nt overhang[26,27]. These structural requirements make it challenging to incorporate cis-regulatory elements for substrate activation. Thus far Dicer substrate-based RNA transducing systems have only employed trans-acting RNA molecules in test tubes[13] and cell lysate[14] and have yet to be demonstrated in live cells.

However, earlier attempts at making conditional RNAi systems that activate in response to cognate trigger RNAs have been lacking. Prior endeavors have focused on Dicer substrate formation, however, Dicer substrate RNA requires characteristic double-stranded RNA helical ends with 5' phosphorylation and a 3' 2-nt overhang. These structural requirements make incorporation of the cis-regulatory elements necessary for substrate activation challenging. The previously reported Dicer substrate-based conditional RNAi systems have required multi-strand complexes that are very hard to assemble in live cells and have been limited to demonstrations in vitro with cell lysates.

Therefore there is a great need for methods and kits for programmable RNA switches and methods for activating miRNA biogenesis in a controlled and tunable manner that address one or more of the above noted issues in the field. The present disclosure addresses these needs, including demonstrating an inducible miRNA switch for production of miRNA in mammalian cells, including live cells.

SUMMARY

The technology described herein relates, in general, to an engineered synthetic toehold-mediated riboregulator that reconfigures from an inactive secondary structure into an active secondary structure in the presence of a trigger RNA molecule, where the active secondary structure forms a pri-miRNA scaffold structure that can undergo miRNA bioprocessing. Thus, the technology described herein in all aspects relates to methods, compositions, kits and systems comprising an engineered chimeric miRNA scaffold and a RNA-trigger molecule for sensitive, specific, and reliable production of a miRNA to a nucleic acid target of interest (GOI) for effective knock-down of the GOI in a cell, e.g., a mammalian cell.

Herein, the technology relates to an engineered synthetic trigger-activated pri-miRNA construct, termed Orthogonal RNA Interference induced by Trigger RNA (ORIENTR), which adopts a secondary structure that can be perturbed in the presence of a specific RNA stimuli, to adapt to a different secondary structure thereby enabling the production of a RNAi molecule, e.g., miRNA molecule in the presence of the specific RNA stimuli. More specifically, in the absence of a RNA-trigger molecule, the ORIENTR adopts a secondary structure that precludes the correct pri-miRNA substrate structure from forming, and therefore preventing Drosha acquisition and processing of the pri-miRNA. In the presence of the RNA-trigger, the ORIENTR undergoes toehold-mediated strand displacement to release a sequestered 11bp sequence that can form a basal stem reconfiguration domain to activate Drosha and allow the microprocessor to initiate miRNA biogenesis (e.g., identify and cleave primary (pri-) miRNAs to release a hairpin-shaped precursor (pre-) miR-NAs, that are then exported into the cytoplasm for further cleavage by Dicer into mature miRNA).

Accordingly, provided herein are compositions, kits, systems and methods related to a ORIENTR riboregulator, which is an engineered nucleic acid construct that functions as a conditional pri-miRNA system that operates in mammalian cells and relies on binding of a cognate trigger RNA to form an active secondary structure substrate that can be recognized and processed by the Microprocessor to produce pre-miRNA for induced target gene suppression e.g., RNA interference (RNAi). Without being limited to theory, in the absence of the trigger RNA, the ORIENTR construct adopts an inactive secondary structure that precludes recognition by Microprocessor. In the presence of the trigger RNA, the ORIENTR adopts a different secondary structure (i.e., an active secondary structure) that enables the microprocessor to recognize and bind and allows the processing of the pri-miRNA into pre-miRNA, which can be subsequently processed to a miRNA duplex for downstream miRNA-mediated gene silencing.

Accordingly, provided herein are compositions, kits, systems and methods related to a ORIENTR riboregulator that is a conditional RNAi system that can be regulated by cellular RNAs in mammalian cells, where the conditional RNAi is used in a system of perturbing molecular recognition between RNA substrate (e.g. pri-miRNA) and essential enzymes in the RNAi bioprocessing or biogenesis pathway. Herein, the inventors have developed a conditional RNAi construct and system that functions robustly in mammalian cells, which responds to trans RNA (e.g., the RNA trigger) by utilizing cis-regulatory RNA elements in the ORIENTR to control recognition of a pri-miRNA substrate by the Microprocessor.

As such, the inventors designed and developed the sequence and structural requirements for a functional and conditional pri-miRNA scaffold, referred to herein as a single-stranded ORIENTR construct or device, which is configured into an inactive secondary structure in the absence of a trigger RNA. In the presence of a trigger RNA, the ORIENTR device reconfigures its secondary structure into an active configuration, consisting of a sensing domain, a reconfiguration domain and an output domain that can robustly fold into a prescribed pri-miRNA structure in mammalian cells.

Importantly, the ORIENTR device as disclosed herein decouples RNA input sequence (i.e., the trigger RNA) and output sequence (miRNA) such that an arbitrary RNA input, such as a synthetic trigger RNA, can generate any desired output miRNA from its cognate ORIENTR. Herein, the inventors demonstrate functional and orthogonal ORIENTR devices in human cells, as well as modifications, including (i) using a deactivated CRISPR nuclease dCas13d to facilitate RNA-RNA interaction and (ii) nuclear localization for improved performance. Accordingly, herein the inventors have demonstrated programmable RNAi-based synthetic circuits in mammalian cells.

One aspect of the technology disclosed herein relates to an engineered nucleic acid construct comprising an Orthogonal RNA Interference induced by Trigger RNA (ORIENTR) molecule, the ORIENTR molecule comprising, in a 5' to 3' order: (i) a single stranded 5' toehold domain (T1), (ii) a fully or partially double-stranded RNA sequestering-Loop domain (SLD) comprising: (a) a 3' sequestering arm region comprising a 5' region (S1) and a 3' region (S2), (b) a loop, (c) a 3' flanking sequence (S2'), wherein 3' flanking sequence forms a RNA duplex with a 3' region (S2) of the sequestering arm region, and (d) a 5' basal stem (5'-BS) sequence, wherein 5' basal stem sequence forms a RNA duplex with a 5' region (S1) of the sequestering arm, and (iii) an output domain, the output domain comprising a fully or partially double-stranded RNAi hairpin, such as, e.g., a pre-miRNA duplex, comprising: (a) a guide strand sequence targeting a nucleic acid of interest, (b) a loop sequence (which can, e.g., be an apical loop in the case of a pre-miRNA duplex), and (c) a passenger strand sequence to the guide strand sequence, where the passenger strand forms a partially or full double stranded stem with the guide strand sequence; (iv) a 3' basal stem (3' BS) sequence, wherein 3' basal stem sequence capable of complementary base pairing with 5' basal stem sequence to form a basal stem structure that is recognized and can be bound by Drosha. In such an embodiment, the ORIENTR is in an ORIENTR-OFF configuration.

In some embodiments, the RNAi hairpin in the output domain of the ORIENTR is a pri-miRNA hairpin structure, and the loop sequence in the output domain is an aptical loop.

In some embodiments, when the ORIENTR is in an ORIENTR-OFF configuration, the loop of the sequestering loop domain (SLD) is part of a hairpin-stem loop (HSL) structure, that is there is a stem-loop structure 3' of 3' sequestering arm sequence and 5' of 3' flanking sequence.

In some embodiments, the ORIENTR further comprises a spacer sequence located 3' of the 3' basal stem sequence. In some embodiments, the spacer is single stranded and functions as a 3' flanking sequence to the pri-miRNA scaffold structure (with the basal stem), and can optionally comprise one or more nucleic acids to enhance such the function, e.g., CNNC.

In some embodiments, the ORIENTR can further comprises a RNA terminator sequence located 3' of 3' basal stem sequence or 3' of the spacer sequence, where the terminator sequence is selected based on the promoter used to express the ORIENTR, e.g., in some embodiments, it is a Pol III terminator sequence.

In some embodiments, when the ORIENTR is in an ORIENTR-OFF configuration (e.g., in the absence of a RNA trigger), 3' basal stem sequence is single stranded.

In some embodiments, the spacer sequence of the ORIENTR can comprise a small hairpin sequence (SHS), which is located 3' of 3' basal stem sequence, wherein SHS is capable of forming a partial or full RNA-duplex with at least about 2 bp or 3 bp, or 4 bp, or 5 bp, or 6 bp, or 7 bp or to more nucleotides of 3' portion of 3' basal stem sequence to form a leak-reduction motif, where the leak-reduction motif serves to prevent the processing of the RNAi hairpin, e.g., it prevents the processing to the pre-miRNA hairpin structure when the basal stem has not formed and the RNA trigger is not present.

In some embodiments, such a SHS can be, e.g., at least 5 bp in length, and can weakly complementary base pair with at least 2 bp, or at least 3 bp, or at least 4 bp or at least 5 bp of 3' basal stem sequence.

As disclosed herein, the ORIENTR discussed above can exist in an ORIENTR-OFF configuration in the absence of a RNA trigger. However, in the presence of a RNA trigger molecule, the ORIENTR reconfigures from an ORIENTR-OFF to an ORIENTR-ON domain by complexing with the RNA trigger molecule, which induces changes in the secondary structure of the ORENTR to allow the pri-miRNA to form into a correct pri-miRNA scaffold structure to allow the biogenesis of the pri-miRNA from the output domain by microprocessor. Accordingly, as disclosed herein in the presence of a RNA-trigger sequence, the ORIENTR molecule is reconfigured to an ORIENTR-OFF configuration and comprises a secondary structure, in a 5' to 3' order: (a) a RNA duplex comprising 5' toehold domain (T1) and S1 and S2 regions of 3' sequestering arm duplexed with a cognate RNA sequence of a RNA-trigger sequence, (b) a single stranded 3' flanking sequence (S2$^f$), and (c) a pri-miRNA scaffold comprising a fully or partially double stranded RNA duplex comprising, in a 5' to 3' order: (i) 5' basal stem (5'-BS) sequence, (ii) the output domain, the output domain comprising a fully or partially double-stranded RNAi hairpin, comprising the guide strand sequence targeting a nucleic acid of interest, the loop sequence, and the passenger strand sequence, and (iii) 3' basal stem (3'-BS) sequence, wherein 5' basal stem sequence and 3' basal stem sequence exist in a RNA-duplex that serves as a basal stem structure that can be recognized and bound by Drosha.

In some embodiments, 5' basal stem sequence is at least 11bp, and 3' basal stem sequence is at least 11bp, however, this can be modified by one of ordinary skill in the art to be a basal stem that is recognized by Drosha to enable microprocessor processing of the pri-miRNA scaffold structure. In some embodiments, 5' basal stem and 3' basal stem can range between 8-14nt in length, or more than 14nt in length, forming a 8-14 bp basal stem structure when the ORIENTR is in the ORIENTR-ON configuration. In some embodiments, a double stranded stem structure (i.e., RNA-duplex) formed by base pairing of 5' basal stem sequence and 3' basal stem sequence is an imperfect RNA-duplex basal stem structure that can be recognized and bound by Drosha—that is, it has at least one or more base pair mismatches in the stem structure. The sequences of 5' basal stem and 3' basal stem sequences can be modified based on the scaffold structures and sequences derived from other endogenous pri-miRNA scaffolds (e.g., other than an pri-miRNA 16-2) that can enable the processing of a pri-miRNA into a single miRNA from the 5' arm of the hairpin (5p-miRNA).

As disclosed herein, a RNA trigger comprises, in a 3' to 5' orientation, a T1* region, a S1* region and a S2* region, wherein the T1* region can complementary base pair with the toehold region T1 of the ORIENTR molecule, the S1* can complementary base pair with the S1 region of 3' sequestering arm sequence of the ORIENTR molecule, and the S2* can complementary pair with the S2* region of 3' sequestering arm sequence of the ORIENTR molecule. In some embodiments, a RNA trigger further comprises a stability hairpin at the 5' end. In some embodiments, a stability hairpin is a CRISPR RNA (crRNA) hairpin, e.g., a rfxCas13d scaffold hairpin, or can be bound by dCas13d.

Accordingly, in some embodiments, a RNA trigger comprises, in a 5' to 3' orientation, a small stabilizing hairpin, a S2* region, a S1* region and a T1* region. The size of the RNA trigger depends on if the RNA trigger is an endogenous RNA in the cell or the like. In some embodiments, the cumulative length of the RNA trigger (not including the stability hairpin), e.g., the T1*, S1* and S2* regions of the RNA trigger together, can be between 9-50 nucleotides.

In some embodiments, any one or more of 5' toehold domain (T1) and the S1 or S2 regions, or both, or 3' sequestering arm of an ORIENTR as disclosed herein is a synthetic sequence, and accordingly, a cognate RNA sequence of a RNA-trigger sequence is also synthetic sequence.

In some embodiments, 5' toehold domain (T1) and the S1 or S2 regions (or both), 3' sequestering arm can form a double-stranded duplex with a cognate RNA sequence of a RNA-trigger sequence that is an endogenous RNA sequence. Exemplary RNA sequences that can be used as a RNA trigger can include, but are not limited to, endogenous RNA sequences selected from the group consisting of: a tissue specific RNA sequence, a disease specific RNA sequence, an environmental RNA sequence, a developmental RNA sequence, a temporal RNA sequence, a cell-cycle specific sequence.

Another aspect of the technology disclosed herein relates to a system comprising the ORIENTR molecule as disclosed herein, and a RNA trigger molecule as disclosed herein.

In some embodiments, the RNA trigger comprises a T1* region, a S1* region and a S2* region, wherein the T1* region can complementary base pair with the toehold region T1 of the ORIENTR molecule, the S1* can complementary base pair with the S1 region of 3' sequestering arm sequence of the ORIENTR molecule, and the S2* can complementary pair with the S2* region of 3' sequestering arm sequence of the ORIENTR molecule.

Another aspect of the technology disclosed herein relates to a nucleic acid encoding a ORIENTR as disclosed herein. In some embodiments the nucleic acid can be present in a vector, e.g., a viral vector or other expression vector. Accordingly, one aspect of the technology relates to a vector comprising a first promoter operatively linked to a nucleic acid sequence encoding the ORIENTR as disclosed herein. In some embodiments, the vector further comprises a nucleic acid encoding a RNA trigger sequence to the ORIENTR, wherein the nucleic acid encoding the RNA trigger sequence is operatively linked to the first promoter, or a second promoter. In some embodiments, the vector comprises a nucleic acid sequence that encodes a RNA trigger that comprises a T1* region, a S1* region and a S2* region, wherein the T1* region can complementary base pair with the toehold region T1 of the ORIENTR molecule expressed by the vector, the S1* can complementary base pair with the S1 region of the 3' sequestering arm sequence of the ORIENTR molecule expressed by the vector, and the S2* can complementary pair with the S2* region of 3' sequestering arm sequence of the ORIENTR molecule expressed by the vector.

In some embodiments, the expression of the ORIENTR and/or RNA trigger is under the control of a specific promoter, e.g., where first promoter and/or second promoter can be selected from any of: a constitutive promoter, a tissue specific promoter, inducible promoter, cell cycle dependent promoter, cell stress dependent promoter, inflammation inducible promoter, hypoxia induced promoter.

In some embodiments, the expression of the ORIENTR and/or RNA trigger are under the control of the same promoter, or in some embodiments, they are under the control of different promotes, e.g., where the first promoter is a different promoter to the second promoter. In some embodiments, the vector is a viral vector, e.g., where the viral vector is selected from the group consisting of: AAV, Adenovirus vector, lentivirus vector and HSV. In some embodiments, the vector is a non-viral vector, e.g., a closed-end DNA or RNA vector (ceDNA or ceRNA) vector, or other non-viral vector, such as doogy bone vector, and other circular non-viral vectors.

Another aspect as disclosed herein relates to a cell comprising the ORIENTR as disclosed herein. In some embodiments, the cell also comprises a RNA trigger, e.g., where the RNA trigger is an exogenous RNA trigger (i.e., introduced into the cell). In some embodiments, the cell comprises a ORIENTR that is responsive to a RNA trigger that is an endogenous RNA trigger as disclosed herein, e.g., where the RNA trigger comprises an endogenous RNA sequence to the cell, as disclosed herein. In some embodiments, the cell can comprise a vector comprising a nucleic acid that encodes an ORIENTR as disclosed herein. In some embodiments, the cell can also comprise a second vector encoding the RNA trigger, or alternatively, the RNA trigger can be expressed from the same vector encoding the ORIENTR as disclosed herein. In some embodiments, the cell comprises a system comprising the ORIENTR and a RNA-trigger as disclosed herein.

In some embodiments, the cell is a mammalian cell, e.g., a human cell. In some embodiments, the cell is a living cell. In some embodiments, the cell is an in vivo cell. In some embodiments, the cell is ex vivo and can be delivered or administered to the subject. In some embodiments, the cell is present in a human subject in need of treatment.

Another aspect of the technology disclosed herein relates to a method for treating a subject with a disease or disorder, the method comprising administering an ORIENTR as disclosed herein to the subject, or a cell comprising an ORIENTR to the subject, wherein the subject is in need of treatment and wherein the subject in need of treatment is in need of RNA interference (RNAi) or a miRNA to reduce or repress a target nucleic acid in a cell in the subject. In some embodiments, the ORIENTR is administered to a subject by administering a vector comprising a nucleic acid that encodes an ORIENTR and/optionally, encodes a RNA-trigger as disclosed herein.

The ORIENTR system as disclosed herein is an improvement over previous conditional RNAi systems based on Dicer processing that are activated by small molecules have been reported (Beisel at al., Nucleic Acids Research, 2011; 39 (7); 2981-2994, which is incorporated herein in its entirety) as these are limited in their use due to the very limited number of small molecules to activate the RNAi, which severely limits their utility. Moreover, such systems disclosed in Beisel at al., did not show robust and strong switching behavior.

The conditional miRNA system as disclosed herein is useful as an RNAi therapy with reduced off-target side effects and the ability to modulate miRNA activity based on other transcripts can enable the system to target essential genes, which can be used to induce death in specific cells (e.g. cancer cells). The system could also be used for cell biology studies for measuring the presence of particular transcripts and for imaging.

The invention is designed to be very modular. The triggering nucleic acid can have any sequence. The output miRNA can also have any sequence. This means that it can be applied to many different possible targets and be activated in a variety of conditions. It should also be possible to have more than one triggering nucleic acid activate the system. Modified bases can also be used to increase stability and potency.

BRIEF DESCRIPTION OF THE DRAWINGS

FIG. 1A shows Structural features and sequence motifs of pri-miRNA substrates. The identified bold line shown by the arrow shows the location of the sequence that matures into a 5p miRNA. FIG. 1B shows an investigation of pri-miRNA 16-2 sequence and structural elements required for RNAi activity: (1) original pri-miRNA 16-2, (2) the sequence for miR16-2 was swapped with miR-HSUR4, a viral microRNA sequence, to target a GFP reporter, (3) change of 5' basal stem m to the scrambled sequence n to disrupt base-pairing, (4) change of 3' basal stem m'* to scrambled sequence n'* to disrupt base-pairing, and (5) change of the basal stem sequence from m-m'* to n-n'* to reconstruct stem structure. Top diagrams depict the pri-miRNA secondary structures predicted by RNAfold[42] (see FIG. 4C for nucleotide-resolution diagrams). Bottom images show the GFP reporter signal cells transfected with the pri-miRNAs. FIG. 1C is a schematic of an exemplary ORIENTR design, showing that 3' sequestration arm prevents formation of the basal stem. Binding of the RNA trigger to the sensing domain (i.e., toehold and 3' sequestering arm sequence) releases 5' basal stem sequence (5'-BS) and leads to formation of the basal stem (formed by the complementary base pairing of 5'-BS and the 3'-BS) within the reconfiguration domain, which then enables processing of the output domain into a functional miRNA. FIG. 1D shows optical microscopy images of 19 different ORIENTR designs with and without expression of their cognate trigger RNAs. ORIENTR activation leads to production of a miRNA output targeting the GFP mRNA.

FIG. 2A shows an exemplary RNA secondary structure for ORIENTR_2 (2) and its derivatives; ORIENTR 2_1, 2_2, 2_3 and 2_4. The exemplary ORIENTR 2 comprises, for example, a 13nt S1 region, connected with a 1nt mismatch to a 8nt S2 region in 3' sequestering arm sequence, with a 2nt mismatch, followed by a hairpin stem loop (HSL) comprising a 10nt stem and 8nt loop, a 13nt 3' flanking sequence (S2'), a 11nt 5'-BS, an output domain comprising a miRNA guide strand, apical loop and passenger strand, and 11nt 3' basal stem sequence. Exemplary derivative ORIENTR 2_1 lacks a hairpin stem loop (HSL) and has a 6nt loop connecting the 3' end of the S2 sequence to the 5 of 3' flanking sequence; exemplary derivative ORIENTR 2_2 has a short hairpin stem loop (HSL) having ~ 2-6nt stem and small 6nt loop and lacks a mismatch at the base of the HSL, exemplary derivative ORIENTR 2_3 has a long 3' sequestering arm sequence of ~15nt, and a 2nt mismatch and a short 3' region, a hairpin stem loop (HSL) having ~ 12nt stem and small 5nt loop and lacks a mismatch at the base of the HSL, and exemplary derivative ORIENTR 2_4 is similar to ORIENTR 2_1, except that it comprises a leak-reduction motif 3' of the 3-basal stem sequence. FIG. 2B shows the luminescence signal from cells transfected with ORIENTR_2 and its derivatives with cognate or non-cognate trigger RNAs using a luciferase reporter. FIG. 2C is schematic illustration of an exemplary ORIENTR with an exemplary leak-reduction motif located 3' of 3' basal stem sequence, which partially hybridizes to a 3' portion of 3' basal stem sequence to suppress miRNA biogenesis without the RNA trigger. FIG. 2D shows the performance of six exemplary ORIENTRs (ORIENTR_2, 13, 9 7, 11, 6, referred to as A, B, C, D, E, and F respectively) with or without the leak-reduction motif modification (presence of leak-reduction motif is referred to as "modified" in FIG. 2D) from luciferase reporter with cognate or non-cognate triggers. n=3 biological replicates, bars represent the mean+s.d.

FIG. 2E shows an orthogonality test for six optimized ORIENTRs against six triggers with miRNA northern blot. U6 was probed as the loading control.

FIG. 3A shows the cellular localization profile of a RNA trigger in the cytoplasm and nucleus. FIG. 3B is a schematic showing an exemplary modification to a RNA-trigger design to change 5' stabilizing stem to a crRNA hairpin (cr-trigger) to form a complex with dCas13d bearing a nuclear localization signal (NLS). FIG. 3C shows results of a northern blot comparing performance between the original trigger (with a stability hairpin) and modified trigger (with a cr hairpin) in the presence of dCas13d for two representative ORIENTRs. The numbers below the miR-HSUR4 bands are the quantitated band intensity after normalization by miR-7 and by the control group.

FIG. 4A shows the structure of pri-miR-16-2 (left) and pri-miR-HSUR4 (right). In pri-miR-HSUR4, the sequence for miR16-2 was swapped with miR-HSUR4, a viral microRNA sequence, and the secondary structure was preserved. A GFP reporter mRNA harboring a miR-HSUR4 target site is silenced by pri-miR-HSUR4 but not by pri-miR-16-2. FIG. 4B shows the original scaffold 5' flanking sequence (highlighted in a bracket) upstream of the basal stem was modified in terms of sequence and structure by: (1) structurally sequestering the upstream sequence with base-pairing in cis, (2) inserting an 8-nt sequence between the flanking sequence and the basal stem, and (3) inserting the 8-nt sequence while introducing a 5' base-pairing structure in cis. FIG. 4C shows Nucleotide-level secondary structures of pri-miRNA 16-2 variants used in FIG. 1B.

FIG. 5A shows an exemplary ORIENTR riboregulator (without a leak-reduction motif) in the ORIENTR-OFF configuration, showing the RNA-sensing domain (made up of the toehold region and 3' sequestering arm sequence) that marks the trigger interaction domain, the secondary structure of the sequestering loop domain (SLD) comprising 3' sequestering arm region, an optional hairpin stem loop (HSL). A 3' flanking sequence, a 5' basal stem, and the output domain comprising the guide strand, aptical loop, and passenger strand, and where 3' basal stem sequence, and optional spacer sequence are exist in a single stranded. FIG. 5B shows the secondary structure of an exemplary RNA-trigger molecule comprising, in a 5' to 3' direction; a 5' stability hairpin and a single stranded RNA sequence that comprises S2*, S1* and T1* sequences that can complementary pair with, the S2, S1, and toehold (T1) sequences respectively on the RNA-trigger sensing domain of the ORIENTR. FIG. 5C shows the secondary structure of the reconfigured exemplary ORIENTR riboregulator of FIG. 5A complexed with the RNA-trigger shown in FIG. 5B, such that the ORIENTR is now in the ORIENTR-ON configuration, where the RNA-trigger has complementary base-paried with the RNA-sensing domain (made up of the toehold region and 3' sequestering arm sequence), disassembling 3' sequestering loop domain (SLD) and so that the displaced 5' basal stem sequence complementary base pairs with 3' basal stem sequence to from the basal stem of the reconfiguration domain, so the output domain is in the correct pri-miRNA scaffold structure to be processed by microprossor. In this exemplary example, 3' flanking sequence is single stranded in this ORIENTR-ON configuration and the optional hairpin stem loop remains but does not interferre with recruitment of Drosha binding and microprocessor processing the miRNA guide sequence from the output domain.

FIG. 9 provides the basic secondary structure configuration and terminology of an exemplary ORIENTR riboregulator, showing the general change in secondary structure from an INACTIVE ORIENTR (ORIENTR-OFF) to an ACTIVE ORIENTR (ORIENTR-ON) configuration (i.e., an ORIENTR-RNA Trigger Complex). d.s.=double stranded, s.s.=single stranded.

Figure 1A:
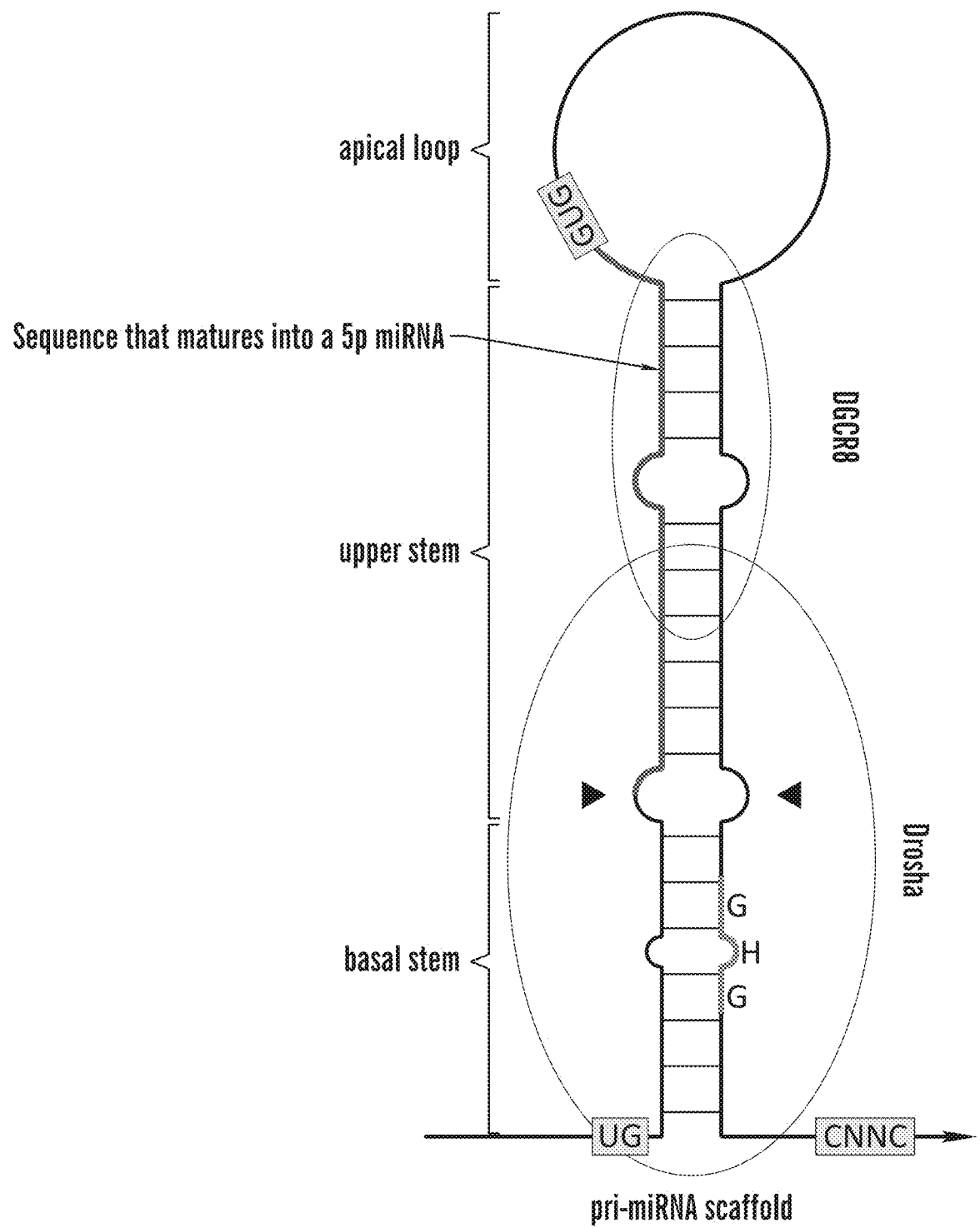
FIGS. 1A-1D show exemplary design and implementation of ORIENTRs based on pri-miRNA substrates.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Provided herein are compositions, kits, systems and methods related to a RNA trigger-activated pri-miRNA construct, termed Orthogonal RNA Interference induced by Trigger RNA (ORIENTR). As disclosed herein, the ORIENTR is a nucleic acid construct that functions as a conditional pri-miRNA system that operates in mammalian cells and relies on binding of a cognate trigger RNA to form an active secondary structure substrate that can be recognized by the Microprocessor and processed into pre-miRNA for induced target gene suppression e.g., RNA interference (RNAi).

Without being limited to theory, in the absence of the trigger RNA, the ORIENTR construct adopts an inactive secondary structure that precludes recognition by Microprocessor. In the presence of the trigger RNA, the ORIENTR adopts a different secondary structure (i.e., an active secondary structure) that enables the microprocessor to recognize and bind and allows the processing of the pri-miRNA into pre-miRNA, which can be subsequently processed to a miRNA duplex for downstream miRNA-mediated gene silencing.

MicroRNAs (miRNAs) are small RNA molecules that direct translational repression. The biosynthesis of 19-23 nucleotide miRNAs is initiated within the nucleus of cells with the cleavage of a primary-miRNA (pri-miRNA), which is a scaffold for the miRNA, by the RNase III enzyme Drosha and its cofactor DGCR8. More specifically, Drosha removes the single-stranded flanks that are characteristic of pri-miRNAs and 11 nucleotides of the basal stem to form pre-miRNAs. Pri-miRNAs are exported from the nucleus, and in the cytoplasm, Dicer removes the terminal loop from pri-miRNAs, forming a 19-23nt RNA duplex, frequently referred to "miR:miR*", representing the guide strand and passenger strand, respectively. miRs are preferentially loaded into the RNA-induced silencing complex (RISC), formed by TRBP, Ago2, and Dicer. In association with RISC, the miRs guide the complex to bind mRNAs with target sequences that imperfectly base-pair with an miR 'seed region' of at nucleotides 2-7 from the 5'-end of the miR.

Herein, the technology relates to an ORIENTR riboregulator that comprises a pri-miRNA duplex that can, in the presence of a RNA signal (e.g., RNA-trigger as disclosed herein), be reconfigured into the correct secondary structure of a pri-miRNA scaffold to enable it to be recognized and cleaved by Drosha and then undergo subsequent miRNA biogenesis.

As disclosed herein, a ORIENTR molecule as disclosed herein employ cis-repressing RNA secondary structures to prevent miRNA biogenesis. Specifically, in the absence of a RNA-trigger, the ORIENTR is in an inactive confirmation that has secondary structures that prevent and/or occlude Drosha binding and miRNA biogenesis, therefore a pri-miRNA in the output domain cannot be processed into pre-miRNA. However, as represented in FIG. 1C, in the presence of a cognate RNA-trigger molecule, the RNA trigger binds to a toehold region on the ORIENTR molecule, resulting in the ORIENTR molecule undergoing substantial secondary structure rearrangement and refolding into a prescribed structure comprising a (i) sensing domain, (ii) reconfiguration domain and (iii) output domain, where the reconfiguration domain and output domain together form a pri-miRNA scaffold that can be recognized and processed by Drosha. Importantly, such complex secondary structure rearrangement of ORIENTR in the presence of a RNA-trigger can occur in living cells, including mammalian cells such as human cells.

As the sensing domain (comprising a toehold sequence and 3' sequestering arm sequence) and output domains are not correlated in sequence, it enables a ORIENTR to be designed with the capacity to direct RNAi in a tissue-specific manner, e.g., be responsive to tissue specific RNA-trigger molecules, and therefore ORIENTR can be used for a targeted RNA interference response in a tissue-specific manner.

Moreover, the technology disclosed herein encompasses optimized ORIENTR designs, and/or optimized RNA-trigger designs, including (i) reduction of signal leakage from ORIENTRs by modification to RNA structure, and (ii) and optimization of regulation dynamics by transporting the trigger RNA back to the nucleus with dCas13d (see, e.g., FIG. 2 and FIG. 3).

Accordingly, aspects of the technology disclosed herein relates to the use of ORIENTR and RNA-triggers, and systems, cells and constructs comprising the same for use as programmable cellular RNAs to regulate RNA interference (RNAi) in living cells.

The advantages of such compositions, methods and systems comprising a ORIENTR as disclosed herein are multifold and include, for example, use as a synthetic regulatory mechanism of RNA in mammalian cells and organisms. In some embodiments, ORIENTR can be used, e.g., for programming and rewiring cell behavior in response to RNA expression profiles for diagnostic or therapeutic purposes, e.g., for example, for conditional regulation and induction of miRNA expression for the treatment of a disease or disorder where aberrant RNA is detected, where in some instances, the aberrant RNA that occurs in a subject with a disease can serve as RNA-trigger to change the ORIENTR confirmation from an inactive conformation to active confirmation, thus enabling miRNA expression in living cells where the aberrant RNA is present.

I. Conditional RNA Interference (RNAi) Via RNA Transactivation

As disclosed herein, ORIENTR as disclosed herein can adapt two distinct secondary structure configurations; (i) an INACTIVE configuration (e.g., ORIENTR-OFF) which occurs in the absence of a RNA-trigger, and (ii) an ACTIVE configuration (e.g., ORIENTR-ON), which occurs in the presence of a cognate RNA-trigger molecule and when the ORIENTR is in a complex with the RNA-trigger, resulting in a secondary confirmation that allows the formation of a pre-miRNA scaffold, which can be processed by Microprocessor to produce miRNA, which in turn enables miRNA-mediated RNA interference (RNAi).

Without being bound to any particular theory or mechanism of action, it is believed that the inventors addressed limitations associated with inducible systems for miRNA activation using a novel ORIENTR molecule, which is based on toehold-mediated changes in secondary structure in the presence of a specific RNA trigger molecule. Expression of a miRNA from the ORIENTR is initially turned off because a pri-miRNA sequence in the output domain is not in a correct scaffold configuration that can be recognized by Drosha due to 5' basal stem sequence, which is required for the basal stem of pri-miRNA scaffold is sequestered a duplex of a stem-loop structure of the sequestering-loop domain. When a target RNA binds to the toehold of the ORIENTR, the repressing stem-loop structure of the sequestering-loop domain disrupted, releasing 5' basal stem sequence and allowing it to duplex with the 3' basal stem sequence and the formation of the reconfiguration domain; thus, forming the correct pri-miRNA scaffold that enables Drosha recruitment and recognition and processing of the miRNA. The miRNA output enables regulation of the expression of a downstream target nucleic acid (e.g., repression of a target gene or other non-coding nucleic acid).

Importantly, the ORIENTRs disclosed herein completely decouple the trigger RNA sequence from output miRNA sequence such that an arbitrary RNA input can be used to silence any desired mRNA without affecting the sequence of the output, e.g., the sequence of the pri-miRNA. This enables the ORIENTR to be used as a programmable conditional RNAi synthetic circuit in mammalian cells, allowing regulation of gene expression, via miRNA repression under specific RNA conditions, e.g., whether the RNA-trigger is a synthetic RNA or endogenous RNA to a cell expressed in specific environmental conditions, cellular state conditions or disease states.

As described in the following paragraphs and the Examples section, the ORIENTRs provided herein have the capacity to control the processing and production of miRNA in in vivo, including in mammalian cells in vivo, and can be adapted to enable RNA interference (RNAi) to any target nucleic acid sequence in response to a trigger RNA. Accordingly, the ORIENTR riboregulators and "devices" derived therefrom that offer greatly improved diversity, orthogonality, and functionality compared to previously described riboregulators for regulating miRNA expression.

II. ORIENTR: Orthogonal RNA Interference Induced by Trigger RNA

A first aspect of the technology disclosed herein is a "Orthogonal RNA Interference induced by Trigger RNA" also referred to herein as "ORIENTR" molecule, which refers to a synthetic RNA construct comprising structural elements, e.g., RNA-based hairpin structures, that rearrange and reconfigure when the ORIENTR complexes with a cognate RNA-trigger molecule, enabling miRNA bioprocessing.

Figure 5A:
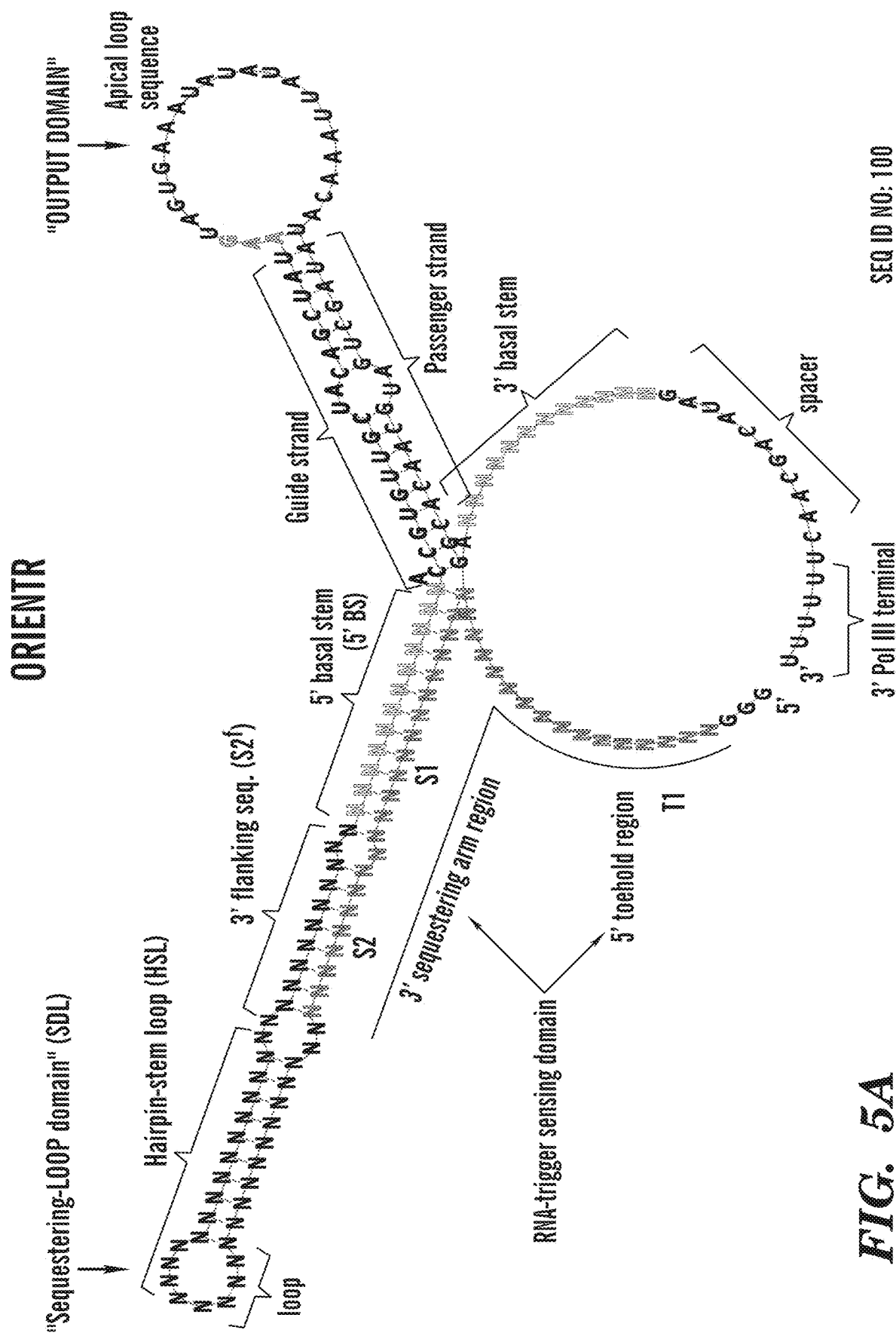
FIG. 5A-5C show NUPACK secondary structure design for the ORIENTR, trigger and ORIENTR-trigger complex.
Figure 5B:
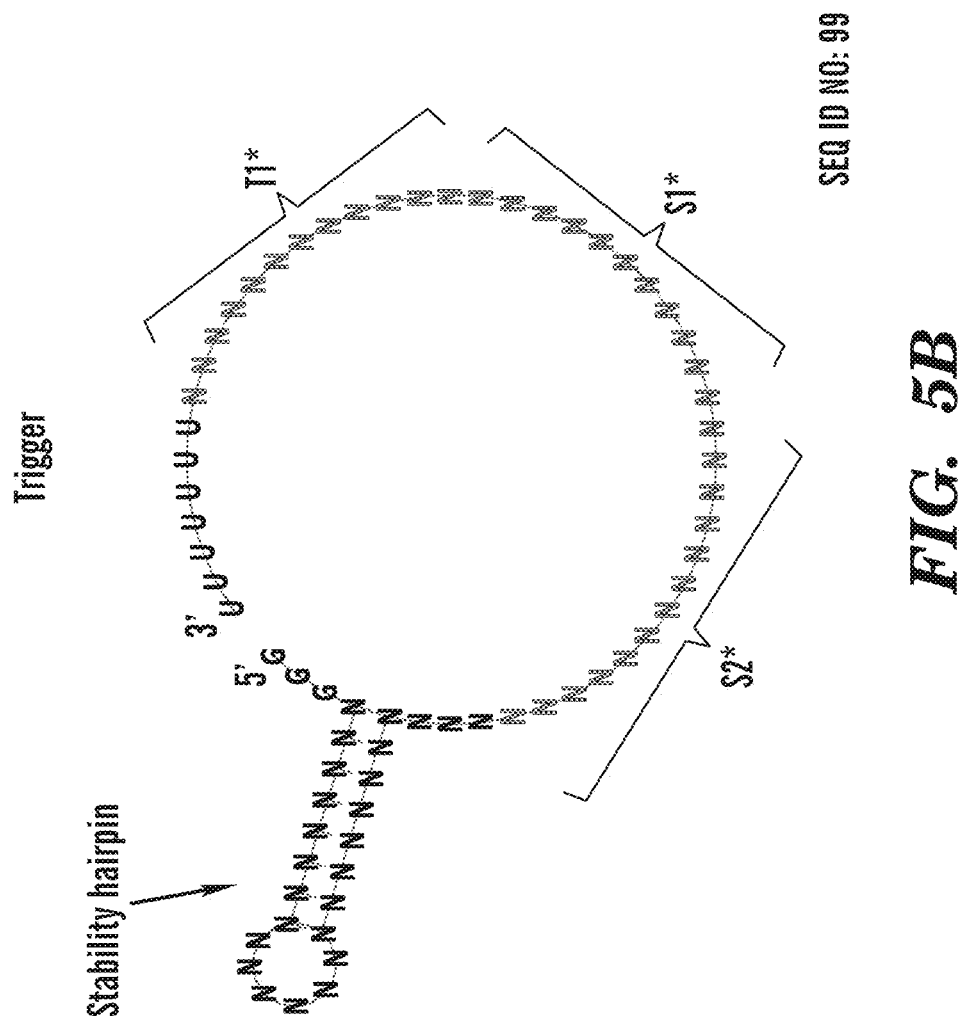
Figure 5C:
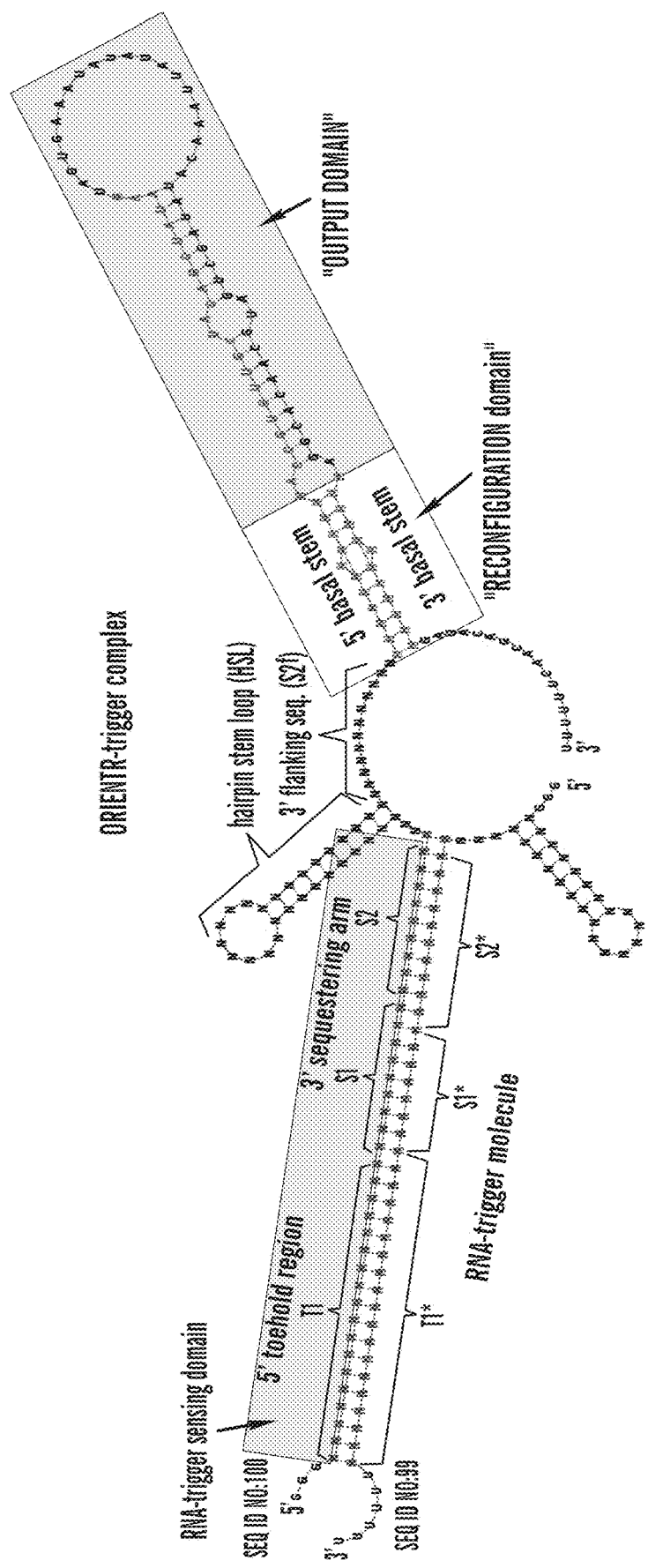

As disclosed herein, and referring to FIG. 5A and FIG. 5C, the ORIENTR adopts different RNA-based hairpin structures in its secondary structure conformation, which in term determine if Drosha can access the output domain and process miRNA.

Referring to FIG. 1C and FIG. 5A, and without wishing to be bound by theory, in the absence of a RNA-trigger molecule, the ORIENTR is in an INACTIVE configuration (e.g., ORIENTR-OFF) and forms a first RNA-hairpin referred to as a "sequestering-loop domain" that prevents Drosha acquisition and processing a second RNA-hairpin comprising an output domain. Drosha acquisition is prevented as the sequestering-loop domain sequesters a 5' basal stem sequence that would otherwise form half of the basal stem of a pri-miRNA scaffold that is a necessary part of a typical microprocessor substrate RNA, as explained in the Examples and below.

In another embodiment, referring to FIG. 1C and FIG. 5C, and without wishing to be bound by theory, in the presence of a RNA-trigger molecule, the ORIENTR forms a ORIENTR-trigger complex and the ORIENTR reconfigures into an ACTIVE configuration (e.g., ORIENTR-ON) due to the binding of the cognate RNA-trigger to the toehold domain, and also recruiting the binding to 3' sequestering arm. In some embodiments, the recruitment of 3' sequestering arm by the cognate RNA-trigger occurs through toehold-mediated strand displacement, which disrupts the first sequestering-loop domain to release the sequestered 5' basal stem sequence. The released 5' basal stem sequence then forms a RNA-duplex with a 3' basal stem sequence to form a reconfiguration domain. The reconfiguration domain forms the base stem of the RNA-hairpin of output domain, such that the reconfiguration domain and output domain forms a pri-miRNA scaffold which activates Drosha recognition and initiates miRNA biogenesis and processing of pri-miRNA to pre-miRNA and generation of mature functional miRNA as the output.

Importantly, as the binding of the RNA-trigger with the ORIENTR results in structural refolding of the ORIENTR sequestering-loop domain (i.e., disassembly of the sequestering domain) and results in the structural refolding of the reconfiguration domain, it is independent of the output domain comprising the miRNA-encoding region, the signal for inducing miRNA induction is decoupled from the output sequence. That is, as the miRNA-encoding region in the output domain is not involved in the secondary structure reconfiguration of the ORIENTR when the RNA-trigger is present, it enables the ORIENTR to be designed to be specific to any desired cognate RNA-trigger molecule.

Figure 1B:
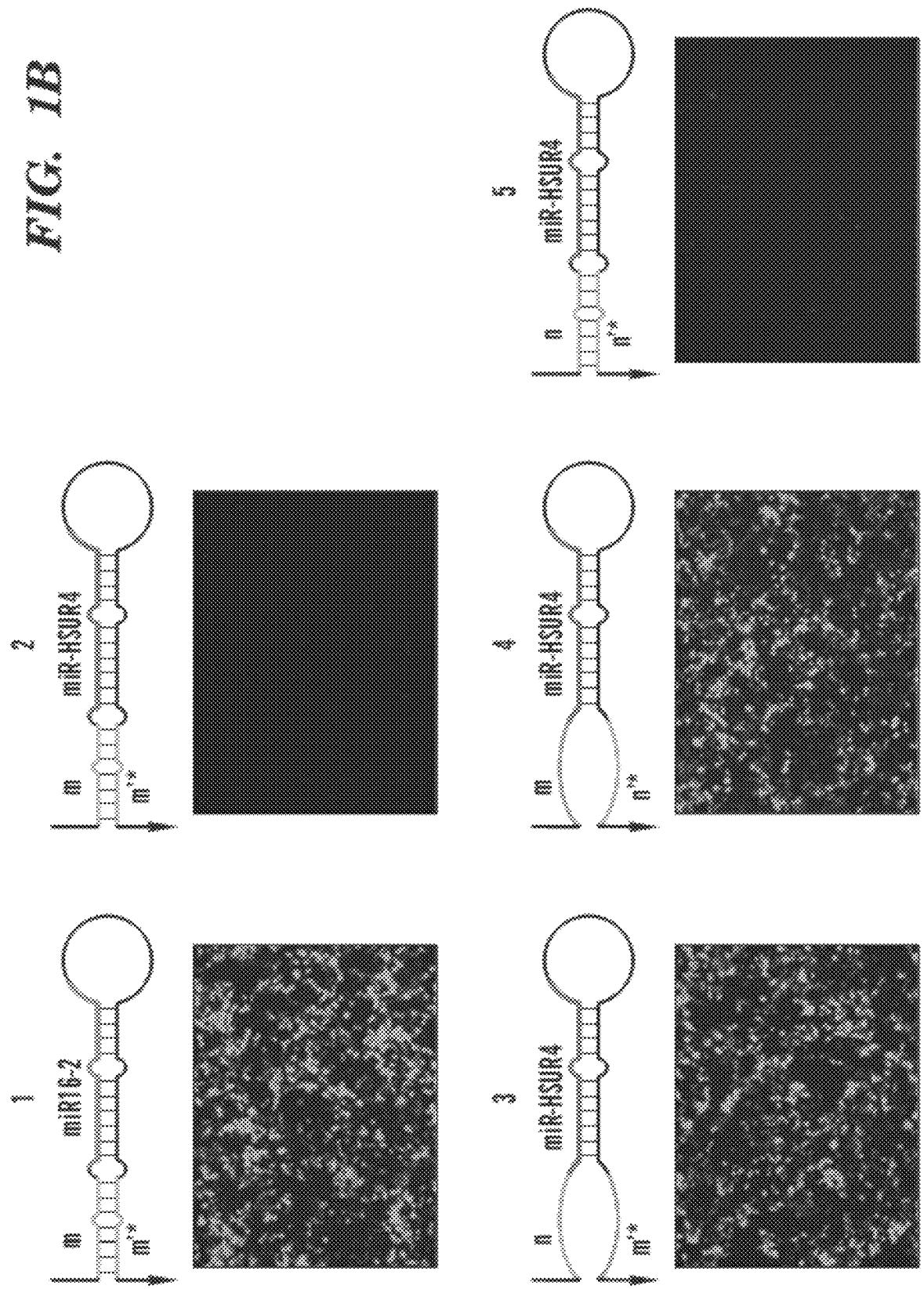
Figure 1C:
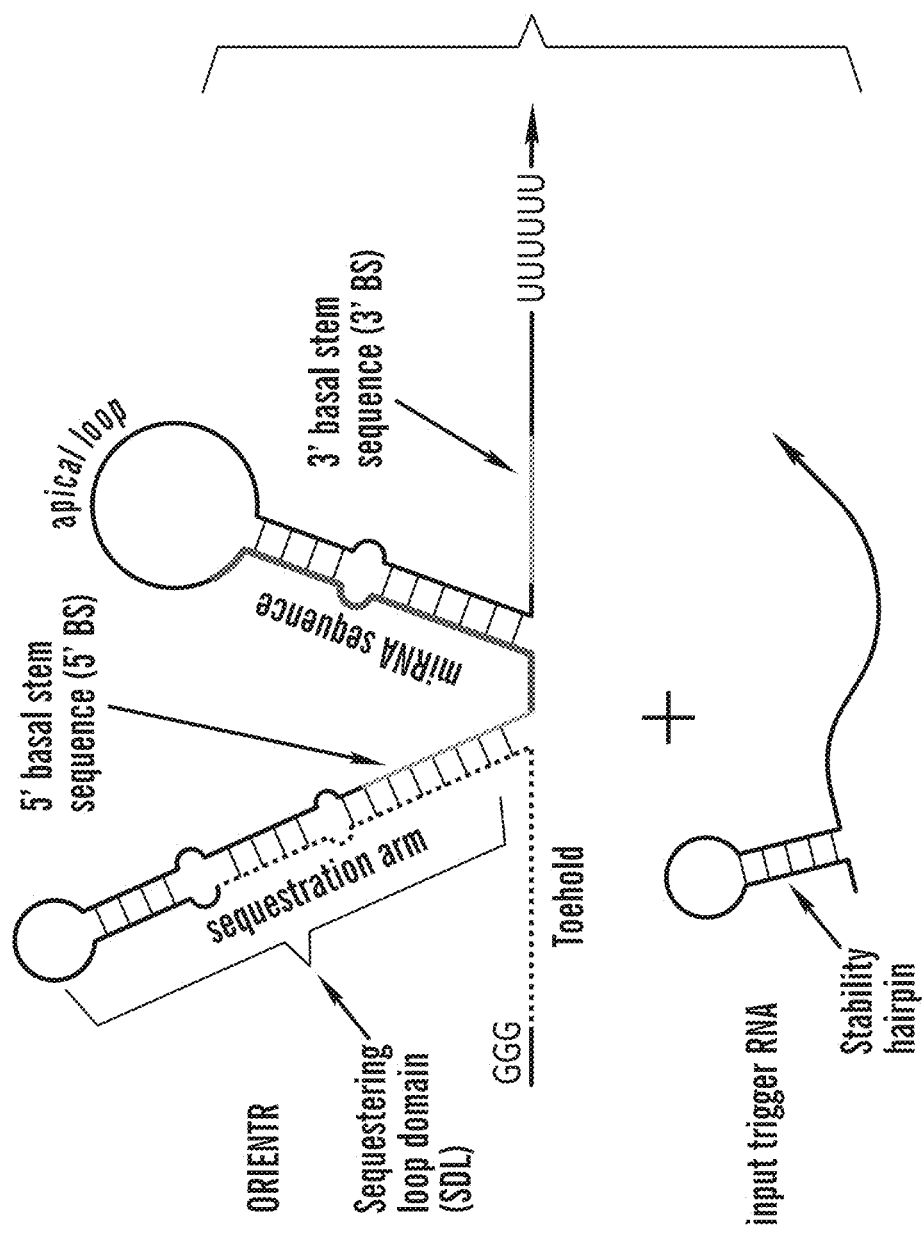
Figure 1C:
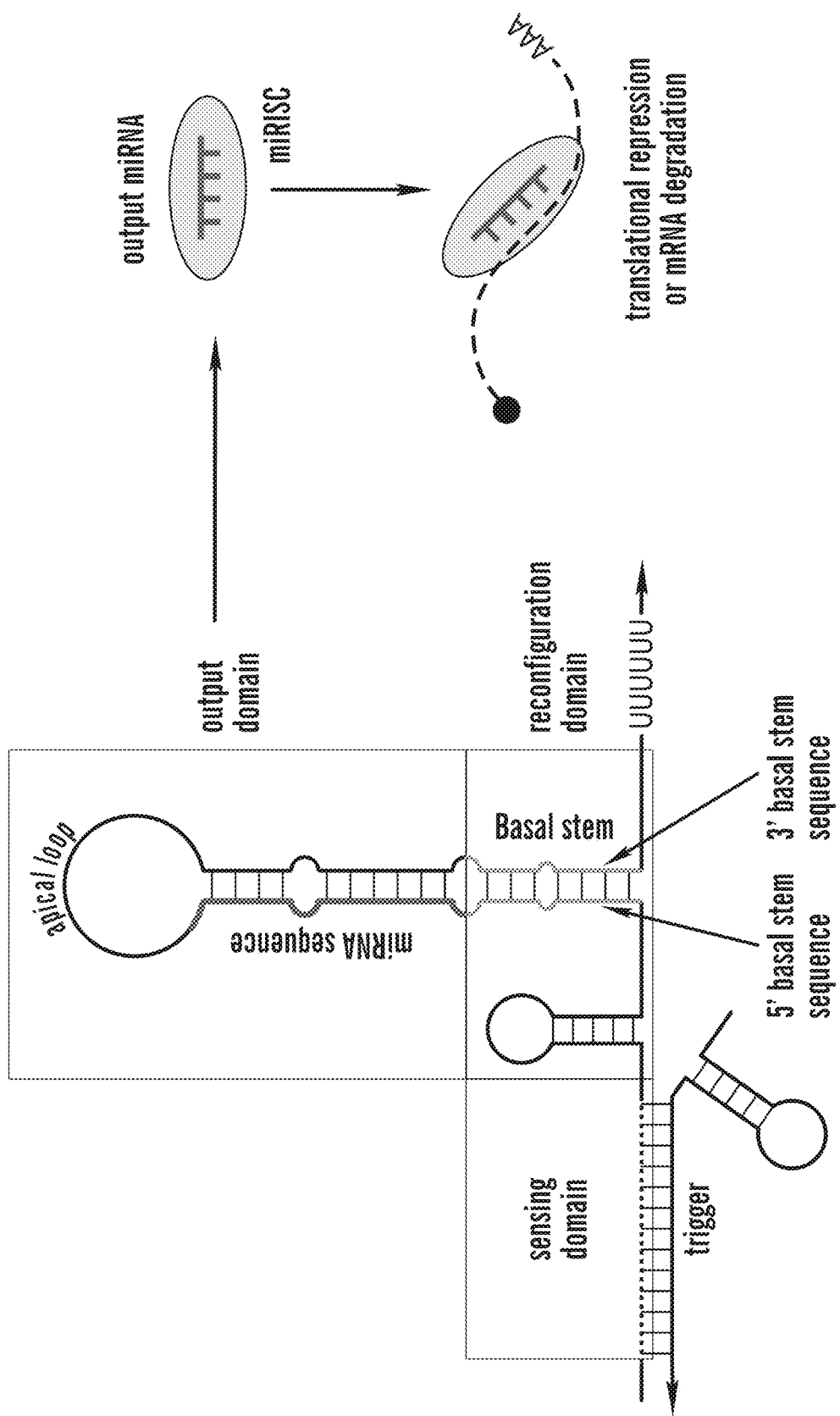
Figure 2A:
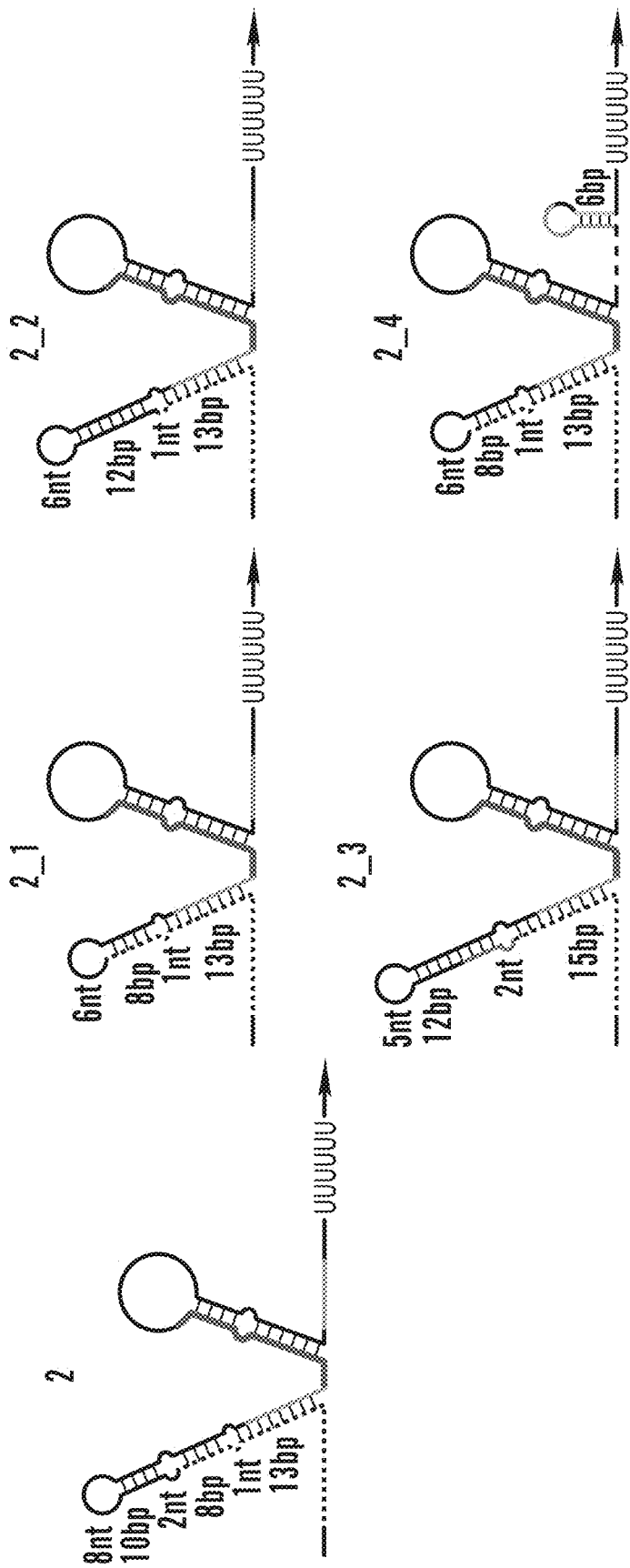
FIG. 2A-2E shows optimization and implementing an orthogonal ORIENTR library with lower leakage via secondary structure tuning.
Figure 2C:
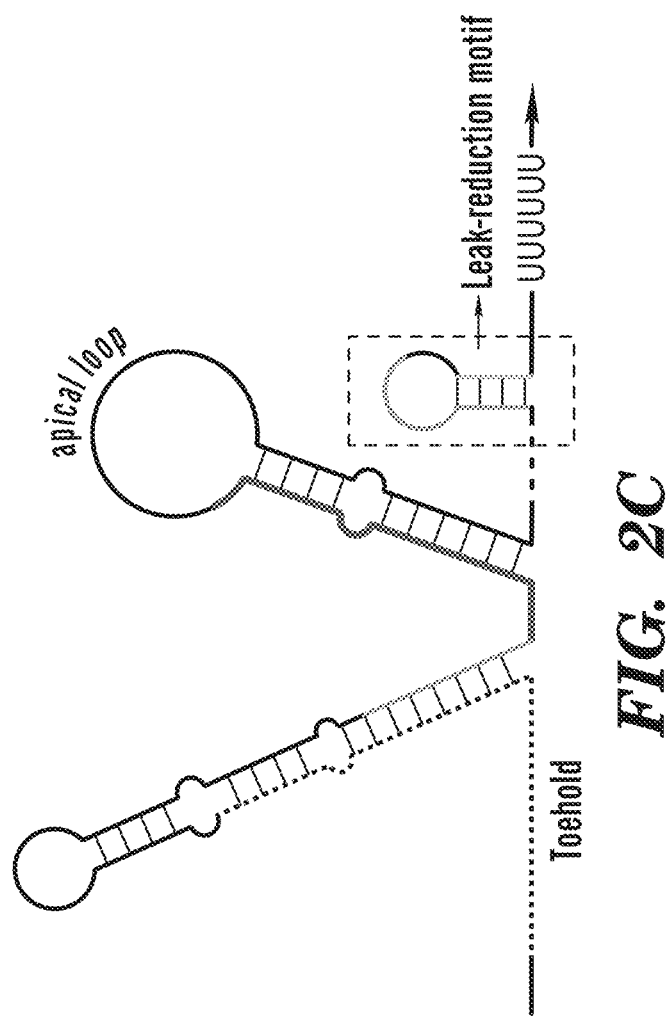
Figures 3A, 3B:
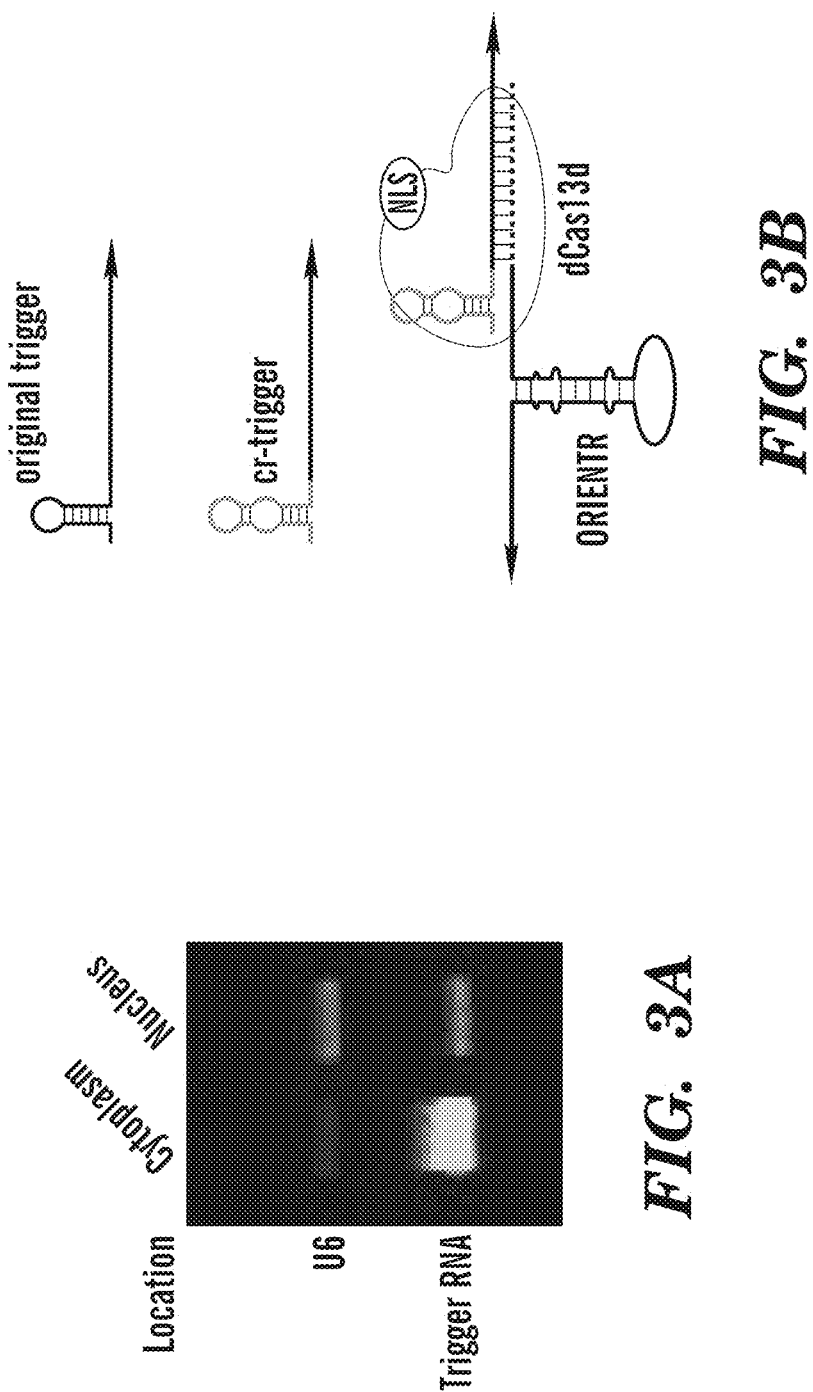
FIGS. 3A-3C show optimization and enhancing ORIENTR dynamic range using dCas13d.
Figure 3C:
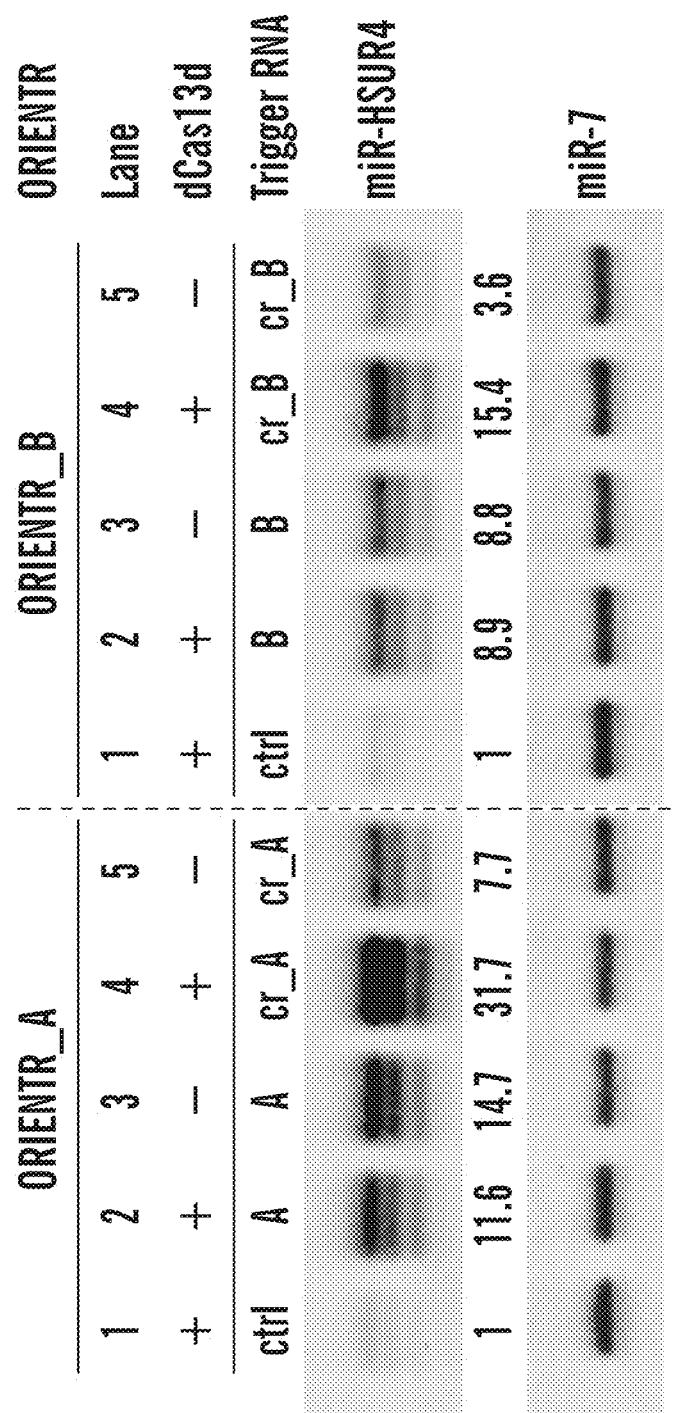

As described in the paragraphs that follow and the Examples, the inventors engineered multiple ORIENTR constructs comprising different sequestering RNA-hairpin structures, including but not limited to varying in length and position of 3' sequestering arm and 5' basal stem sequences (see FIG. 1B and FIG. 2A, as well as presence of a leak-reduction hairpin to optimize RNA-trigger induced miRNA bioprocessing (see, e.g., FIG. 2C), as well as optimizing RNA-trigger constructs including but not limited to (i) using a deactivated CRISPR nuclease dCas13d to facilitate RNA-RNA interaction and (ii) nuclear localization for improved performance (see, e.g., FIG. 3B).

In some embodiments, a ORIENTR as disclosed herein can comprise one or more chemical modifications that confer resistance to nuclease degradation.

One aspect as disclosed herein, relates to an inducible polynucleotide construct that serves as a riboregulator, that can be reconfigured from an inactive configuration into an active configuration by such that the secondary structure forms a correct pri-miRNA scaffold that can be processed by microprocessor. Referring to FIG. 5A-C, in some embodiments the construct, referred to herein as a ORIENTR construct, comprising, in a 5' to 3' orientation: (a) a RNA-trigger sensing domain comprising a 5' toehold region and a 3' sequestering arm region, wherein at least a region portion of the 5' toehold region and 3' sequestering sequence is complementary to an input trigger RNA sequence; (b) a loop, which in some embodiments, can be configured as a hairpin-stem loop (HSL), (c) a 3' flanking sequence (S2$^f$) which is complementary to a 3' portion (S2) of 3' sequestering arm region, (d) a 5' basal stem sequence, (e) an output domain comprising a RNAi hairpin, which in some embodiments is a pri-miRNA duplex sequence, comprising (i) a guide strand sequence targeting a nucleic acid of interest, (ii) an apical loop sequence, and (iii) a passenger strand sequence complementary to the guide strand sequence, and (f) a 3' basal stem sequence which can complementary base pair with 5' basal sequence, and (g) 5' spacer sequence, and optionally a RNA terminator sequence, e.g., a poly U sequence, where the ORIENTR inducible polynucleotide construct is configured such that:

in the absence of an input trigger RNA sequence, the inducible polynucleotide construct is in an inactive configuration (ORIENTR-OFF) configuration, comprising a (i) a sequestering loop domain (SLD), and a (ii) an output domain which comprises an inactive RNAi duplex, e.g., an inactive pri-miRNA duplex, where the sequestering loop domain (SLD) is configured such that (i) a 5' portion (S1) of 3' sequestering arm region forms a RNA duplex with 5' basal stem and (ii) a 3' portion of the 3' sequestering sequence (S2) forms a duplex with 3' flanking sequence, and (iii) terminates with a loop sequence at end, where the loop can in some embodiments, be configured as a hairpin-stem loop (HSL) terminates the RNA duplex, such that 5' basal stem sequence of the ORIENTR is not in a RNA duplex with 3' basal stem sequence, and the RNAi hairpin (e.g., the pri-miRNA duplex) in the output domain comprising the guide strand and passenger strand sequence connected via an apical loop sequence cannot be processed because it is in the incorrect scaffold configuration (i.e., without a basal stem structure) to be recognized and processed by Drosha, and where in the presence of an input trigger RNA sequence, the inducible polynucleotide construct is in an active pri-miRNA configuration (ORIENTR-ON configuration), wherein 5' toehold region and the S1 and S2 regions of 3' sequestering arm sequence of the RNA-trigger sensing domain form a RNA duplex with the input trigger RNA sequence, releasing 5' basal stem sequence therefore allowing the 5' basal stem sequence and 3' basal stem sequence form an imperfect RNA duplex that functions as a basal stem (i.e., as a reconfiguration domain), therefore enabling the downstream RNAi duplex in the output domain (comprising the guide sequence and passenger sequence) to correctly form a pre-miRNA scaffold that can be recognized by Drosha.

In some embodiments, 3' basal stem sequence is optionally configured in part of a leak-reduction motif, (also referred to herein as leak-prevention loop). In some embodiments, an exemplary leak reduction motif comprises a small hairpin, the small hairpin comprising a portion of 3' basal stem sequence, a loop, and a nucleic acid sequence that is complementary to at least a portion of 3' basal stem sequence. In some embodiments, and without wishing to be bound by theory, a leak-reduction motif or leak-prevention motif serves to occlude a 3' portion of 3' basal stem sequence, there a 3' portion of the 3' basal stem sequence can complementary base pair with a leak-prevention sequence, and the remaining 5' portion of 3' basal stem sequence is single stranded and available for complementary base pairing with 5' basal sequence once 5' basal stem sequence is released from the sequestering loop domain in the presence of a RNA-trigger as disclosed herein (e.g., therefore enabling 3' basal stem sequence and 5'-basal stem to forming the reconfiguration domain for an ORIENTR-ON configuration).

In some embodiments, an input trigger RNA sequence is a synthetic RNA sequence. In some embodiments, an input trigger RNA sequence is an endogenous RNA sequence. In some embodiments, the input trigger RNA sequence is a tissue-specific or cycle-dependent RNA sequence. In some embodiments, the 5' basal stem sequence and 3' basal stem sequence are each 11bp in length. In some embodiments, the 3' sequestering arm region is between 13-19 bp.

In some embodiments, an ORIENTR riboregulator as disclosed herein can be configured where the elements are in a reverse order, e.g., a mirror image of the ORIENTR shown in FIG. 5A, such that the toehold domain is located on 3' of the ORIENTR molecule. In some embodiments, such a reverse or mirror ORIENTR (referred to as ORIENTR*) comprises the following:

A nucleic acid construct comprising an Orthogonal RNA Interference induced by Trigger RNA (ORIENTR*) molecule, wherein the ORIENTR* is a mirror image the ORIENTR molecule shown in FIG. 1C or FIG. 5A, and comprises in a 3' to 5' order:
(i) a single stranded 3' toehold domain (T1), (ii) a fully or partially double-stranded RNA sequestering loop domain (SLD) comprising:

(a) a 5' sequestering arm sequence, comprising a S1 and S2 region,
(b) a loop sequence (or optionally, a hairpin-stem loop domain, where the hairpin-stem loop comprise
(c) 5' flanking sequence (S2'), wherein 5' flanking sequence forms a RNA duplex with a S2 region of 5' sequestering arm,
(c) a 3' basal stem sequence (3'-BS), wherein 3' basal stem sequence forms a RNA duplex with a the S2 region of 5' sequestering arm sequence,
(d) an output domain, the output domain comprising a fully or partially double-stranded RNAi hairpin (e.g., a pri-miRNA RNA hairpin domain), comprising (i) a passenger strand sequence to the guide sequence, (ii) a loop sequence (e.g., an apical loop) and (iii) a guide strand sequence targeting a nucleic acid of interest, and
(e) a 5' basal stem sequence, capable of complementary base pairing with 3' basal stem sequence to form a basal stem structure that is recognizable and can be bound Drosha.

In some embodiments, a ORIENTR* riboregulator (i.e., a reverse or mirror image ORIENTR to the ORIENTR shown in FIG. 5A) can be configured in an active configuration (i.e., ORIENTR*-ON) when it is in a complex with a RNA-trigger. In some embodiments, when an ORIENTR* in an ORIENTR*-ON configuration in the presence of a RNA trigger (i.e., ORIENTR* is present as a ORIENTR*-RNA trigger complex), it can comprise the following:

A nucleic acid construct comprising an ORIENTR*, wherein in the presence of a RNA-trigger sequence, the ORIENTR* molecule is reconfigured to comprise a secondary structure, in a 3' to 5' order:
a. a RNA duplex comprising 3' toehold domain (T1) and S1 and S2 regions of 5' sequestering arm duplexed with a cognate RNA sequence of a RNA-trigger sequence,
b. a single stranded 5' flanking sequence (S2'), and
c. a pri-miRNA scaffold comprising a fully or partially double stranded RNA duplex comprising, in a 3' to 5' order:
  i. 3' basal stem (3'-BS) sequence,
  ii. the output domain, the output domain comprising a fully or partially double-stranded RNAi hairpin, comprising (i) the passenger strand sequence to the guide (ii) a loop sequence (e.g., an apical loop), and (iii) a guide strand sequence to a target nucleic acid of interest, and
  iii. 5' basal stem (5'-BS) sequence,
wherein 3' basal stem sequence and 5' basal stem sequence exist in a RNA-duplex that serves as a basal stem structure that can be recognized and bound by Drosha.

As an exemplary illustration, an ORIENTR of FIG. 5A can change in configuration from an inactive to an inactive configuration as shown in FIG. 5C is outlined in FIG. 9.

In contrast to other RNA riboregulators, a ORIENTR as disclosed herein does not sequester the Microprocessor substrate RNA (e.g., does not sequester the pri-miRNA substrate), rather, an ORIENTR, in the absence of a RNA-trigger, sequesters a 5' basal stem sequence, therefore preventing it from forming an imperfect 11bp basal stem with 3' basal stem sequence (i.e., the reconfiguration domain), which together serves as a molecular ruler to direct Drosha cleavage, thus preventing processing of the pri-miRNA structure into a 5p-miRNA. The respective lengths of the ORIENTR toehold, 3' sequestering arm sequence, the optional hairpin-stem domain, 3' flanking sequence can be changed to a large extent without affecting the performance of the ORIENTR as will be detailed below. In addition, the 3' sequestering-loop domain (SLD) can retain its repression efficiency even if it contains a number of bulges or mispaired bases. In some embodiments, a bulge can be symmetrical, or asymmetrical (e.g., 1nt on one side, and 2 nt on the other side). In principle, the tolerance of bulges enables arbitrary RNA-trigger sequences, including endogenous RNAs, to act as input RNAs into the ORIENTR, although other criteria such as high secondary structure can affect the response of the ORIENTR regulator.

In some embodiments, an exemplary, non-limiting, class of ORIENTR riboregulator has design parameters shown in FIG. 5A. Such an exemplary ORIENTR of this class possesses a hairpin-stem loop, and a S2 sequence and a 3' flanking sequence. However, in some embodiments, a hairpin-stem loop (HSL) is not present in an ORIENTR, as disclosed below. An exemplary ORIENTR shown in FIG. 5A comprises (i) a 5' toehold domain that is between 9nt and ≥30-nucleotides (nts) long, (ii) a 3' sequestering arm sequence (S1 and S2), where the S1 sequence is between about 8-14nt, and typically is 1nt or more longer than the length of the 5'-basal sequence, and S2 is at least 1nt in length, where S2 can be, e.g., ≥1, e.g., between 1-15nt in length, a hairpin-stem loop (HSL) that is typically a double stranded stem of between 2-12nt, and a loop region between 3-10 bp, a 3' flanking sequence that is dependent on the pri-miRNA scaffold structure, e.g., can be 6-20nt in length, a 5'-basal stem sequence that is typically about 11nt long but can range between 8-14nt, a guide sequence that is between 20-22 bp, a apical loop that is between 3-23 bp long, a passenger strand that is between 20-22 bp long, a 3' basal strand sequence that is typically about 11nt but can range between 8-14nt in length depending on the length of the corresponding 5' basal stem sequence, a spacer that is variable length, e.g., 5-30 bp long and a 3' RNA pol III termination sequence.

An exemplary ORIENTR shown in FIG. 5A comprises (i) a 5' toehold domain that is about 12-nucleotides (nts) long, (ii) a 3' sequestering arm sequence (S1 and S2) that is ~22 nt, a hairpin-stem loop (HSL) that has ~9-12 bp stem and a 8nt loop, a 3' flanking sequence that is 8-10 nt long, a 5'-basal stem sequence that is about 1 1nt long, a guide sequence that is ~20 nt, a apical loop that is ~23 nt long, a passenger strand that is 20-21 nt long, a 3' basal strand sequence that is about 11bp, a spacer that is ~12nt long and a 3' RNA pol III termination sequence.

It is to be understood that the embodiment illustrated in FIG. 5A is non-limiting and that other ORIENTRs having differing lengths and functions of each element are contemplated and encompassed by the invention. Thus, the length of the toehold domain, 3' sequestering arm sequences (S1 and S2), the HSL, 3' flanking sequence, as well as the duplex regions within the stem domain, and the number of bulges may differ in length from the embodiment shown in FIG. 5A.

Exemplary components of the ORIENTR molecule are as follows:
A. RNA-Trigger Sensing Domain; 5' Toehold Region and 3' Sequestering Arm Sequence In some embodiments, and referring to FIG. 1C, an ORIENTR comprises a RNA-sensing domain, which comprises a 5' toehold region (T1) and a 3' sequestering arm sequence (S1, S2).
(i) 5' Toehold Region.

In an ORIENTR as disclosed herein, the interaction between the toehold domain in the ORIENTR molecule and the RNA-trigger (e.g., trans-RNA) species is mediated through a single-stranded RNA domain that is located to the 5' end of the ORIENTR molecule. This domain, which is referred to as the toehold domain, provides the RNA-trigger with sufficient binding affinity to enable it to unwind the stem of 3' sequestering loop domain. The degree of complementarity between the RNA-trigger and the toehold domain may vary. It some embodiments, it is at least 60%, at least 70%, at least 80%, at least 90%, at least 95%, or 100%. In some embodiments, the toehold domain of the ORIENTR is single stranded and does not comprise secondary structure that would restrict or inhibit binding of a RNA-trigger as disclosed herein.

Accordingly, a 5' toehold region serves as a "trigger RNA docking site" and has a sequence that is complementary to a regulatory nucleic acid element (e.g., RNA-trigger RNA) to form a RNA duplex. Referring to FIGS. 1C, a 5' single-stranded region called a tohold is used to initiate a hybridization reaction with a trigger-RNA with the complementary sequence T1* to the T1 sequence (i.e. the toehold sequence) in the ORIENTR.

As used herein, the term "trigger RNA docking site" refers to a region of the ORIENTR that is configured to bind a target or "trigger" RNA, the binding of which initiates a conformational change in the secondary structure of the ORIENTR.

Referring to FIGS. 5A and 5C, when the cognate trigger RNA (T1*) binds to the single stranded toehold sequence (T1), the stem of 3' sequestering-loop domain will gradually unwind as the 3' sequestering arm sequence (S1) forms a duplex with the complementary S1* and S2* sequence of the RNA-trigger, therefore disrupting the sequestering-loop domain, and strand displacement of 5' basal stem (5'-BS) sequence. The newly freed 5' basal stem sequence is then able to reconfigure into a RNA-stem or stem-forming domain with 3' basal stem loop to form a reconfiguration domain.

In some embodiments, the toehold domain be complementary to a naturally occurring RNA sequence or complementary to a non-naturally occurring synthetic RNA sequence. In some embodiments, the toehold domain is complementary in sequence to a naturally occurring RNA. A naturally occurring RNA may be an RNA that is capable of being expressed from the cell of interest (e.g., from an endogenous gene locus), or is present in another organism, e.g., in some embodiments, a naturally occurring RNA can be a viral RNA. In some embodiments, the toehold domain is complementary in sequence to a non-naturally occurring RNA. A non-naturally occurring RNA can be a synthetic RNA, or may be an RNA that is not naturally expressed in a cell of interest (e.g., it is not expressed from an endogenous gene locus), and may instead be expressed from an exogenous nucleic acid introduced into the cell of interest. In some embodiments, a RNA trigger is an exogenous RNA, e.g., a RNA that has been inserted into the cell of interest but does not naturally occur in the cell. Some embodiments, such exogenous RNAs can be modified. e.g., a change in one or more nucleotides from the sequence that was the basis of the RNA, or the original source of RNA.

In some embodiments, 5' toehold sequence comprises between 9-50 nucleotides (nt). In some embodiments, a toehold domain of at least 6 nts in length is preferable for RNA-trigger initial binding. The toehold domain can therefore be 5, 6, 7, 8, 9, 10, 11, 12, 13, 14, 15, 16, 17, 18, 19, 20, or more than 20 nucleotides in length. Moreover, in some embodiments, a RNA-trigger need only unwind two-thirds of 3' sequestering loop domain, and thus 3' sequestering arm region (S1) and (S2) may be as small as 12 bps (e.g., for hybridization to at least 5'basal stem sequence). The 3' sequestering arm sequence (S1 and S2) may however be longer than 12 bps, including 13, 14, 15, 16, 17, 18, 19, 20, or more base pairs in length. Variations of OREINTRs are shown in FIG. 2A and are described in greater detail in the Examples.

In some embodiments, an ORIENTR toehold domain can vary from ~9 to >50 nt in length. In some embodiments, where the RNA-trigger comprises endogenous RNA, a toehold T1 sequence is between 30-90nt in length, e.g. can be at least 30, to at least 40, or at least 50, or at least about 60, or at least about 70 or more nucleotides in length. In some embodiments, a toehold sequence can be at least about 70, or at least about 75, or at least about 80, or at least about 85 or at least about 90 nucleotides in length.

(ii) 3' Sequestering Arm.

Referring to FIG. 5A, 3' sequestering arm sequence is a nucleic acid sequence that functions as a cis-repressive sequence to 5' basal stem sequence of the ORIENTR and a portion of the 3' sequestering arm (i.e., S1 as disclosed herein) can form, in the absence of a RNA-trigger, a fully or partially double-stranded stem forming domain with 5' basal stem (5'-BS) sequence. As shown in FIG. 5A, in some embodiments depending on the configuration of the sequestering-loop domain, 3' sequestering arm sequence can comprise a 5' region, referred to as S1, and a 3' region, referred to as S2. In some embodiments and in the absence of a RNA-trigger, the S1 region can form a fully or partially double-stranded stem forming domain with 5' basal stem (5'-BS) sequence, thus sequestering 5'-basal stem sequence from forming a double-stranded stem-domain with 3' basal stem sequence. In alternative embodiments, in the presence of a RNA-trigger, the S1 region can form a double-stranded duplex with S1* of the RNA-trigger molecule.

Referring to FIG. 5A, in some embodiments and in the absence of a RNA-trigger, the S2 region of 3' sequestering arm sequence can form a fully or partially double-stranded stem domain (i.e., a duplex) with 3' flanking sequence (referred to herein as "S2*") of ORIENTR.

In general, the length of 3' sequestering arm sequence depends on (i) the positioning of the cis-repressive sequence, e.g., 5' basal stem sequence, and (ii) the length of 3' flanking sequence. In some embodiments, as the length of 5' basal stem sequence can be 11bp, the region of the S1* is at least 11bp. In some embodiments, the length of the S1 and S2 of 3' sequestering arm has a length of 21 nucleotides, but in other cases will be shorter or longer than 21 nucleotides.

Figure 2B:
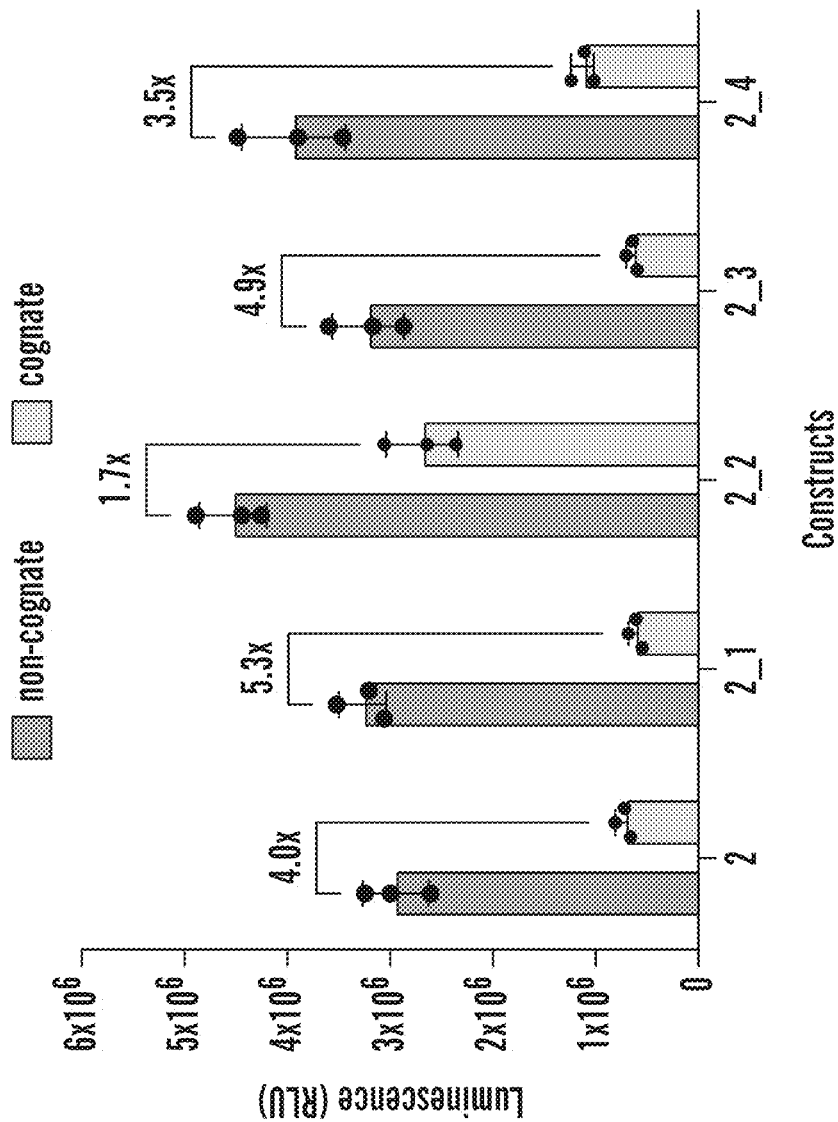

As shown in the Examples and in FIG. 2B, in the absence of a RNA-trigger, the secondary structure, or configuration of the sequestering loop domain (SLD) of an ORIENTR comprising (i) a 3' sequestering arm (S1 and S2) and (ii) the downstream sequences (e.g., hairpin stem loop (optional) and/or 3' flanking sequence) can affect the signal leakage and sensitivity of the response to the RNA-trigger. Accordingly, it is envisioned that a person of ordinary skill in the art can tailor the lengths of the S1 and S2 regions in 3' sequestering arm region, and also the downstream sequences (e.g., hairpin stem loop and/or 3' flanking sequences) to suit the sensitivity and specificity of the ORIENTR to the RNA-trigger for specific situations.

In some embodiments, the length of the S1 region in 3' sequestering arm sequence is at least 1, or at least 2 nt longer than 5' basal stem sequence. As an exemplary example, in some embodiments, if a 5' basal stem sequence is 11bp, the S1 region is 13nt in length. In some embodiments, if 5' basal stem is between 8nt and 14nt, the S1 sequence can be between 9-16nt, for example, the S1 length can be 1nt or 2nt or 3nt longer than 5' basal stem sequence in the ORIENTR.

In some embodiments, the length of the S2 region in 3' sequestering arm sequence is at least 1 nt based on thermodynamic considerations. In some embodiments, the length of the S2 sequence is between 1-15nt in length, or longer than 15 bp. In some embodiments, the length of the S2 region can be dependent on the length of the S1' sequence. In addition, the length of the S2 region can be dependent on the number of mismatches between S1 and S1* in the RNA-trigger sequence, or at least 2 nt longer than 5' basal stem sequence.

In some embodiments, the S1 and/or S2 regions of 3' sequestering arm can be complementary to a naturally occurring RNA sequence or complementary to a non-naturally occurring RNA sequence or synthetic RNA sequence. Without being limited to theory, if S1 is complementary (i.e., an antisense strand) to a part of a RNA-trigger, then 5' basal sequence would, in general, also be a sense strand to the same portion of the RNA-trigger (i.e., complementary to the S1), and in turn, 3' basal sequence would, in principal, be complementary to 5'-BS sequence (i.e., antisense to the naturally occurring RNA sequence). It is generally understood that the S1 sequence on 3' sequestering arm and S1* portion on the RNA-trigger does not need to be 100% complementary, and it is envisioned that in some embodiments, there are be one or more mismatches between the S1 and S1* sequences. Similarly, it is understood that the S1 sequence on 3' sequestering arm and 5' basal stem sequence does not need to be 100% complementary, and it is envisioned that in some embodiments, there are be one or more mismatches between the S1 and 5' basal stem sequence.

In some embodiments, the length of the S2 region of 3' sequestering arm is dependent in part, on the length of the RNA-trigger, in particular the length of the S2* region of the RNA-trigger. Therefore, in some embodiments, the length of 3' sequestering arm sequence can vary, depending on the length of the basal stem (approx. 11bp) to length of basal stem+15nt, depending on the degree of repression and likelihood of activation desired.

In some embodiments, depending on the design and configuration of the sequestering-loop domain (see, e.g., FIG. 2A), the sequestering arm region only comprises a S1 region, and in the absence of the RNA-trigger, the entire length of 3' sequestering arm sequence S1 can form a fully or partially double-stranded stem forming domain with 5' basal stem sequence. Alternatively, in such embodiments, in the presence of a RNA-trigger, the entire length of the S1 region can form a double stranded duplex with a S1* portion of the RNA-trigger, where the RNA-trigger can optionally have a T1* and S1* regions only.

In certain embodiments, the sequence of the S1 can be adjusted to achieve optimal levels of hybridization with 5'-BS sequences. The optimal level of hybridization in a given situation (e.g., cell) may not necessarily reflect the maximum possible hybridization. Mismatch or wobble base-pairings, substituting G-C with A-U base pairing or other modified base-pairing may be used to fine-tune the optimal/desired level of hybridization. Similarity, in some embodiments, optimal levels of hybridization may also be achieved by adjusting the sequences of S2 to achieve optimal (again, not necessarily the maximum) level of hybridization with 3' flanking sequence.

B. Loop Structure

In some embodiments, the ORIENTR comprises a loop structure located between 3' of the 3' sequestering arm, and 5' of 3' flanking sequence. In some embodiments, the loop is located 3' of the S2 region of 3' sequestering arm region and 5' of 3' flanking sequence. An exemplary ORIENTR in the ORIENTR-OFF configuration with a loop structure is shown in FIG. 2A (ORIENTR 2_1). In such an embodiment, in an ORIENTR-OFF configuration (i.e., the absence of a RNA-trigger), the loop is part of the sequestering-loop domain (SLD) and forms the top part SLD. In some embodiments, the loop region of at least 5nt, e.g., a loop can comprise, e.g., 5, 6, 7, 8, 9, 10 or more than 10nt. In some embodiments, in an ORIENTR-ON configuration the loop region dissipates or remains as a small loop located between the RNA-sensing domain and 3' flanking sequence. In such embodiments, the loop in an ORIENTR-ON configuration is no longer part of a sequestering loop domain (SLD) (which has been unwound), and is flanked by the downstream 3' flanking sequence as single stranded sequence.

In some embodiments, the loop is part of a hairpin loop structure as disclosed herein in section II (C). Accordingly, in embodiments when the ORIENTR does not comprise a hairpin-stem loop, the loop structure is at least 5nt at the 5' end of 3' flanking sequence (S2+) which can forms a loop at the end of the sequestering-loop stem when a RNA trigger is absent (see ORIENTRs 2_1 and 2_4 in FIG. 2A). In some embodiments, exemplary loop sequences are disclosed in ORIENTRs 2_1 and 2_4 (see, e.g. FIG. 2A).

C. Hairpin-Stem Loop (HSL).

In some embodiments, the loop sequence of the ORIENTR can be configured as a hairpin-stem loop structure. Accordingly, in some embodiments an ORIENTR can optionally comprise a hairpin-stem loop (HSL) structure, (also referred to as a upper-stem loop structure), which can exist as part of the sequestering-loop domain when a RNA-trigger molecule is absent, or exists as a separate or independent hairpin structure when the ORIENTR is in a complex with a RNA-trigger and the RNA-trigger has disrupted the sequestering-loop domain.

Accordingly, in some embodiments, as shown in FIG. 1C, FIG. 2A (2), and FIG. 5A, the ORIENTR molecule comprises an hairpin-stem loop (HSL) (also referred to herein as a "upper-stem loop") located 3' of the S2 region of 3' sequestering arm region and 5' of 3' flanking sequence. As shown in FIG. 2A (2), in such an embodiment, in the absence of a RNA-trigger, an ORIENTR is configured such that the hairpin-stem loop is part of the sequestering-loop domain (SLD) and forms the top part of the stem of the SLD, and comprises a loop region of at least 5nt, e.g., a loop can comprise, e.g., 5, 6, 7, 8, 9, 10 or more than 10nt. In some embodiments, in the presence of a RNA-trigger, the hairpin-stem loop remains a stem-loop structure when the ORIENTR is in a complex with RNA trigger complex, however, it is no longer part of a sequestering loop domain (SLD) (which has been unwound), and it is flanked with single stranded flanking sequences, with 3' flanking sequence as single stranded sequence located 3' of the hairpin-stem loop.

It is envisioned that in embodiments when the ORIENTR does not comprise a hairpin-stem loop, rather, there is a loop structure that is at least 5nt at the 5' end of 3' flanking sequence (S2') which can forms a loop at the end of the sequestering-loop stem when a RNA trigger is absent (see ORIENTRs 2_1 and 2_4 in FIG. 2A).

In some embodiments, the hairpin-stem loop is about 21 nucleotides in length. In some embodiments, the hairpin-stem loop ranges in length from about 15-30 nucleotides.

D. 3' Flanking Sequence.

In some embodiments, 3' flanking sequence (referred to as S2$^f$) is located 3' of 3' sequestering arm sequence and is complementary in part, or fully, to the S2 region of 3' sequestering arm sequence and can, in the absence of a RNA-trigger, form a double-stranded stem with S2.

In some embodiments, the depending on the design and configuration of the sequestering-loop domain of the ORIENTR molecule (see, e.g., FIG. 2A), 3' flanking sequence comprises 5 nucleotides (6nt) or more than 5nt at 5' of the S2' sequence that can form a loop (e.g., see ORIENTR configurations 2_1 and 2_4 in FIG. 2A). For example, in some embodiments, in the absence of a RNA trigger, the sequestering-loop domain comprises; a lower double-stranded stem portion comprising the S1 and the sequestered 5'-BS sequence, and an upper stem-loop portion, where the upper-loop portion comprises S2 of 3' sequestering arm region duplexed with S2', where 3' flanking sequence comprises a of 6nt or more than 6nt, which is located 5' of the S2' sequence.

In some embodiments, when a RNA-trigger is absence and the ORIENTR is in an inactive confirmation, the S2 of 3' sequestering arm region and S2' of the 2'flanking sequence form a fully, or partially duplex stem. In some embodiments, S2 and S2' stem has a length of about 5-15 nucleotides, but in other cases will be shorter or longer than 15 nucleotides. The length of the S2-S2$^f$ stem of an ORIENTR in the inactive configuration can be measured from the first pair of complementary nucleotides to the last pair of complementary nucleotide bases, and includes mismatched bases (e.g., pairs other than AT, AU, GC), and includes nucleotides that form a bulge and/or nucleotides that form an inner loop.

As shown in FIG. 2C and FIG. 5A, a the S2 region and/or S2' sequence can comprise nucleotides such that a S2-S2' stem in a sequestering-loop domain can comprise one or more bulges. In some embodiments, the sequestering loop domain can comprise at least 2 bulges within the sequestering-loop domain: e.g., a single bulge located at or near the intersection of the S1 and S2 regions of 3' sequestering arm sequence (which corresponds to where 5' basal stem and 3' flanking region connect), and a bulge at, or around 3' end of the S2 region.

In some embodiments, the last two nucleotides at 3'-end of the S2$^f$ basal stem sequence are UG (see e.g. FIG. 1A). In alternative embodiments, the last two nucleotides at 3'-end of the S2$^f$ basal stem sequence are not UG. In some embodiments, the S2' sequence comprises a DGCR8 binding sequence. In some embodiments, the S2' sequence does not comprise a DGCR8 binding sequence.

An exemplary ORIETNR design is shown in FIG. 1C, however, it is envisioned that ORIENTRs as disclosed herein need not have this particular design. Alternative ORIENTR designs as disclosed herein and shown in FIG. 2A. It will be understood that the lengths of different domains (e.g., S1-5-BS stem, S2-S2f and hairpin-stem domain, as well as different output domains, spacers and toehold regions can all be modified in length and sequence); number and locations of bulges; relative positions of loop on the sequestering loop domain etc., and each can be modified to change the properties of the resulting ORIETNR. For example, modifications to the number of bulges can change the degree of binding of the Drosha and recognition by the Microprocessor of the ORIENTR when the RNA-trigger is present.

E. 5' Basal Stem (5'-BS) and 3' Basal Stem (3'-BS) Sequences

In some embodiments, 5' basal stem sequence and 3' basal stem sequence of an ORIENTR are complementary sequences. That is, in some embodiments, 5' basal stem is a sense strand, and 3' basal stem sequence is an imperfect reverse complement to 5' basal stem sequence. In some embodiments, 5' basal stem sequence is 11nt, or between 10nt and 15nt, and 3' basal stem sequence is the same length as that of 5'basal stem sequence, e.g., is 11nt, or between 10nt and 15nt corresponding to the cognate 5' basal stem sequence.

In some embodiments, 5' basal stem sequence and 3' basal stem sequence form a form double-stranded basal stem structure, herein referred to as a "reconfiguration domain" when the ORIENTR binds to a RNA-trigger as disclosed herein. In some embodiments, 5' basal stem sequence (5'-BS) is 100% complementary to 3'-basal stem sequence (3'-BS). In some embodiments, 5' basal stem sequence (5'-BS) may be less than 100% complementary to 3'-basal stem sequence (3'-BS), e.g., 5'-BS can be, e.g., at least 95%, or at least 96%, or at least 97%, or at least 98%, or at least 99%, or at least 99.5% complementary to 3'-basal stem sequence (3'-BS), and vice versa.

In some embodiments, as shown in FIG. 5C, a reconfiguration domain comprising the double stranded 5' basal stem and 3' basal stem sequences comprise at least one, or at least two bulges, and therefore can be an imperfect double stranded stem (e.g., see m and m*, and n and n* in FIG. 1B, where * designates an imperfect reverse complement). In some embodiments, at least one bulge is approximately in the middle of the reconfiguration domain, e.g., 7nt from the base of the double stranded basal stem (e.g., the 7th base pair beginning from the 5' end of 5' basal stem sequence). It is envisioned that the location of the first bulge can move up and down the 11bp basal stem structure, provided the basal-stem structure is still able to recruit Drosha and the microprocessor complex. In some embodiments, there is a second bulge at the end of the double-stranded basal stem, e.g., at 3' end of the 5' basal stem sequence (e.g., the 11bp of 5' basal stem sequence, and the first base pair of 3' basal stem sequence).

Figure 4A:
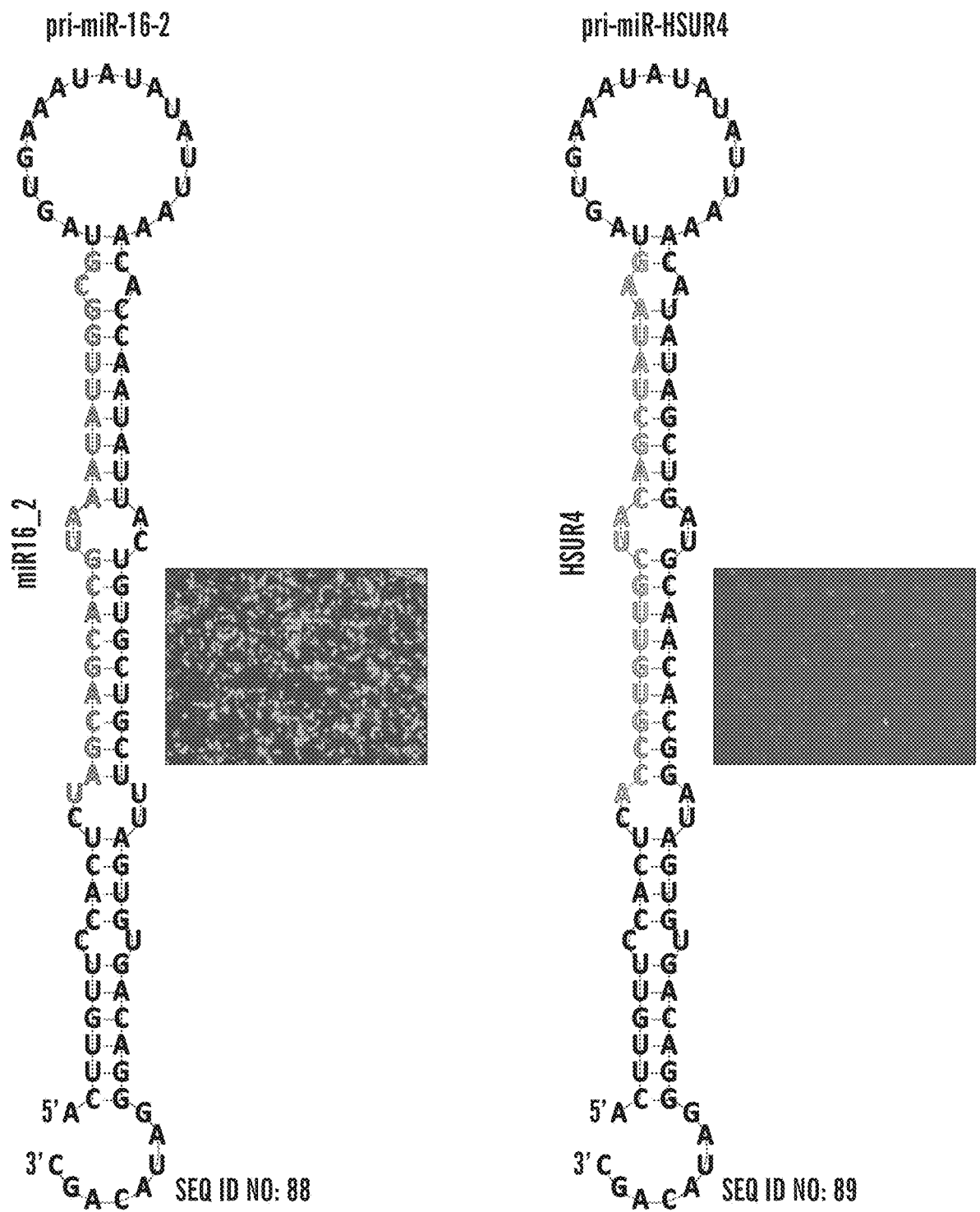
FIG. 4A-4C is a study of different pri-miRNA scaffolds.
Figure 4B:
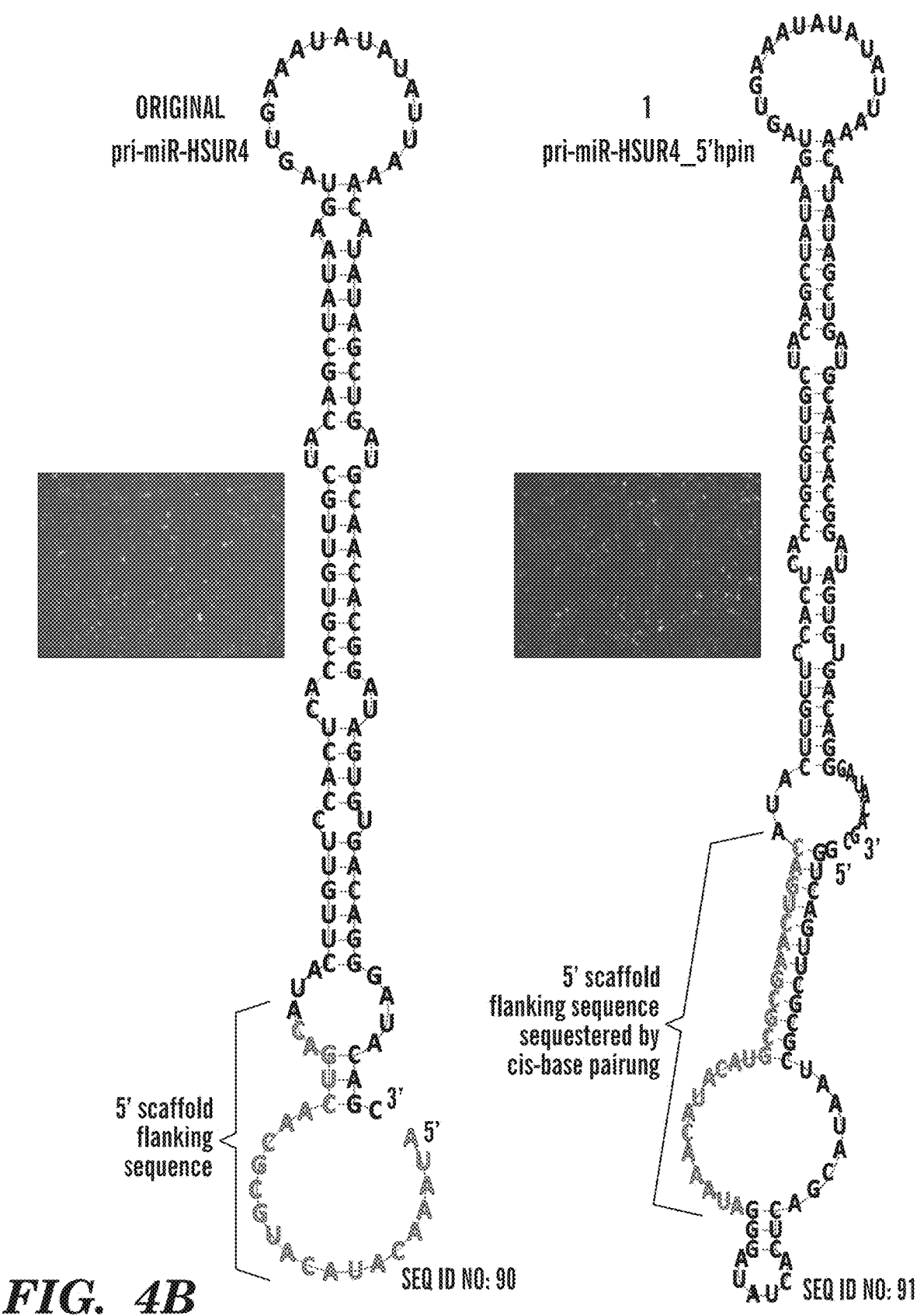
Figure 4B:
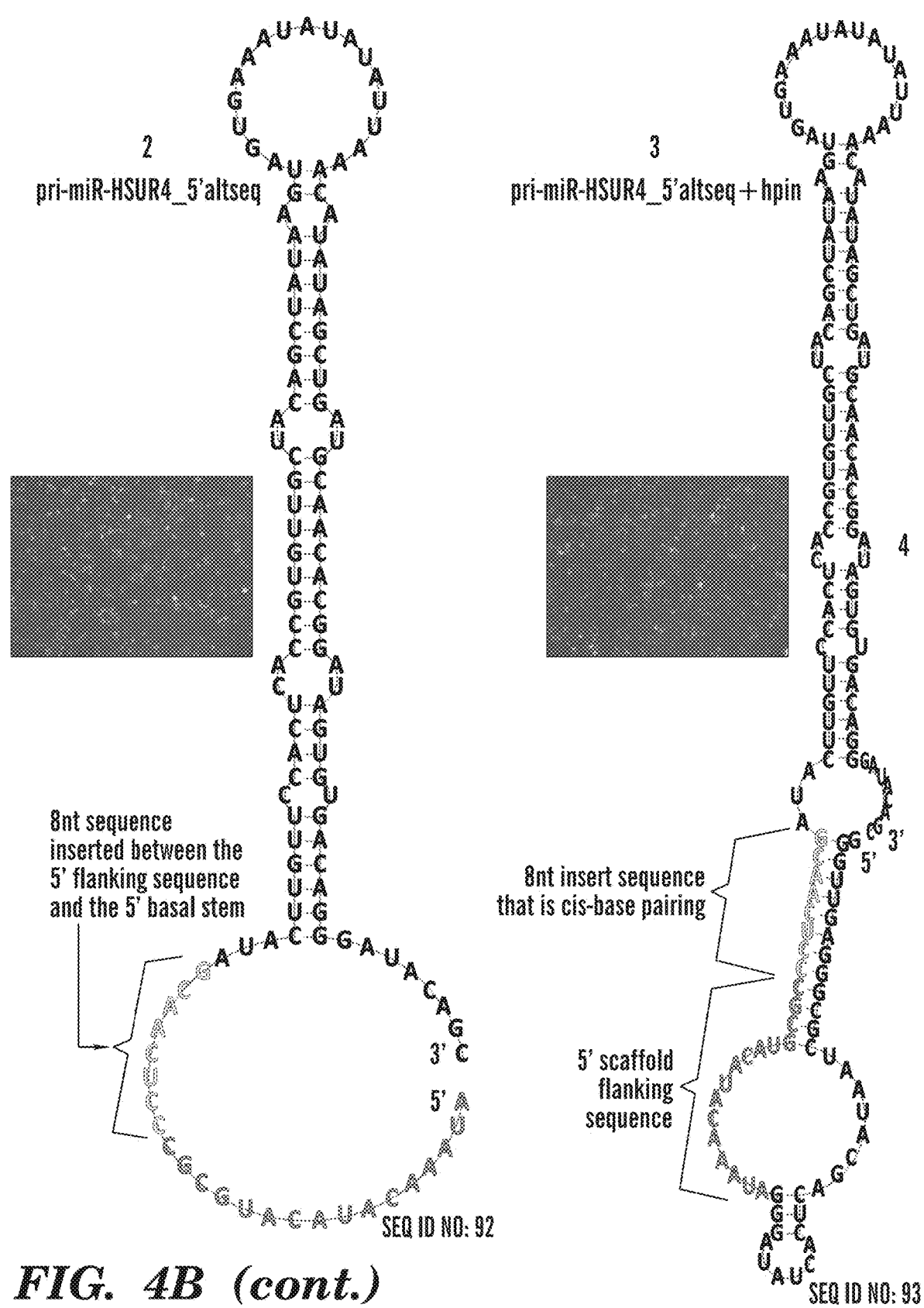
Figure 4C:
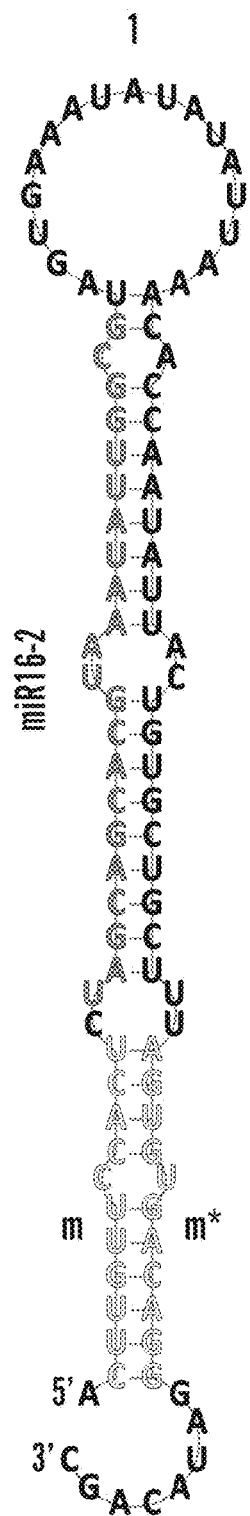
Figure 4C:
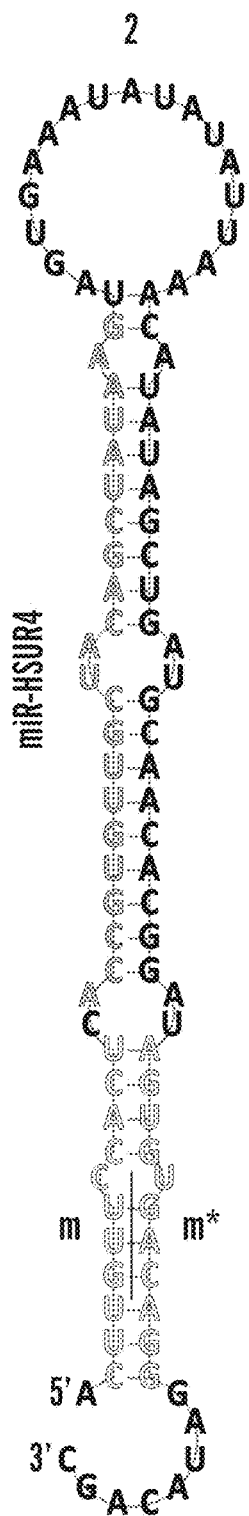
Figure 4C:
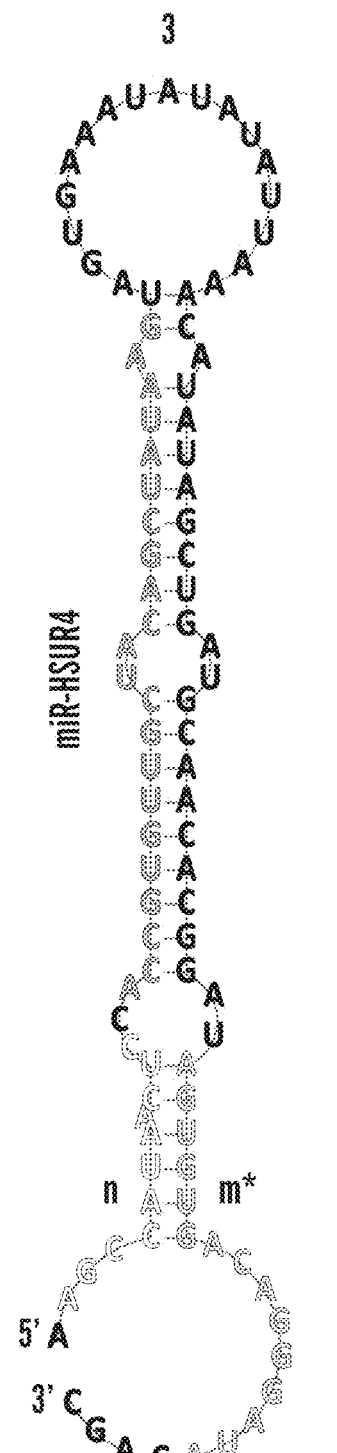
Figure 4C:
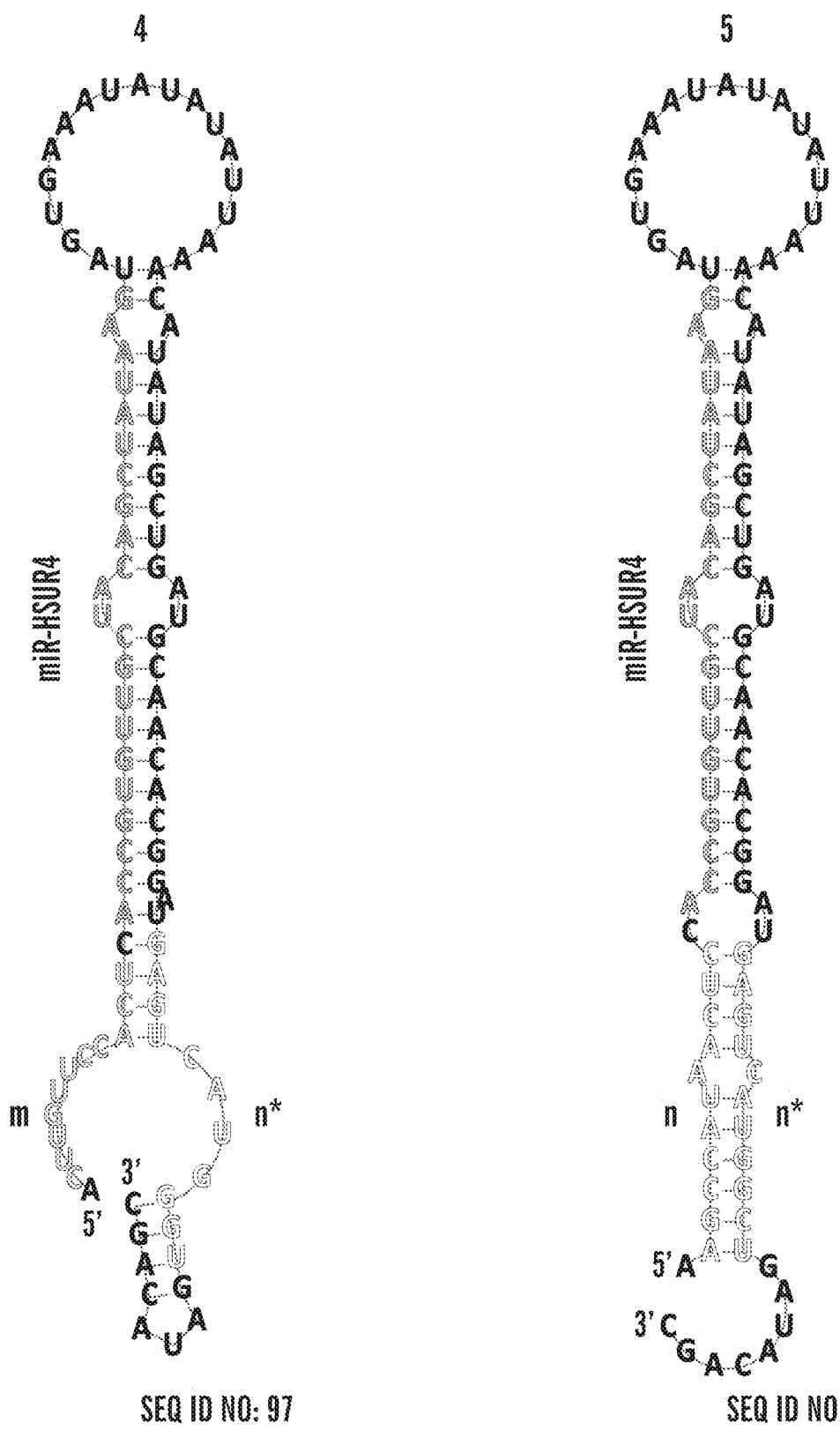

As disclosed herein the Examples and FIG. 1B (see panels 2 and 5), and in FIG. 4C, the specific sequences used for the 5-basal sequence (5-BS) and the 3-BS do not necessarily need to be conserved sequence specific to a specific pri-miRNA scaffold. Rather, as long as a 5'-BS sequence and a 3'-BS reverse complement sequence, upon complementary base pairing, form an imperfect 11bp stem domain, (i.e., the 11bp imperfect stem structure is conserved), any 5'-BS and 3'-BS sequence can be utilized in the ORIENTR as disclosed herein. This provides flexibility in the ORIENTR conditional pri-miRNA design. Moreover, it is envisioned that while the ORIENTR is designed to reconfigure to generate a pri-miRNA scaffold structure for processing into a single miRNA from the 5' arm of the hairpin of the output domain (to form a 5p-miRNA), it is envisioned that the output design of the ORIENTR, and/or 5'-basal stem sequences and 3'-basal stem sequence can be modified to form, in the presence to a RNA-trigger, the correct structural requirements of other pri-miRNA scaffolds.

In some embodiments, 5'-BS sequence is the reverse complement to S1 of 3' sequestering arm sequence. In some embodiments, 5'-BS sequence has a greater affinity for complementary base pairing with 3' basal stem sequence than complementary base pairing with S1. In some embodiments, a 5' basal stem sequence (5'-BS) has a weaker affinity for complementary base pairing with the S1 sequence and a stronger affinity for base pairing with 3'-BS sequence. In alternative embodiments, a 5' basal stem sequence (5'-BS) has a stronger affinity for complementary base pairing with the S1 sequence and a weaker affinity for base pairing with 3'-BS sequence. It is envisioned that the affinity for base pairing of 5'-BS sequence to the S1 sequence and 3'-BS sequence can be tailored and optimized by on of ordinary skill in the art to optimize the sensitivity and specificity of the ORIENTR to RNA-trigger mediated activation of miRNA biogenesis.

In some embodiments, a 5' basal stem sequence (5'-BS) is 100% complementary to the S1 sequence. In alternative embodiments, 5' basal stem sequence (5'-BS) may be less than 100% complementary to the S1, e.g., 5'-BS can be, e.g., less than about 95%, or about 96%, or about 97%, or about 98%, or about 99% complementary to the S1 sequence of 3' sequestering arm sequence.

In some embodiments, an exemplary 5' basal stem sequence comprises: 5'-CUUGUUCCACU-3' (SEQ ID NO: 1) (referred to as m), and its complementary 3' basal stem sequence is: 5'-AGUGUGACAGG-3' (SEQ ID) NO: 2) (referred to as m*), as shown in FIG. 4C (panel 2). In some embodiments, an exemplary 5' basal stem sequence comprises: 5'-AGCCAUAACUC-3' (SEQ ID NO: 3) (referred to as n), and its complementary 3' basal stem sequence is: 5'-GAGUCAUGGCU-3' (SEQ ID NO: 4) (referred to as n*), as shown in FIG. 4C (panel 5). In some embodiments, a 5'- and 3'-basal sequence pair can be selected from SEQ ID NO: 1 and SEQ ID NO: 2 or a nucleic acid sequence having at least 50%, at least 60%, at least 70%, at least 80%, at least 80%, or at least 85% or at least 90% sequence identity thereto. In some embodiments, a 5'- and 3'-basal sequence pair can be selected from SEQ ID NO: 3 and SEQ ID NO: 4, or a nucleic acid sequence having at least 50%, at least 60%, at least 70%, at least 80%, at least 80%, or at least 85% or at least 90% sequence identity thereto.

In some embodiments, when the ORIENTR is present in a complex with a RNA-trigger (e.g., ORIENTR-ON configuration), a basal stem formed by 5'- and 3'-basal sequences can optionally comprise one or more conserved sequence motifs for Drosha cleavage, such as, UG motif at the base of the basal stem, and/or a mismatched GHG (mGHG) motif in the basal stem. In alternative embodiments, the 5' basal stem and 3' basal stem sequence, when forming double-stranded basal stem (i.e., the reconfiguration domain as disclosed herein) in a ORIENTR-ON configuration (e.g., when it is in a complex with a RNA-trigger), does not comprise UG motif at the base of the double-stem basal stem, and/or does not comprise a mismatched GHG (mGHG) motif in the basal stem.

In some embodiments, 3' basal stem sequence comprises a GHG sequence. In some embodiments, 3' basal stem sequence does not comprise a GHG motif. In some embodiments, 3' basal stem sequence and/or 5-basal sequence comprises one or more Drosha binding sequences.

In some embodiments, 5' basal stem sequence has a flanking 3' single stranded sequence which comprises a UG motif (see e.g., FIG. 1A). In alternative embodiments, 5' basal stem sequence has a flanking 3' single stranded sequence which does not a UG motif.

In some embodiments, 3' basal stem sequence has a flanking 3' single stranded sequence which comprises a CNNC motif. In some embodiments, 3' basal stem sequence has a flanking 3' single stranded sequence which does not comprises a CNNC motif.

The basal stem structure of an ORIENTR in an ORIENTR-ON configuration is commonly referred in the art as the region of the pri-miRNA structure that serves as "pri-miRNA scaffold", "miRNA scaffold," "scaffold portion," or simply "scaffold" of a miRNA. In some embodiments, it is envisioned that 5' basal stem sequence and 3' basal stem sequence are synthetic sequences as discussed herein, e.g., not naturally occurring in an endogenous miRNA. In such embodiments, the basal-stem structure and the output domain in an ORIENTR-ON configuration form an artificial pri-miRNA scaffold, or artificial miRNA scaffold structure, having an artificial or synthetic basal stem structure in the miRNA scaffold, which is recognized and processed by Drosha.

In alternative embodiments, where 5' basal stem and/or 3' basal stem sequences are not synthetic sequences, i.e., are not derived from an endogenous miRNA, 5' basal stem sequence and/or the 3' basal stem sequence can be derived from, or based upon 5' basal stem and/or 3' basal stem sequences obtained from an endogenous miRNA, e.g., but are not limited to, miR16-2, miR-26b, miR-196a-2, and miR-204, from humans (miRNA Accession numbers MIMAT0000083, MIMAT0000226, MIMAT0000265 respectively, as well as miR-26b, miR-196a-2, and miR-204 from other species.

Thus, in another aspect, an ORIENTR enables the formation of a pri-miRNA scaffold structure that is an artificial pri-miRNA scaffold structure, when the ORIETNR is in the ON configuration. Similarly, as the guide strand that is present in the output domain of the ORIENTR can be to any RNA target as disclosed herein, the ORIENTR can be used to provide an almost unlimited number of different non-naturally occurring pri-miRNAs, each having the same ORIENTR pri-miRNA scaffold sequence but different guide strand and passenger strand sequences.

F. Output Domain; Guide Strand, Apical Loop and Passenger Strand

One aspect of the ORIENTR is the presence of an output domain. As disclosed herein the output domain comprises the double stranded nucleic acid sequences of a RNAi. As shown in FIG. 5A, an output domain comprises stem-loop structure (also referred to herein as a "RNAi hairpin" structure) that comprises: (i) a guide strand (ii) a loop, and (iii) a passenger strand, which forms a hairpin structure. In some embodiments, the stem-loop structure is a pri-miRNA hairpin (that is not part of a correctly formed part of pri-miR scaffold structure). In some embodiments, an output domain of an ORIENTR comprises double stranded nucleic acid sequences of a pri-mRNA (e.g., a pri-miRNA hairpin) for processing into a 5p-miRNA, where, in the absence of a RNA-trigger molecule, the output domain has a pri-miRNA sequence that is not in the correct scaffold configuration to be processed by microprocessor. As discussed herein, in the presence of the RNA-trigger, the ORIENTR reconfigures its secondary structure such that the pri-miRNA is in the correct scaffold configuration for microprocessor and miRNA biogenesis. Stated differently, in some embodiments, the output domain comprises a RNA-duplex for RNAi, but where the RNA-duplex cannot be processed by the microprocessor in the absence of the RNA-trigger molecule.

In some embodiments, the output domain comprises a RNAi duplex which is a pri-miRNA duplex, where the pri-miRNA duplex can only form the correct a pri-miRNA scaffold structure in the ORIENTR when the RNA-trigger is present. As described herein, when the ORIENTR is in the ORIENTR-ON configuration, the secondary structure is reconfigured so that the pri-miRNA duplex is in a correct scaffold structure to be recognized and cleaved by Drosha. Without wishing to be bound by theory, in the presence of a RNA-trigger, the ORIENTR is reconfigured to an ORIENTR-ON configuration where a pri-miRNA scaffold structure is correctly formed that comprises: (i) the output domain (e.g., a miRNA duplex), (ii) a basal stem duplex/structure (e.g., the reconfiguration domain) and single stranded 5' flanking sequences and 3' flanking sequences. As shown in FIG. 5C, 3' flanking sequence (S2f) serves as the single stranded 5' flanking sequence in a pre-miR scaffold, and the spacer sequence serves as the single stranded 3' flanking sequence. When the pri-miRNA scaffold structure is correctly configured in an ORIENTR-ON configuration, it allows Drosha recognition and cleavage.

In some embodiments, the minimal length of the single-stranded flanks can easily be determined as when it becomes too short, Drosha processing may fail and sequence specific inhibition will be reduced or even absent. In one embodiment, the pri-miRNA scaffold has a 5'-sequence flank and a 3' sequence flank relative to the predicted pre-miRNA structure, and in some embodiments, 5'-sequence flank (e.g., S2$^f$) and a 3' sequence flank (e.g., spacer sequence) either that flank 5' basal stem sequence and 3' basal stem sequence, respectively, can be derived from sequences from naturally occurring pri-miRNA sequences.

In some embodiments, an output domain of the ORIENTR comprises (1) a hairpin structure comprising: (a) a duplex region formed from a guide sequence and a sense sequence; and, (b) a single-stranded loop linking the guide sequence and the sense sequence; wherein the duplex region can form a siRNA or an miRNA comprising the guide sequence, or be cleaved by Dicer to generate the siRNA or miRNA, wherein the guide sequence is substantially complementary to a transcript of a target gene.

In some embodiments, an output domain of an exemplary ORIENTR comprises a guide sequence, an apical loop and a passenger (also referred to as sense) sequence, which forms a short duplex of no more than 19 base pairs in length. In some embodiments, the short duplex comprises one or more mismatched sequences. In some embodiments, the output domain comprises the sequence that makes up the pri-miRNA 16-2 scaffold sequence, where the miR16-2 guide sequence is swapped with any miRNA guide sequence for a target nucleic acid sequence. It is envisioned that one of ordinary skill of art can readily use any miRNA (miR) sequence to replace the miR16-2 guide sequence or miR-HSUR4 guide sequence used in the exemplary ORIENTRs as disclosed herein. In some embodiments, a person of ordinary skill in the art can substitute the HSUR4 miR guide sequence for any miR guide sequence to a target nucleic acid sequence (e.g., gene or other non-coding target nucleic acid sequence as disclosed herein. Accordingly, a person of ordinary skill the art will also use a suitable passenger sequence to the specific guide miR utilized in the ORIENTR in the output domain. In some embodiments, a guide sequence of a miR for use in the output domain can be between 20-22nt in length, and the corresponding passenger strand can similarly be between 20-22nt in length.

Moreover, in some embodiments, the output domain can be modified to be any pri-miRNA scaffold that can be recognized by Drosha. As disclosed herein, in the absence of the RNA-trigger molecule (ORIENTR_OFF configuration), a pri-miRNA scaffold in the output domain is in the incorrect structure/configuration, but when the RNA-trigger forms a complex with the ORIENTR, the ORIENTR reconfigures such that the pri-miRNA scaffold is in the correct configuration so that the pri-miRNA scaffold can be recognized and cleaved by Drosha and subsequently processed by the RNAi machinery to produce a pre-miRNA, which can subsequently be processed into a mature miRNA duplex.

In some embodiments, an output domain comprises a RNA duplex region that can be cleaved by Dicer to generate an siRNA or miRNA that, in turn, inhibits the expression of a target gene via RNA interference (RNAi) mechanism. In one aspect, the output domain of an ORIENTR comprises a guide sequence and a sense sequence capable of forming a duplex region that can either become or be cleaved by Dicer to generate an siRNA or an miRNA comprising the guide sequence, wherein the guide sequence is substantially complementary to a transcript of a target gene, and wherein the duplex cannot be bound by Drosha and/or cleaved by Dicer in the absence of a RNA-trigger due to the fact that the secondary structure of the basal-stem (i.e., the reconfiguration domain) of the pri-miRNA scaffold is not formed.

As used herein, "siRNA" or "miRNA" includes any small interfering RNA (RNAi) microRNA that can be loaded into RISC complex and inhibit target gene expression through the RNA interference mechanism (e.g., either cleave the target sequence, or inhibit target mRNA translation). The siRNA miRNA does not have to be between 19-21 nucleotides in length. In some embodiments, the siRNA does not require Dicer cleavage to be loaded into RISC.

Mature miRNAs are small non-coding RNA molecules having lengths of from about 19 nucleotides and 23 nucleotides that function in RNA silencing (RNAi) and post-transcriptional regulation of gene expression. MiRNAs function via base-pairing with complementary sequences within a target mRNA, which leads to mRNA silencing by one or more following processes, including: (1) target mRNA cleavage, (2) destabilization of a target mRNA by truncation of its polyA tail, and (3) reducing the efficiency of target mRNA translation. As miRNAs resemble small interfering RNAs (siRNAs) of the RNA interference (RNAi) pathway, however, miRNAs differ in origin from siRNAs. That is, while siRNAs derive from longer regions of double-stranded DNA, miRNAs derive from pri-miRNAs characterized by the formation of short hairpins.

In certain embodiments, part of the guide sequence and part of the sense sequence, when forming part of the duplex region, comprises one or more mismatched base pairs. In certain embodiments, the part of the guide sequence is a continuous stretch of about 3 nucleotides or less. In certain embodiments, the part of the sense sequence is a continuous stretch of about 5 nucleotides or less. In some embodiments, the guide and the sense strand form a duplex stem that, from the base, is a continuous stretch of about 8 or 9 nucleotides or less, followed by 2nt mismatch, and about a 7nt duplex, followed by an apical loop structure. In certain embodiments, the guide sequence comprises a 2-nucleotide 3' overhang. In certain embodiments, the guide sequence comprises a 1-nucleotide 5' overhang.

In some embodiments, the output domain does not comprise a UGU/GUG motif in the apical loop. In some embodiments, the output domain does comprises a UGU/GUG motif in the apical loop.

It is envisioned that while the ORIENTR is designed to reconfigure to generate a pri-miRNA scaffold structure for processing into a single pre-miRNA from the 5' arm of the hairpin of the output domain (to form a 5p-miRNA), it is envisioned that the output design of the ORIENTR, and/or 5'-basal stem sequences and 3'-basal stem sequence can be modified to form, in the presence to a RNA-trigger, the correct structural requirements of other pri-miRNA scaffolds.

In some embodiments, a guide RNA sequence and the passenger RNA sequence may be selected such that the RNA structures that the pri-miRNA structure in the output domain, when the RNA-trigger is present, resembles the corresponding predicted original pri-miRNA. In some embodiment, a pri-miRNA duplex in the output domain comprises two separate RNA strands that are hybridized via complementary base pairing, and in some embodiments, do not necessarily need to be fully base paired, i.e. not all nucleotides in the guide and passenger strand are base paired, and the guide strand and the passenger strand do not need to be the same length. How to use miRNA precursor molecules as scaffolds for any selected target sequence and substantially complementary first RNA sequence is described e.g. in Liu Y P Nucleic Acids Res. 2008 May; 36 (9): 2811-24, which is incorporated herein in its entirety.

In general, the miRNA or siRNA guide sequence can target a RNA transcript of a target gene or expressed nucleic acid sequence. In some embodiments, the guide sequence in the output domain targets a RNA target, as that term is defined herein. In certain embodiments, the RNA target may be an mRNA of a target gene. In some embodiments, a RNA target can also be an endogenous miRNA or other non-coding RNA sequence. In certain embodiments, the RNA target may be a non-coding RNA of interest. In certain embodiments, the target may also function as a RNA-trigger as disclosed herein. If the target is an identical to the RNA-trigger sequence, the ORIENTR riboregulator as disclosed herein is capable of self-modulating through a feedback control mechanism. In addition, one or more target transcripts sharing a common target sequence maybe targeted simultaneously by the same ORIENTR.

The target RNA or target gene can be any gene of interest, including genes coding for proteins or non-protein products. The target gene may be either disease-associated genes or normal genes (such as essential genes required for cell viability). Merely to illustrate, exemplary disease-associated genes include BCL-1 (apoptosis), HSF-1 (heat shock factor, important to pancreatic cancer and others), NOX-4 (pancreatic cancer), etc. In certain preferred embodiments, the target gene is an intended/desired/pre-determined (as opposed to a spurious) target gene.

G. Other Components:
(i) Leak-Reduction Motif

Figure 2D:
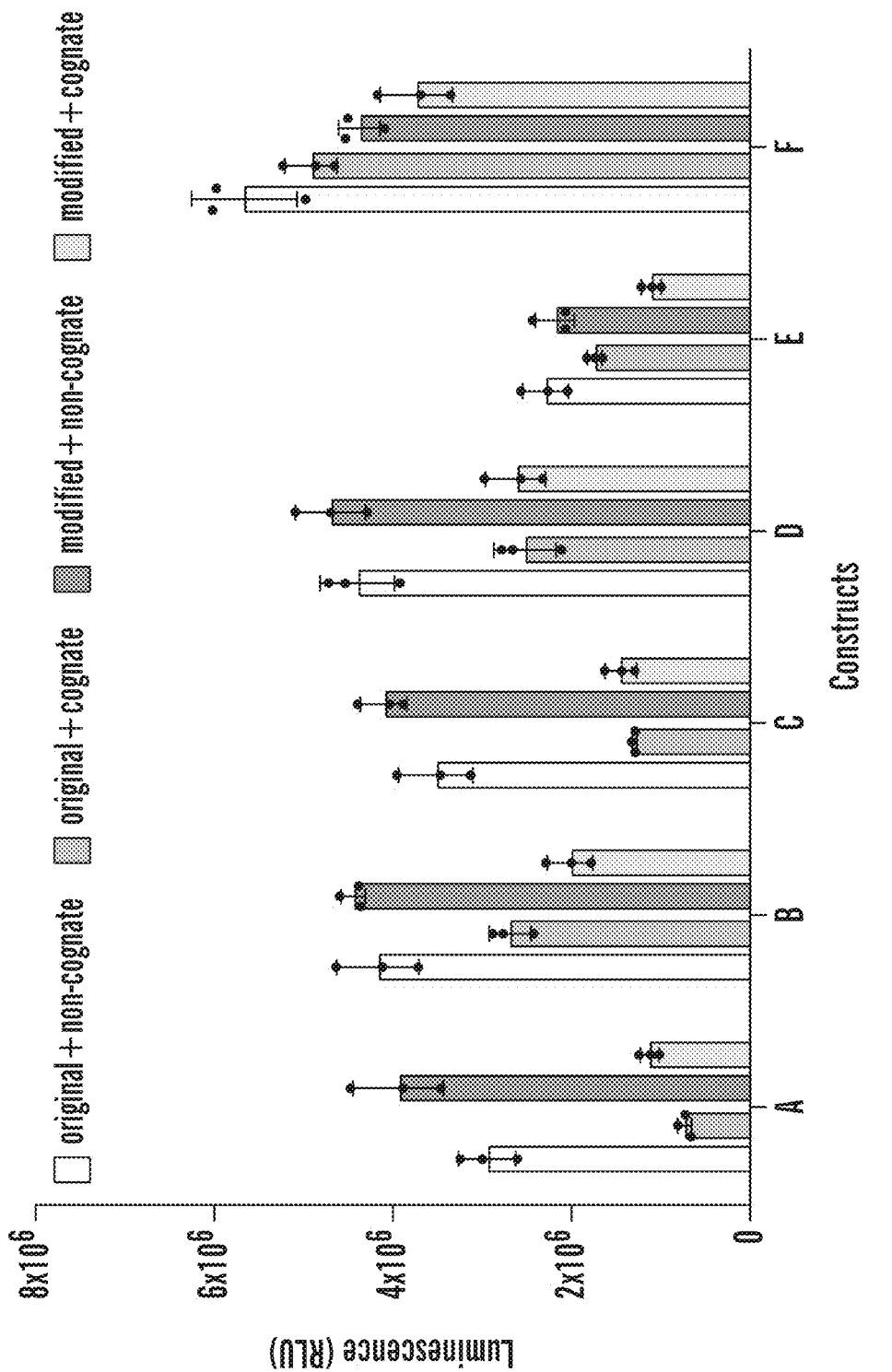

In some embodiments, as shown in FIG. 2D, the ORIENTR further comprises a small hairpin sequence (SHS) located 3' of 3' basal stem sequence. In some embodiments, in the absence of a RNA-trigger sequence, this small hairpin sequence (SHS) can form a small double stranded duplex, fully, or partially with a portion of 3' basal stem sequence. In some embodiments, the SHS is a reverse complement to at least a portion, or the entire length of the 11bp 3' basal stem sequence. Accordingly, in the presence of a RNA-trigger, as 5' basal stem sequence is displaced, it displaces the small hairpin sequence from complementary base pairing with 3' basal stem, allowing the reconfiguration domain to form and the correct pri-miRNA scaffold structure to occur which can be processed by microprocessor.

In some embodiments, 3' basal sequence is weakly base-paired with the SHS in the absence of a RNA-trigger. In some embodiments, 3' basal sequence has higher affinity for complementary base pairing with 5' basal sequence than the SHS. In some embodiments, the SHS and the 3' basal sequence are less than 100% complementary, e.g., is less than 95%, or less than 90% or less than 85%, or less than 80% complementary to 5' basal sequence than the SHS. In some embodiments, at least 3, or at least 4, or at least 5, or at least 6, or at least 7, or at least 8, or at least 9, or more than 9 nt of 3' basal sequence can complementary base pair with a SHS sequence in an ORINTR in the absence of RNA-trigger sequence.

In some embodiments, the SHS sequence comprises a loop region, and at least 4, or at least 5, or at least 6, or at least 7, or at least 8, or at least 9, or at least 10 or 11 or more bases that complementary base pair, in perfect or imperfect stem, with all or part of 3'-basal sequence. In some embodiments, a SHS sequence comprises between 6-8nt that can complementary base pair with 3'-basal sequence in the absence of a RNA-trigger.

(ii) 5' GGG, Spacer Sequence

In some embodiments, the ORIENTR optionally comprises a GGG sequence located 5' of the toehold sequence. In some embodiments, the GGG sequence can be readily replaced by one of ordinary skill in the art for any suitable 5' sequence for a riboregulator.

In some embodiments, the ORIENTR further comprises a spacer domain (also referred to as a spacer sequence), which is located at the 3' of 3' basal stem sequence. In some embodiments, the spacer domain is about 9-33 nucleotides in length. In some embodiments, the spacer domain is about 21 nucleotides in length. In some embodiments, the spacer domain is situated between 3' basal stem sequence and 3' Pol III terminal sequence of the ORIENTR molecule. In some embodiments, the spacer domain is greater than 33 nucleotides in length and can contain single- and double-stranded regions. In some embodiments, the spacer domain is single-stranded.

In some embodiments, the spacer domain comprises an endogenous 3' sequence flanking sequence to a pri-miRNA scaffold. In some embodiments, the spacer domain is a 3' sequence flanking sequence to pri-miR-16-2. In some embodiments, the spacer domain comprises a CNNC motif for microprocessor recognition. In some embodiments, the spacer domain does not comprises a CNNC motif for microprocessor recognition.

(iii) 3' RNA Pol III Termination Sequence

In some embodiments, the ORIENTR further comprises a 3' RNA pol III termination sequence at 3' terminal. RNA Pol III and RNA polymerase termination sequences are well known in the art, and include, without limitation a T7 RNA polymerase termination signal, which can include a 47-nt T7 RNA polymerase terminator at 3' end of the ORIENTR, as disclosed in U.S. Pat. No. 9,550,987, which is incorporated herein in its entirety by reference.

In some embodiments, the terminator sequence is a RNA Pol III terminator sequence, such as a terminator sequence for U7 promoter. It is envisioned that an ORIENTR can comprise a 3' termination sequence commonly known in the art, that is selected based on the promoter that is operatively linked to the transcription of the ORIENTR. In some embodiments, a terminator sequence is a a Pol-III terminator sequence, for example, but without limited to, a poly-U sequence (e.g., 7xU) as a terminator sequence for a U6 promoter.

(f) RNA Trigger

The RNA-trigger, which is used interchangeably herein with the term "trigger RNA", is a RNA nucleic acid sequence that functions as a trans-activating RNA (taRNA) sequence to the S1 portion of 3' sequestering arm sequence. Referring to FIG. 5C, in some embodiments, the RNA trigger comprises (i) a T1* sequence which is complementary to the toehold sequence T1 of the ORIENTR, and (ii) a S1* sequence, which is complementary to the S1 portion of 3' sequestering arm sequence. In some embodiments, depending on the length and configuration of the sequestering-loop domain of the ORIENTR, the RNA trigger can optionally comprise a S2* sequence, which is complementary fully or partially, to a S2 region of 3' sequestering arm sequence of ORIENTR.

In some cases, the RNA-trigger, is a synthetic RNA or a non-natural RNA sequence. In some embodiments, the RNA-trigger is less constrained in sequence than are those of the prior art, and accordingly a variety of riboregulators may be generated and importantly used together in a single system such as a cell. In contrast to other riboregulators, the ORIENTR as disclosed herein regulates miRNA biogenesis and does not directly regulate transcription or translation. The sequence of the toehold is separate from the sequence in the output domain (e.g., the guide sequence), which allows an ORIENTR to be designed to allow "plug and play" implementations of higher order cellular logic.

In some embodiments, a RNA-trigger is capable of hybridizing to a toehold T1 sequence as disclosed herein, and subsequently to S1 and/or S2 regions in 3' sequestering arm sequence, under high to medium stringency hybridization conditions or physiological conditions of a cell, including a living cell, such as mammalian cell in vitro or in vivo.

In alternative embodiments, a RNA-trigger comprises an endogenous RNA, e.g., a natural RNA sequence (i.e., it is RNA that is endogenous to a cell). In some embodiments, the ORIENTR molecules as disclosed herein provide sufficient freedom in the sequence that the trigger RNA (and corresponding region of the toehold region in the ORIENTR to which the trigger-RNA hybridizes) can be activated by, for example, RNAs such as, but not limited to endogenous RNAs. In some embodiments, the RNA-trigger is an activating RNA (i.e., its presence in a cell, is at a sufficient levels to activate protein expression (or translation) if a coding region of interest). In some embodiments, a RNA-trigger is an endogenous RNA sequence that is an repressing RNA sequence, e.g., its presence in a cell, e.g., at sufficient levels, represses protein expression or translation of a specific gene. For such embodiments, a RNA-trigger can comprise a miRNA or other non-coding nucleic acid expressed in a cell. In some embodiments, the RNA trigger can comprise a mRNA, a miRNA, a siRNA, a ribozyme or a non-coding RNA. In some embodiments, the RNA trigger does not comprise RNA that is not the target of the miRNA produced from the output domain. In alternative embodiments, the RNA trigger comprises a RNA that is the target of the miRNA produced from the output domain. For example and without wishing to be bound by theory, if there is excess production of a specific RNA transcript (e.g., mRNA), the trigger can be the specific RNA transcript and thus allow processing of a miRNA from the output domain to repress the target transcript in a feedback mechanism, effectively controlling the specific RNA transcript expression levels. In some embodiments, the specific RNA transcript can comprise mutations or SNPs associated with a disease or disorder or cellular process.

In another aspect, the invention provides a RNA-trigger molecule as disclosed herein can comprises, in a 5' to 3' direction, a third domain referred to as S2*, a second domain referred to as S1*, and a first domain (T1*), where the T1* hybridizes and complementary base pairs to a toehold domain of any of the foregoing ORIENTR, and where the second domain (S1*) and third domain (S2*) hybridizes to and complementary base pairs with S1 and S2 sequences of 3' sequestering arm sequence, respectively (i.e., the sequence downstream (3') of the toehold domain). In some embodiments, the T1*, S1* and S2* sequences are single stranded RNA (ss RNA) and comprises no or minimal secondary structure.

In some embodiments, the first domain (T1*) is 100% complementary to the toehold domain (T1). In some embodiments, the first domain (T1*) is less than 100% complementary to T1, and can be, e.g., at least 90%, at least 91%, at least 92%, at least 93%, or at least 94%, or at least 95%, or at least 96%, or at least 97%, or at least 98%, or at least 99%, or at least 99.5% complementary to the toehold domain. In some embodiments, as disclosed herein the first domain (T1*) of the RNA trigger can complementary base pair with a toehold domain (T1) of an ORIENTR, were the complementary base pairing comprises one or more mismatches between T1* and T1.

In some embodiments, the second domain (S1*) is 100% complementary to the S1. In some embodiments, the second domain (S1*) of the RNA-trigger may be less than 100% complementary to S1, and can be, e.g., at least 90%, at least 91%, at least 92%, at least 93%, or at least 94%, or at least 95%, or at least 96%, or at least 97%, or at least 98%, or at least 99%, or at least 99.5% complementary to S1. In some embodiments, the third domain (S2*) is 100% complementary to the S2. In some embodiments, the third domain (S2*) of the RNA-trigger may be less than 100% complementary to S2, and can be, e.g., at least 90%, at least 91%, at least 92%, at least 93%, or at least 94%, or at least 95%, or at least 96%, or at least 97%, or at least 98%, or at least 99%, or at least 99.5% complementary to S2. In some embodiments, as disclosed herein the second domain (S1*) of the RNA trigger can complementary base pair with a S1 sequence of 3'sequestering arm sequence of an ORIENTR, where the complementary base pairing comprises one or more mismatches between S1* and S1. In some embodiments, as disclosed herein the third domain (S2*) of the RNA trigger can complementary base pair with a S2 sequence of 3'sequestering arm sequence of an ORIENTR, where the complementary base pairing comprises one or more mismatches between S2* and S2.

In some embodiments, the RNA trigger sequence can comprise a T1, S1 and s2 region, which cumulatively can vary in size depending on the length of the toehold T1 of the ORIENTR and the S1 and S2 lengths in 3' sequestering arm sequence. In some embodiments, an ORIENTR toehold domain can vary from ~9 to >50 nt. In some embodiments, a ORIENTR toehold sequence can be between 70-90nt, e.g., at least 70, 75, 80, 85, and 90 nt.

In some embodiments, the length of the T1* of the RNA-trigger matches approximately the same length of the toehold T1 length in the corresponding ORIENTR. In some embodiments, the length of the T1* region in the RNA trigger can also be much longer than that of the T1 region. In some embodiments, the RNA trigger comprises a T1*, S1* and S2* RNA strand that cumulatively, is the same, or a similar length to the cumulative length of the T1, S1 and S2 in the corresponding ORIENTR.

In some embodiments, the cumulative length of the single stranded RNA trigger region (i.e., cumulative length of T1*, S1* and S2*) can be between 20 and ≥116 nucleotides. In some embodiments, the T1* is between 9-90nt, the S1* region is between 8-14 bp (e.g., typically 11bp) and the S2* region is about 15 bp. It is envisioned that the single-stranded portion of the RNA-trigger can be depicted by the cognate ORIENTR molecule. It is envisioned that one of ordinary skill can modify the T1*, S1* and S2* regions of a RNA-trigger accordingly. In some embodiments, single-stranded portion of the RNA-trigger is at least 20nt, or between about 20-40nt, or between about 40-60nt, or between about 60-80nt, or between about 80-90nt, or between about 90-100nt in length, or longer than 100nt in length.

For very long RNA-trigger lengths, the single stranded portion of the RNA trigger could be designed or modified to avoid eliciting an innate response to the ds-RNA. In some embodiments, the trigger RNA does not need to be fully reverse complementary to the toehold (T1) and 3' sequestering arm. It is envisioned that mismatches between RNA-trigger and ORIENTR could be used to reduce immune response. In some embodiments, the number of mismatches in the portion of the S1* and S2* of trigger RNA that binds to 3' sequestering arm sequences S1 and S2 regions respectively (e.g., when the ORIENTR is in the ORIENTR-ON configuration), is smaller than the number of mismatches between the S2 region of 3' sequestering arm and 3' flanking sequence, and the S1 region of 3' sequestering arm and 5' basal stem when the ORIENTR is in an ORIENTR-OFF configuration.

In some embodiments, a RNA-trigger can comprise more than one strand of RNA, and such multiple RNAs in combination to provide the first, second and third domain for hybridization with the RNA-trigger sensing domain of the ORIENTR.

Accordingly, the ORIENTRs can act as in vivo sensors, and respond by inducing miRNA processing and production when a trigger-RNA is present in a cell, in real time in living cells or other types of RNA-containing samples. Accordingly, the technology disclosed herein can be used to allow an inducible system to activate the miRNA processing of the pri-miRNA in the ORIENTR when the trigger RNA, in some embodiments, an endogenous RNA is present, in real time without having to induce the miRNA expression and processing using a separate inducible system.

For optimal ORIENTR kinetics, the RNA-trigger should possess minimal secondary structure and full complementarity (i.e., 100%) to the toehold domain of the ORIENTR. As used herein, secondary structure refers to non-linear structures including for example hairpin structures, stem loop structures, and the like. Accordingly, in some embodiments, a RNA-trigger useful in the methods, compositions and systems as disclosed herein comprises sequences T1*, S1* and S2* that have little to no probability of forming secondary structure under the conditions of its use. It is envisioned that a RNA-trigger as disclosed herein can have secondary structure in non-binding regions (i.e., region distinct to T1*, S1* and S2*) that can form secondary structures for enhanced stability and/or nuclear localization of the RNA-trigger, as disclosed herein. Those of ordinary skill in the art are able to determine such sequences either manually or through the use of computer programs available in the art.

In certain embodiments, the sequence of the RNA-trigger can be adjusted to achieve optimal levels of hybridization with the toehold and S1 and S2 sequences. The optimal level of hybridization in a given situation (e.g., cell) may not necessarily reflect the maximum possible hybridization. Mismatch or wobble base-pairings, substituting G-C with A-U base pairing or other modified base-pairing may be used to fine-tune the optimal/desired level of hybridization. Similarity, in some embodiments, optimal levels of hybridization may be achieved by adjusting the sequences of T1, S1 and S2 to achieve optimal (again, not necessarily the maximum) level of hybridization with the RNA-trigger.

(i) 5' Stability Hairpin and Secondary Structure of the RNA-Trigger.

In some embodiments, a RNA-trigger comprises a 5' short hairpin for stability (referred to herein as a "stability hairpin"). In some embodiments, an exemplary RNA-trigger is shown in FIG. 5B, has the following structure from 5' to 3': a 5' GGG sequence, a double-stranded hairpin comprising a stem and loop, where the stem can be 8nt in length with a 6nt loop structure, a 3nt single stranded region, a single stranded RNA region that is the cognate to, and can complementary base pair to the toehold region (comprising S2*, S1* and T* as disclosed herein), and a terminating sequence comprising at least 3 U base pairs. Without wishing to be bound by theory, the secondary structure of an exemplary RNA-trigger is shown in FIG. 5B, and shows an exemplary RNA-trigger with a 37nt single stranded region that comprises T1*, S1* and S2* sequences which can complementary base pair with T1, S1 and S2 regions in the RNA-trigger binding domain of the toehold and 3' sequestering arm, respectively. In some embodiments, a stability hairpin of a RNA-trigger can be longer or shorter than 8nt shown in FIG. 5B, and the loop can be between, e.g., 3-10 bp. In some embodiments, a hairpin structure in a RNA-trigger serves the purpose to increase RNA stability and therefore it is envisioned that the hairpin structure of a RNA-trigger can be modified by one of ordinary skill in the art to use different hairpin configurations, provided that the modified hairpin improves the stability of the RNA-trigger as compared to a RNA-trigger without a hairpin structure, and/or does not interfere with the binding of any one or more of T1*, S1* or S2* to the toehold and 3' sequestering arm sequence of the ORIENTR.

In some embodiments, 5' stability hairpin on a RNA-trigger can comprise a stem length of between 6nt and 20nt. In some embodiments, a stability hairpin has a double stranded stem of at least 6nt, or In some embodiments, the RNA-trigger, including the stability hairpin can comprise one or more chemical modifications that confer resistance to nuclease degradation. Nuclease resistance may be conferred by use of polyguanosine (>9 nucleotides), DNA, 2'-OMe, or LNA, or forms of RNase resistant bases. Accordingly, an ORIENTR as disclosed herein can further comprise stretches of nuclease-resistant sequences comprise a stretch of at least about 9 nucleotides of polyguanosine, DNA, 2'-O-methyl modified nucleotide, or LNA.

(ii) Cr-Trigger-RNAs

In some embodiments, a stability hairpin loop in a RNA-trigger is replaced with a CRISPR RNA (crRNA) scaffold hairpin to increase trigger-RNA targeting to an ORIENTR. In some embodiments, the hairpin-loop in a RNA-trigger is modified to use a CRISPR RNA (crRNA) scaffold hairpin to aid in localization of the RNA-trigger to the nucleus. Any crRNA scaffold hairpin is envisioned to replace a stability hairpin of the RNA-trigger. In some embodiments, the crRNA is a scaffold hairpin used in rfxCas13d, which can be bound and deactivated by rfxCas13d (dCas13d). In some embodiments, rfxCas13d scaffold hairpin comprises the sequence of SEQ ID NO: GGAAACCCCUACCAACUG-GUCGGGGUUUGAAAC (SEQ ID NO: 5). SEQ ID NO: 5 is encoded by the nucleic acid sequence of: GGAAACCCC-TACCAACTGGTCGGGGTTTGAAAC (SEQ ID NO: 6).

In some embodiments, a rfxCas13d scaffold hairpin can recruit dCas13d, and a nuclear localization signal on the dCas13d can assist transporting the cr-trigger back to the nucleus. Therefore, in some embodiments, a cr-trigger is expressed in cells comprising dCas13d or is co-expressed in a system where dCas13d is also present.

In some embodiments, a RNA-trigger can also comprise a nuclear localization signal to assist sequestering in the nucleus, and/or transporting the RNA-trigger to the nucleus.

In certain embodiments, the RNA trigger can comprise nucleotides with chemical modifications, if any, are largely/mostly present on one or more the single-stranded polynucleotides. In some embodiments, the RNA-trigger is not an endogenous RNA, all or part of the RNA-trigger may be modified to include nuclease resistance. Nuclease resistance may be conferred by use of polyguanosine (>9 nucleotides), DNA, 2'-OMe, or LNA, or forms of RNase resistant bases. Accordingly, a RNA-trigger as disclosed herein can further comprise stretches of nuclease-resistant sequences comprise a stretch of at least about 9 nucleotides of polyguanosine, DNA, 2'-O-methyl modified nucleotide, or LNA.

(g) Systems

One aspect of the technology disclosed herein relates to a system comprising both an ORIETNR as disclosed herein and a RNA-trigger molecule. In some embodiments, the system is in a cell, e.g., a living cell. In some embodiments the cell is a mammalian cell.

In some embodiments, the technology relates to a system comprising: (a) an ORIENTR riboregulator as disclosed herein and (b) a RNA-trigger sequence, as disclosed herein.

In certain embodiments, in the absence of a RNA-trigger, generation of the siRNA or miRNA and/or productive incorporation of the siRNA or miRNA into RISC is inhibited by at least about 2-fold (i.e., to 50%), 5-fold (i.e., to 20%). 10-fold (i.e., to 10%), or 20-fold (i.e., to 5%) or more.

In some embodiments, without wishing to be bound by theory, there is more negative free energy for the ORIENTR-trigger conformation (i.e., the ORIENTR-ON configuration) than the free energies of the ORIENTR and the trigger-RNA alone (i.e., ORIENTR-OFF configuration) in order to make the reaction between the ORIENTR-OFF and the RNA-trigger spontaneous, and therefore enable, in the presence of a RNA trigger, the spontaneous reconfiguration of the ORIENTR from the OFF configuration to the ON configuration.

As discussed briefly herein, an ORIENTR riboregulator may also function as repressors of protein translation. In accordance with the invention, a new class of riboregulators that can function in living mammalian cells is provided that can repress translation of a target nucleic acid (also referred to a gene of interest or GOI) in response to a trigger RNA by a novel reconfiguration of the secondary structure to form a correct pri-miRNA scaffold structure that is recognized and processed by Microprocessor and generate miRNA that can in turn repress translation of the target nucleic acid.

In some embodiments, the trigger RNA is a single-stranded RNA containing a sequence that is perfectly complementary to the T1 region of the ORIENTR as shown in FIG. 5C, and thus can have a total length of 37-nts. When the RNA-trigger and ORIENTR are co-expressed, the trigger RNA binds to the toehold domain of the ORIENTR and completes a branch migration reaction with 3' sequestering arm domain. Displacement of 5' basal stem sequence enables the ORIENTR to completely and rapidly refold and 5' basal stem sequence to complementary base pair with 3' basal stem sequence to form the reconfiguration domain and the correctly formed pri-miRNA scaffold substrate for Drosha and subsequent microprocessor processing. This secondary structure reconfiguration causes 5'-basal stem and 3'-basal stem sequences to form a new base hairpin domain.

Like the toehold activator switches, the ORIENTR riboregulators as disclosed herein can adopt trigger RNAs with virtually arbitrary sequences. Consequently, it is possible to design large ORIENTR libraries with a high degree of orthogonality. In addition, they can be used to trigger translational repression (e.g., via the processing of the miRNA) in response to exogenous and endogenous RNAs.

In another aspect, the invention provides a system comprising one or more of any of the foregoing ORIENTR riboregulators and any of the foregoing complementary RNA-triggers (also referred to as trans-activating RNA or taRNA), optionally operably linked to a coding domain.

In some embodiments, the system is a cell. In some embodiments, the cell is a eukaryotic cell. In some embodiments, the cell is a living cell. In some embodiments, the cell is in vivo. In some embodiments, the cell is a mammalian cell, e.g., a human cell, and can be a cell in a subject, for example a cell in a subject in need of treatment as disclosed herein. In some embodiments, the system is a cell-free in vitro system.

In some embodiments, the ORIENTR riboregulator and the RNA-trigger are hybridized to each other. In some embodiments, the ratio of ORIENTR riboregulator to RNA-trigger is less than 1, less than 0.5, or less than 0.1.

The systems of the invention may include a plurality of ORIENTR riboregulators (e.g., a plurality of ORIENTRs, optionally together with cognate RNA-triggers) having minimal cross-talk amongst themselves. In some embodiments, the systems may comprise at least 2, 3, 4, 5, 6, 7, 8, 9, 10, 11, 12, 13, 14, 15, 16, 17, 18, 19, 20 or more ORIENTR/RNA-trigger riboregulators, having minimal cross-talk (e.g., on the level of less than 20%, 19%, 18%, 17%, 16%, 15%, 14%, 13%, 12%, 11%, 10%, 9%, 8%, 7%, 6%, 5%, 4%, 3%, 2% or less).

In some embodiments, the system is comprised in a first nucleic acid comprising an ORIENTR and the RNA-trigger is comprised in a second nucleic acid. In some embodiments, the first nucleic acid is a first plasmid and the second nucleic acid is a second plasmid. The plasmids may be DNA plasmids or RNA plasmids. In some embodiments, the ORIENTR and the RNA-trigger as present in the same plasmid, and are operatively linked to the same promoter. In some embodiments, the ORIENTR and the RNA-trigger as present in the same plasmid, and are operatively linked to different inducible promoters, e.g., to different tissue-specific promoters or other inducible promoters.

V. Vectors & Nucleic Acids

In another aspect, the invention provides a nucleic acid comprising any of the foregoing ORIENTR riboregulator systems or comprising sequences that encode any of the foregoing ORIENTR systems. In another aspect, the invention provides a host cell comprising any of the foregoing nucleic acids.

In another aspect, the invention provides a nucleic acid comprising any of the foregoing RNA-triggers or comprising sequences that encode any of the foregoing RNA-trigger. In another aspect, the invention provides a host cell comprising the nucleic acid.

It is to be understood that the invention contemplates modular nucleic acids encoding an ORIENTR and modular RNA-trigger encoding nucleic acids. Modular ORIENTR encoding nucleic acids as used herein refer to nucleic acid sequences that do not comprise an open reading frame (or coding domain for a gene of interest).

The invention further provides oligonucleotides comprising a ORIENTR sequence and oligonucleotides comprising a RNA-trigger sequence. In addition, the invention provides sets of two or more oligonucleotides. A first set of oligonucleotides includes two or more oligonucleotides whose sequences together comprise a ORIENTR sequence. The invention also provides a second set of oligonucleotides whose sequences together comprise a RNA-trigger sequence. For ease of cloning, it may be preferable to employ two oligonucleotides each of which includes a single stem-forming portion, in different cloning steps, rather than a single oligonucleotide comprising two stem-forming portions, in order to avoid formation of a stem within the oligonucleotide, which may hinder cloning. The oligonucleotides may be provided in kits with any of the additional components mentioned herein. The oligonucleotides may include restriction sites at one or both ends.

In some embodiments, the ORIENTR riboregulator (or system) is comprised in a first nucleic acid and the RNA-trigger is comprised in a second nucleic acid. In some embodiments, the first nucleic acid can be present in a first plasmid and the second nucleic acid can be present in a second plasmid. In alternative embodiments, a plasmid comprises a first nucleic acid comprising a ORIENTR and a second nucleic acid encoding a RNA-trigger. In some embodiments, the first nucleic acid and second nucleic acid are operatively linked to the same promoter, e.g., a tissue specific promoter or an inducible promoter as disclosed herein. In some embodiments, the first nucleic acid and second nucleic acid are operatively linked to different promoters, e.g., a different tissue specific promoter or an inducible promoter can be used to regulate the expression of the ORIENTR and RNA-trigger molecules independently. The plasmids may be DNA plasmids or RNA plasmids.

In another aspect, the invention provides a nucleic acid comprising any of the foregoing beacon ORIENTR riboregulators (or systems) or sequences that encode any of the foregoing ORIENTR riboregulators (or systems). In another aspect, the invention provides a host cell comprising said nucleic acid.

In another aspect, the invention provides a nucleic acid comprising any of the foregoing trans-activating RNA (RNA-trigger) or sequences that encode any of the foregoing RNA-trigger. In another aspect, the invention provides a host cell comprising said nucleic acid.

It will be appreciated that although a hairpin is formed from a single nucleic acid molecule, the two regions or sequences of the molecule that form the stem domain may be referred to herein as "strands". Thus the stem may be referred to herein as being partially or fully double-stranded. Nucleic acid sequences within a single molecule that are complementary to each other and are capable of forming a stem domain are said to be "self-complementary" or to "self-hybridizing" or able to "self-hybridize". In general, the hairpin and stem domains described herein form at and are stable under physiological conditions, e.g., conditions present within a cell (e.g., conditions such as pH, temperature, and salt concentration that approximate physiological conditions). Such conditions include a pH between 6.8 and 7.6, more preferably approximately 7.4. Typical temperatures are approximately 37° C., although prokaryotes and some eukaryotic cells such as fungal cells can grow at a wider temperature range including at temperatures below or above 37° C.

Various of the nucleic acids of the invention may be referred to herein as non-naturally occurring, artificial, engineered or synthetic. This means that the nucleic acid is not found naturally or in naturally occurring, unmanipulated, sources. A non-naturally occurring, artificial, engineered or synthetic nucleic acid may be similar in sequence to a naturally occurring nucleic acid but may contain at least one artificially created insertion, deletion, inversion, or substitution relative to the sequence found in its naturally occurring counterpart. A cell that contains an engineered nucleic acid may be referred to as an engineered cell.

Various embodiments of the invention involve nucleic acid sequences that are complementary to each other. In some instances, the sequences are preferably fully complementary (i.e., 100% complementary). In other instances, however the sequences are only partially complementary. Partially complementary sequences may be at least 60%, at least 70%, at least 80%, at least 90%, or at least 95% complementary. Sequences that are only partially complementary, when hybridized to each other, will comprise double-stranded regions and single-stranded regions. The single-stranded regions may be single mismatches, loops (where for instances a series of consecutive nucleotides on one strand are unhybridized), bulges (where for instances a series of consecutive nucleotides on both strands, opposite to each other, are unhybridized). It will be appreciated that complementarity may be determined with respect to the entire length of the two sequences or with respect to portions of the sequences.

Nucleic acids and/or other moieties of the invention may be isolated. As used herein, "isolated" means separate from at least some of the components with which it is usually associated whether it be from a naturally occurring source or made synthetically.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Nucleic acids may be single-stranded, double-stranded, triple-stranded and also quadruple-stranded (e.g., G-quadruplexes).

A naturally occurring nucleotide consists of a nucleoside, i.e., a nitrogenous base linked to a pentose sugar, and one or more phosphate groups which is usually esterified at the hydroxyl group attached to C-5 of the pentose sugar (indicated as 5') of the nucleoside. Such compounds are called nucleoside 5'-phosphates or 5'-nucleotides. In DNA the pentose sugar is deoxyribose, whereas in RNA the pentose sugar is ribose. The nitrogenous base can be a purine such as adenine or guanine (found in DNA and RNA), or a pyrimidine such as cytosine (found in DNA and RNA), thymine (found in DNA) or uracil (found in RNA). Thus, the major nucleotides of DNA are deoxyadenosine 5'-triphosphate (dATP), deoxyguanosine 5'-triphosphate (dGTP), deoxycytidine 5'-triphosphate (dCTP), and deoxythymidine 5'-triphosphate (dTTP). The major nucleotides of RNA are adenosine 5'-triphosphate (ATP), guanosine 5'-triphosphate (GTP), cytidine 5'-triphosphate (CTP) and uridine 5'-triphosphate (UTP). In general, stable base pairing interactions occur between adenine and thymine (AT), adenine and uracil (AU), and guanine and cytosine (GC). Thus adenine and thymidine, adenine and uracil, and guanine and cytosine (and the corresponding nucleosides and nucleotides) are referred to as being complementary to each other.

In general, one end of a nucleic acid has a 5'-hydroxyl group and the other end of the nucleic acid has a 3'-hydroxyl group. As a result, the nucleic acid has polarity. The position or location of a sequence or moiety or domain in a nucleic acid may be denoted as being upstream or 5' of a particular marker, intending that it is between the marker and 5' end of the nucleic acid. Similarly, the position or location of a sequence or moiety or domain in a nucleic acid may be denoted as being downstream or 3' of a particular marker, intending that it is between the marker and 3' end of the nucleic acid.

Nucleic acids may comprise nucleotide analogs including non-naturally occurring nucleotide analogs. Such analogs include nucleoside analogs (e.g., 2-aminoadenosine, 2-thiothymidine, inosine, 3-methyl adenosine, C5-propynylcytidine, C5-propynyluridine, C5-bromouridine, C5-fluorouridine, C5-iodouridine, C5-methylcytidine, 7-dcazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

The nucleic acids of the invention, including the ORIENTR and RNA-trigger, may be provided or present in a larger nucleic acid. The larger nucleic acid may be responsible for the transcription and thus production of the ORIENTR and RNA-trigger, as described the Examples, for example. The larger nucleic acid may comprise a nucleotide sequence that is transcribed to produce the ORIENTR and RNA-trigger of the invention. For convenience, the invention may refer to the larger nucleic acid as comprising the ORIENTR and/or RNA-trigger although it is to be understood that in practice this intends that the larger nucleic acid comprises a sequence that encodes the ORIENTR and/or RNA-trigger. Such encoding sequences may be operable linked to other sequences in the larger nucleic acid such as but not limited to origins of replication. As used herein, "operably linked" refers to a relationship between two nucleic acid sequences wherein the production or expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective association is acceptable.

As used herein, a regulatory sequence or element intends a region of nucleic acid sequence that directs, enhances, or inhibits the expression (e.g., transcription, translation, processing, etc.) of sequence(s) with which it is operatively linked. The term includes promoters, enhancers and other transcriptional and/or translational control elements. The ORIENTR and RNA-trigger moieties of the invention may be considered to be regulatory sequences or elements to the extent they control translation of a gene of interest that is operably linked to the ORIENTR. The invention contemplates that the ORIENTR and RNA-trigger of the invention may direct constitutive or inducible protein expression. Inducible protein expression may be controlled in a temporal or developmental manner.

As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In some embodiments, a nucleic acid encoding an ORIENTR and/or RNA trigger as disclosed herein is present in a vector. In some embodiments, a vector is a viral vector. In some embodiments, a vector is a non-viral vector, e.g., such as doggybone DNA, closed-ended DNA or close-ended RNA or other circular non-viral vectors, and the like.

In some of the aspects described herein, a nucleic acid sequence encoding an ORIENTR and/or RNA trigger as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. That is, the term vector refers to a nucleic acid capable of mediating entry of, e.g., transferring, transporting, etc., a second nucleic acid molecule into a cell. The transferred nucleic acid is generally linked to, e.g., inserted into, the vector nucleic acid. A vector may include sequences that direct autonomous replication, or may include sequences sufficient to allow integration into host cell DNA. Useful vectors include, for example, plasmids (typically DNA molecules although RNA plasmids are also known), cosmids, and viral vectors.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, 1992; Nabel & Feigner, 1993; Mitani & Caskey, 1993; Dillon, 1993; Miller, 1992; Van Brunt, 1988; Vigne, 1995; Kremer & Perricaudet, 1995; Haddada et al., 1995; and Yu et al., 1994.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

It is to be understood that although various embodiments of the invention are described in the context of RNA, the nucleic acids of the invention can be RNA or DNA. In general, RNA and DNA can be produced using in vitro systems, within cells, or by chemical synthesis using methods known in the art. It will be appreciated that insertion of ORIENTR elements upstream of an open reading frame (ORF) can be accomplished by modifying a nucleic acid comprising the ORF.

The invention provides DNA templates for transcription of a ORIENTR or RNA-trigger. The invention also provides DNA constructs and plasmids comprising such DNA templates. In certain embodiments, the invention provides a construct comprising the template for transcription of a ORIENTR or a RNA-trigger operably linked to a promoter.

In certain embodiments, the invention provides a DNA construct comprising (i) a template for transcription of a ORIENTR; and (ii) a promoter located upstream of the template. In certain embodiments, a construct or plasmid of the invention includes a restriction site downstream of 3' end of the portion of the construct that serves as a template for the ORIENTR, to allow insertion of an ORF of choice. The construct may include part or all of a polylinker or multiple cloning site downstream of the portion that serves as a template for the ORIENTR. The construct may also include an ORF downstream of the ORIENTR.

In certain embodiments, the invention provides a DNA construct comprising (i) a template for transcription of a RNA-trigger; and (ii) a promoter located upstream of the template. The invention further provides a DNA construct comprising: (i) a template for transcription of a ORIENTR; (ii) a promoter located upstream of the template for transcription of the ORIENTR; (iii) a template for transcription of a RNA-trigger; and (iv) a promoter located upstream of the template for transcription of the RNA-trigger. The promoters may be the same or different.

The constructs may be incorporated into plasmids, e.g., plasmids capable of replicating in bacteria. In certain embodiments, the plasmid is a high copy number plasmid (e.g., a pUC-based or pBR322-based plasmid), while in other embodiments, the plasmid is a low or medium copy number plasmid, as these terms are understood and known in the art. The plasmid may include any of a variety of origins of replication, which may provide different copy numbers. For example, any of the following may be used (copy numbers are listed in parenthesis): ColE1 (50-70 (high)). p15A (20-30 (medium)), pSCIO1 (10-12 (low)), pSOO1* (<4 (lowest). It may be desirable to use plasmids with different copy numbers for transcription of the ORIENTR and the RNA-trigger in order to alter their relative amounts in a cell or system. In addition, in certain embodiments a tunable copy number plasmid is employed.

The invention further provides viruses and cells comprising the nucleic acids, constructs (such as DNA constructs), and plasmids described above. In various embodiments, the cell is a prokaryotic cell. In various embodiments, the cell is a eukaryotic cell (e.g., a fungal cell, mammalian cell, insect cell, plant cell, etc.). The nucleic acids or constructs may be integrated into a viral genome using recombinant nucleic acid technology, and infectious virus particles comprising the nucleic acid molecules and/or templates for their transcription can be produced. The nucleic acid molecules, DNA constructs, plasmids, or viruses may be introduced into cells using any of a variety of methods known in the art, e.g., electroporation, calcium-phosphate mediated transfection, viral infection, etc.

VI. Cells and Compositions

In certain preferred embodiments, such ORIENTR riboregulator constructs and/or RNA-triggers can be delivered in its inactive form to a given cell type via any art recognized transfection methods (naked injection of RNA, nanoparticle-mediated delivery, liposome, viral vectors etc.).

As discussed herein, the nucleic acid constructs can be integrated into the genome of a cell. Such cells may be present in vitro (e.g., in culture) or in vivo (e.g., in an organism). The invention further provides transgenic plants and non-human transgenic animals comprising the nucleic acids, DNA constructs, and/or plasmids of the invention. Methods for generating such transgenic organisms are known in the art.

VII. Uses:

In another aspect, the technology disclosed herein provides a method of controlling protein translation, comprising combining any of the foregoing ORIENTR riboregulator systems with any of the foregoing complementary RNA-trigger, wherein the ORIENTR riboregulator comprises a toehold domain that is complementary to the RNA-trigger, and wherein the riboregulator system comprises a pri-mRNA to a target gene or gene of interest as disclosed herein.

In some embodiments, the ORIENTR riboregulator as disclosed herein can be used to repress a target gene or nucleic acid in cell for the treatment of a disease or disorder. Examples of such uses are discussed below:

a) ORIENTR Riboregulators for RNAi-Mediated Treatment of Specific Gene/Disease Targets An output domain of an ORIENTR can be configured to produce any output RNAi, e.g., miRNA or siRNA, and in some embodiments, a ribozyme, antisense molecule, or other RNAi embodiments described in the specification. Target genes for the output miRNA can be disease signals such as activated oncogenes or viral gene products. Alternately, target genes of the output miRNA can be endogenous mRNAs or miRNAs, which can include tissue RNAs or RNAs specific to a cell-cycle phase or disease state. RNA-triggers can be endogenous mRNAs or miRNAs, which can include tissue RNAs or RNAs specific to a cell-cycle phase or disease state.

In certain embodiments, the present disclosure provides methods for using the ORIENTR for biogenesis of miRNAs in a subject to treat a disease or disorder. For example, in some embodiments, disclosed herein are methods for regulating, promoting, normalizing, restoring, inhibiting, or modulating a desired cellular phenotype including, for example, differentiation, de-differentiation, proliferation, growth, cell death, contact inhibition by RNA-trigger mediated bioprocessing of one or more pri-miRNAs from an ORIENTR according to the methodology disclosed herein.

Within other aspects of those embodiments, disclosed herein are methods of use of an ORIENTR as disclosed herein for the treatment of a disease or condition that associated with the expression of one or more gene or the production of one or more protein, wherein one or more aspect of the disease or condition is reduced in severity following the RNA-trigger mediated bioprocessing of one or more pri-miRNAs from an ORIENTR riboregulator.

Within further embodiments, the present disclosure provides methods for reducing, preventing, and/or eliminating the growth of a target cell, which methods comprise contacting a target cell with a system disclosed herein, e.g., a vector comprising an ORIENTR and optionally a RNA-trigger, for RNA-trigger mediated bioprocessing of one or more pri-miRNAs from an ORIENTR riboregulator as disclosed herein, wherein the vector comprises: (a) a nucleic acid as disclosed herein that encodes an ORIENTR riboregulator, where the nucleic acid is operatively linked and under the translational control of a promoter, e.g., a constitutive promoter, or alternatively, an inducible promoter or tissue or cell-specific promoter, for transcription of the ORIENTR within a target cell and, optionally, the vector comprises (b) a nucleic acid that encodes a RNA trigger that is operably linked to and under regulatory control of a promoter (e.g., the same or different promoter operatively linked to the ORIENTR), and wherein production of the ORIENTR, in the presence of a RNA-trigger can allow the processing of one or more pri-miRNAs to reduce, prevent, and/or eliminate the growth and/or survival of the target cell.

Within still further embodiments, the present disclosure provides methods for the treatment of a human that is afflicted with a disease or another condition, wherein the disease, or other condition is associated with a target cell within the human, the methods comprising administering to the human a vector for the bioprocessing of one or more pri-miRNAs from an ORIENTR riboregulator, wherein the method comprises a target cell with a system disclosed herein, e.g., a vector comprising an ORIENTR and optionally a RNA-trigger, for RNA-trigger mediated bioprocessing of one or more pri-miRNAs from an ORIENTR riboregulator as disclosed herein, wherein the vector comprises: (a) a nucleic acid as disclosed herein that encodes an ORIENTR riboregulator, where the nucleic acid is operatively linked and under the translational control of a promoter. e.g., a constitutive promoter, or alternatively, an inducible promoter or tissue or cell-specific promoter, for transcription of the ORIENTR within a target cell and, optionally, the vector comprises (b) a nucleic acid that encodes a RNA trigger that is operably linked to and under regulatory control of a promoter (e.g., the same or different promoter operatively linked to the ORIENTR), and wherein production of the ORIENTR. in the presence of a RNA-trigger can allow the processing of one or more pri-miRNAs reduces, prevents, and/or eliminates growth and/or survival of the target cell thereby slowing, reversing, and/or eliminating the disease or condition in the human.

The amount of the one or more ORIENTR in a cell, and subsequence biogeneis of pri-miRNAs that will be effective in the treatment, inhibition, and/or prevention of cancer, infectious disease, or other disease or condition can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The systems or pharmaceutical compositions comprising an ORIENTR riboregulator, and optionally a RNA-trigger as disclosed herein can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a system on a cell line or a patient tissue sample. The effect of the system or pharmaceutical composition thereof on the cell line and/or tissue sample can be determined utilizing techniques known to those of skill in the art including, but not limited to proliferation and apoptosis assays. In accordance with the present disclosure, in vitro assays that can be used to determine whether administration of a specific ORIENTR is functional and responds to a cognate RNA-trigger, such assays include in vitro cell culture assays in which a patient tissue sample is grown in culture, and exposed to or otherwise administered an ORIENTR, in the presence or absence of a RNA-trigger, and the effect of such ORIENTR upon the tissue sample is observed.

By way of an illustrative example only, an ORIENTR and system as disclosed herein can be used to treat a subject with a neurodegenerative disease. In neurodegeneration diseases, cells undergo transition from healthy state to disease affected state. A precise treatment for disease affected cells to slow down disease progression is of great value.

For exemplary purposes only, the compositions, methods and systems comprising an ORIENTR riboregulator as disclosed herein can be used to treat a subject with Huntington's disease. Huntington disease is caused by a CAG trinucleotide repeat expansion in the huntingtin gene (HTT). The repeat instability causes progressive repeat size expansion in neuron cells which leads to toxicity from both RNA and protein levels. The huntingtin-transcript-lowing approach is of great therapeutic interest to decrease toxicity from both RNA and protein levels, however the loss of HTT function is a concern for proper neuronal cell development and function. To address this problem, an ORIENTR can serve as a sensor and actuator that only disease affected neuron cells with large CAG-expansions produces HTT-targeting miRNA. That is, for example, in some embodiments, an ORIENTR that comprises a toehold region that is responsive, or can complementary bind to RNA-target comprising the CAG-expansion in the HTT can induce the biogenesis of a miRNA in an output domain that targets and results in the degradation of the HTT mRNA that comprises CAG repeats. In some embodiments, the output domain of an ORIENTR to treat Huntington's disease can be selected from any miRs disclosed in U.S. Pat. No. 11,371,044, which is incorporated herein in its entirety by reference. In some embodiments, the guide sequence to target huntingtin gene suppression can be selected from any siRNA target sequence disclosed in International Patent application or US patent applications: WO2005105995, US20090186410, US20110172291, US2008/0015158, WO2008134646, each of which are incorporated herein in their entirety by reference.

Similarly and as an exemplary example, the compositions, methods and systems comprising an ORIENTR riboregulator as disclosed herein can be used to treat a subject with the in Alzheimer's disease. In Alzheimer's disease, tau protein knockdown is a promising therapeutic approach due to the disease causative role of tau aggregation in neuron cells. However, given the intricate roles of tau in many neuronal pathways, the potential adverse effects of the tau reduction approach remain unclear. A treatment strategy administering an ORIENTR to a subject would be able to provide treatment specificity to decrease side effects, activating only in disease affected neuronal cells, and can be used to generate tau-reducing miRNA, giving more precise treatment in target cells while avoiding actuation in healthy neurons. For example, in some embodiments, an ORIENTR that comprises a toehold region that is responsive, or can complementary bind to tau RNA-target can induce the biogenesis of a miRNA, e.g., a tau-miRNA in an output domain that targets and results in the degradation of the tau.

In another exemplary embodiment, the compositions, methods and systems comprising an ORIENTR riboregulator as disclosed herein can be used to for the treatment of cancer. Aberrant small nucleolar RNA (snoRNA) expressions are found to be prevalent in many cancer types. For example, SNORA3 and SNORA43 overexpressed in lung cancer stem cells. Accordingly, in some embodiments, these snoRNA can be used as RNA-triggers for an ORIENTR to initiate miRNA expression that targets the apoptosis pathway to induce cancer cell apoptosis.

In another exemplary embodiment, the compositions, methods and systems comprising an ORIENTR riboregulator as disclosed herein can be modified such that the output domain comprises antisense oligonucleotides (ASO) to a disease target. In particular, in the United Stated, the FDA has approved multiple ASO, which can be incorporated into the output domain and their production induced by a specific RNA-trigger, thus enabling a RNA interference (RNAi) that is mediated by a specific RNA-trigger activating the ORIENTR. In alternative embodiments, ASO can also modified and designed as a RNA-trigger to initiate ORIENTR actuation to produce a miRNA for a target gene knockdown. For example, Spinraza, an ASO for the treatment of spinal muscular atrophy, can be repurposed to serve as a RNA-trigger for an ORIENTR to produce miRNA targeting tau expression. Accordingly, in some embodiments, an ASO that serves as a RNA-trigger can be used to induce RNAi provides further temporal control over gene reduction and to further improve treatment safety.

In some embodiments, diseased cells may be targeted by ORIENTR riboregulators as disclosed herein, provided that diseased cells can be distinguished from non-diseased cells. In some embodiments, diseased cells can be distinguished by overexpression of endogenous receptors, or by expression of disease-specific receptors. In epithelial cancer cells, the folate receptor is overexpressed, while in HIV-infected cells, the HIV-1 glycoprotein Env is expressed. In other embodiments, diseased cells can be distinguished by changes in the intercellular serum pH. For example, elevated pH in local extracellular environment may signal disease. In tumors, heterogeneous perfusion impairs removal of acidic metabolic waste and requires cells to have higher levels of anaerobic glycolysis. In other embodiments, properties of intracellular proteins may indicate that a cell is diseased. Virus or cancer proteins may be misfolded, or protein expression levels may change. In cancerous cells, high levels of thymidylate synthase (TS) are indicative of malignancy and correlate with poor survival rates in patients. TS is also expressed at elevated levels in cells that have been transformed with tumor viruses. Finally, irregular morphologies of cells or cellular structures often correlate with disease. Irregular chromatin distribution in the nucleus, an increased nucleus to cytoplasm (N:C) ratio, and other apical morphologies may signal cell malignancy. These identifying characteristics of diseased cells can lead to changes in the transcriptome that can be detected by ORIENTRs to stimulate biogenesis of an output miRNA.

In some embodiments, a desired ORIENTR riboregulator is transfected by methods known in the art into a culture of stem cells and/or transformed cells.

In some embodiments, the ORIENTR riboregulator technology platforms disclosed herein may be useful in antimicrobial applications. For example, ORIENTR riboregulators may be used against *Mycobacterium tuberculosis* (TB). TB uses secreted factors to alter the early phagosome of the host macrophage, creating a hospitable environment for replication and potentially for a latent infection (LTBI). Subsequently, enveloped TB bacteria secrete additional factors to block fusion of the phagosome with lysosomes, which normally forms a phagolysosome. TB secreted factors include protein kinases such as PknG, found in the macrophage cytoplasm, secretory protein ESAT-6, CFP-10, and SapM which has PI3P phosphatase activity and interacts with PI3P on the cytoplasmic leaflet of the phagosome.

ORIENTR riboregulators may also be used to combat infection by the malaria parasite. The sporozoites or hypnozoites establish or maintain an infection by secreting proteins into a parasitophorous vacuolar membrane (PVM). Proteins incorporated into the PVM membrane can be displayed in the host's cytoplasm. UIS3 and UIS4 are two examples of transmembrane proteins that may be used. Parasites such as *P. vivax* and *P. ovale* can produce hypnozoites in liver cells, causing a liver infection that can become active months or years later. As a defense, signal-activated polynucleotides, designed as degradation-based platforms are transfected into liver cells. Ribozyme aptamers built in the ORIENTR riboregulators binds to the cytoplasmic side of UIS3 or UIS4 proteins in the PVM transmembrane. This binding activates the signal-activated polynucleotide via a degradation mechanism, through conformational changes and degradation of sequences on the signal-activated polynucleotide. This activity induces apoptosis by production of caspases with signal-activated IRES sequences, or by RNAi-mediated downregulation of pro-apoptotic proteins. Bcl-2 is one potential target. Apoptosis of infected cells subverts necrosis and kills the parasites.

b) ORIENTR Riboregulators for the Treatment of Cancer

The presence of mutated mRNA sequences, changes in the levels of certain miRNAs, the presence of normally dormant transcription factors and or other changes in the transcriptome are associated with all cancers. Studies have shown that patterns in the expression of mutated mRNAs, normally dormant developmental factors, and the level of miRNA expression could be further correlated with the likelihood of metastasis in some cancers. ORIENTRs allows the delivery of small RNAi structures using existing or future methods for siRNA delivery to cancer cells. Upon entry into the cytoplasm or nucleus, the structures detect the presence of various cancer markers or signals in the transcriptome and initiate RNA interference.

In traditional RNA interference (RNAi), the target gene must be a gene that cancer cells depend on to a degree more than healthy cell, or a gene that has a mutated sequence in cancer. One example is a mutated K-RAS mRNA. This allows RNAi therapy to interfere with the growth and development of cancer cells but may not allow RNAi to directly repress genes critical to the cancer cell's survival. In contrast, ORIENTR regulated RNAi can detect the transcriptome cancer markers and activate to induce RNAi against critical cellular processes, thereby directly inducing apoptosis, inflammatory responses, or other responses that more directly destroy the cancer cell. Furthermore, since the ORIENTR as disclosed herein can be triggered by a RNA-trigger present only in cancer cells, it is possible to deliver a much higher dose of therapeutic ORIENTR structures using methods such as nanoparticle transfection through the Enhanced Uptake and Retention effect without causing harm to organs where nanoparticles or other delivery structures tend to accumulate. Overall, these advantages could lead to dramatically increased and more selective lethality against cancer cells.

Several genes are likely candidates as target genes for the pri-miRNA in the output domain of the ORIENTR. Examples comprise targetable cancer markers, such as K-RAS, mutations of which have been associated with pancreatic, breast, and lung cancers; fusion oncogenes; viral RNAs corresponding to viruses that may induce sarcomas; miRNAs that are reported to be upregulated in solid tumors (see Volinia et al, PNAS, 103, 2257; Ma et al, Nature, 449, 682; He et al, Nature, 435, 828), such as the mir-17-92 cluster, mir-10a, mir-21, and more. Accordingly, the pri-miRNA can target any one KRAS.

Novel small and microRNA targets in human cancers given in the following papers have been described in recent publications. Unique targets may be found for human cervical cancer (Liu, Pourmand, Patterson, and Fire, Cancer Res, 67, 6031 (2007)), chronic lymphocytic leukemia (Borkhardt, Arndt, Fuchs, Uta, and Tuschl, Tom, The New England Journal of Medicine, 354, 524 (2006) and Calin et al, The New England Journal of Medicine, 353, 1703 (2005)).

Developmental transcriptional factors such as Twist may be targeted by ORIENTR regulated RNAi. Data from a recent study (Cell, 117, 927 (2004)) suggests that developmental transcription factors are reactivated in metastatic cancer cells. Twist and other developmental transcription factors may be expressed in normal cells of one body organ but only in cancer cells of another body organ. Thus, they are cancer indicators only in certain types of human cells. In some embodiments, RNAi may use a NAND (NOT-AND) gate switching mechanism that determines the cell type and the presence of abnormal developmental factors before activating RNAi.

Exemplary target genes of the miRNA in the output domain of ORIENTR for the treatment of cancer are described below.

BCL-1 (Entrez GeneID: 595) encodes the Cyclin DI protein, which acts to control G1 progression and G1/S transition. Cyclin DI forms a complex with and functions as a regulatory subunit of CDK4 or CDK6, whose activity is required for cell cycle G1/S transition. This protein has been shown to interact with tumor suppressor protein Rb and the expression of this gene is regulated positively by Rb. Mutations, amplification and overexpression of this gene, which alters cell cycle progression, are observed frequently in a variety of tumors and may contribute to tumorigenesis. Overexpression of the bcl-I gene has been found in lymphoma, leukemia, and myeloma, where it may act to accelerate the cell transit through the G1 phase of the cell cycle. Accordingly, bcl-1/Cyclin DI may be used for ORIENTR regulated RNAi. As a target, bcl-1/Cyclin DI knockdown may provide a means for controlling unchecked cell growth. As a signal polynucleotide, bcl-1 gene products may be used to target other RNAi pathways against genes during the specific time point that bcl-1 is expressed.

NADPH oxidase 4 (Nox4, Entrez Gene ID 50507) has been postulated to function in the kidney as an oxygen sensor that regulates the synthesis of erythropoietin (EPO) in the renal cortex. The gene has also been associated with pancreatic cancer, so ORIENTR regulated RNAi directed against this target could be a particularly useful therapy against pancreatic cancer, as well as other types of cancer or any other disorders associated with dysregulation of reactive oxidative species (ROS).

Mammalian lin-28 (Entrez GeneID: 79727) is a homolog of the C. elegans lin-28. In humans, lin-28 has been implicated in tumor metastasis and invasion. Low levels of Lin-28 expression are present in the other organs, but high expression may also appear selectively in tumors. Regulation of mRNA is a conserved feature of the lin-28 gene in diverse animals. The long isoform of Lin-28-B is a specific inhibitor of let-7 mRNA and Lin-28 downregulation by miR-125 involves a reduction in both translational efficiency and mRNA abundance. Therefore, modulation (e.g., inhibition) of Lin-28 expression may be used to inhibit cancer invasion and metastasis.

Pancreatic stellate cells (PaSCs) are used to repair injury in the pancreas. Examples of injury include long-term activation by oxidative stress and repetitive injury that leads, in turn, to fibrosis. In other capacities, PaSCs may aid in tumor growth and invasion of surrounding tissue. Thus, modulating the function of PaSCs may useful for inhibiting tumor growth and invasion, or controlling repair of injured tissue. General features of PaSCs in the quiescent and activate state have been characterized and compared. Notably, expression of the molecular marker a-SMA is higher in activated PaSCs than in quiescent PaSCs. Thus, a-SMA could be used as a signal to target the polynucleotides described herein to activate PaSCs.

Heat shock transcription factor 1 (HSF1, Entrez Gene ID 3297) is a heat shock transcription factor that is induced after temperature stress. HSF1 up-regulates chaperone machinery in response to cellular stress, and may play a role in cancer and neurodegeneration. In recent studies, HSF1 knockdown was shown to be selectively lethal towards cancer cells, while other studies suggest that generalized knockdown of HSF1 could lead to side effects including exacerbation of neurodegeneration. HSF1 could be a target for ORIENTR regulated RNAi, or may be useful as a signal that will activate RNAi in select cells.

Bcl-2 (Entrez GeneID 596) and the Bel family of proteins govern mitochondrial outer membrane permeabilization and are either pro-apoptotic or anti-apoptotic. Mutations in a variety of Bcl proteins have been associated with pathological conditions, including cancer. Thus, where Bcl proteins act to inhibit apoptosis, knockdown of gene or protein function is expected to induce apoptosis. Bcl-2 or other Bcl family members could serve as gene targets, or, alternately, mutant forms of the proteins could serve as signals for diseased cells or cells that are susceptible to deficits.

The target sequence need not be identical to the signal polynucleotide. In one design, the ORIENTR regulated polynucleotide is designed to hybridize to α-SMA mRNA, which displaces a duplexes formed between the signal-detecting strand and other sequences, and enables or promotes formation of a duplex between the guide sequence and the sense sequence. This duplex may be cleaved by Dicer or loaded into RISC. In this example, the guide strand comprises 21 nucleotides directed against RelA (also known as p65, Entrez GeneID 5970). RelA (p65) is a member of the NF-κB family of transcription factors, which are contribute to such cellular processes as the immune response, cell proliferation, cell differentiation. Constitutive activation of proteins from this family have been associated with many pathological conditions such as rheumatoid arthritis, inflammatory bowel syndrome, AIDS and cancer. RNAi-mediated knockdown of RelA (p65) or other NF-κB family members may be useful for treating these conditions. More specifically, the use of α-SMA as a signal polynucleotide directs the knockdown of RelA (p65) to α-SMA expressing cells.

ABCB5 (Entrez GeneID 340273) is expressed in melanocytes and a minority of melanoma cells, but recent evidence suggests that ABCB5 is a likely presence in all melanoma may be play a role in all melanoma metastasis activity. ABCB5 may be a target for ORIENTR regulated RNAi in diseases such as cancer and melanoma. As ABCB5 may be involved in multiple-drug resistance, and traditional chemotherapy regimens could enrich ABCB5+ cells, or mAb to ABCB5 may cause unwanted immune response against melanocytes. Thus, local delivery of ORIENTR regulated RNAi may be the safest treatment.

DNM3 TB proteins are expressed in a variety of cancers, including myeloid leukemia, lymphoid leukemia, follicular lymphoma, breast cancer, cervical cancer, mesothelioma, head and neck cancer, small cell lung cancer, colorectal cancer, gastric cancer, hepatocellular carcinoma, glioma, primary lymphoid leukemias, primary lymphoblastic leukemias, and more. These proteins are not necessarily present in normal tissue, and the genes encoding the proteins have novel intron sequences. Thus, DNM3 TB gene products may be useful for ORIENTR regulated RNAi, either as the signal polynucleotide that activates the RNAi pathway, or as a target for RNAi.

The secretin receptor (pp32, Entrez GeneID 6344) may be involved in cancer. In both pancreatic and liver tumors, a novel mRNA splice-form created by deletion of exon 3 and 4 has been observed. Either pp32 (Entrez GeneID 6343) or its receptor could be targets for ORIENTR regulated RNAi. pp32, which normally acts as a tumor suppressor, is located on chromosome 15, whereas pp32r1 and pp32r2 are tumorigenic and are located on chromosomes 4 and 12.

c) ORIENTR Riboregulators for the Treatment of in Viral Infection

A number of viruses utilize RNA interference at crucial stages in their life cycle or lack mechanisms for completely disabling the cellular RNA interference pathways. In some embodiments, ORIENTR can comprise a miRNA or RNAi in the output domain that can target crucial viral replication pathways to halt replication, critical cellular processes to induce apoptosis or inflammatory responses, or drug resistance pathways to increase the effectiveness of antiviral therapies. Targets for a miRNA output produced from the ORIENTR may comprise viral RNA. For example, ORIENTR may be used to target HIV associated mRNAs, miRNAs and latency transcripts in latent HIV infected cells.

As reviewed in Cullen, B. R. (2006) Viruses and microRNAs. Nature Genetics 38: S25-S30, several viruses have been shown to encode miRNA. Subsequently, RNAi could be used to induce apoptosis of infected cells. In another example, ORIENTR regulated RNAi could be activated by herpes latency-associated transcripts. For example, nuclear import signals may be used to bring the ORIENTR regulated polynucleotide to the nucleus, where RNA from the herpes virus serves as a signal to activate the polynucleotide.

In addition, latent HIV CD4+ cells show abundance of aborted mRNA transcripts, any of which may serve either as RNA-triggers as disclosed herein, or as targets for ORIENTR regulated RNAi. Further, there is a high population of HIV DNA in viral reservoirs in the gut.

d) ORIENTR Riboregulators for the Treatment of in Autoimmune Disease

In some embodiments, ORIENTR regulated RNAi may be used to detect transcriptome markers of autoimmune disease. Moreover, ORIENTR regulated RNAi may be used to induce senescence in the immune system cells involved in systematic and effective attacks on the body's own cells.

e) ORIENTR Riboregulators for Use in Cell Lines, Plant, and Animal Models

ORIENTR riboregulators may be incorporated into cell lines or into multicellular organisms. This scheme enables selective, correlated activation of RNAi against one or more targets, based on specific predetermined signals.

In some embodiments, one or more ORIENTR riboregulators may be used in combination with transgenic plants and animals, wherein RNA-triggers in the transgenic organism activate the ORIENTR to produce a miRNA of the output domain. In one embodiment, the transgene or some product of a signaling pathway modulated by the transgene is used to activate a signal-activated polynucleotide.

f) ORIENTR Riboregulators that can Produce miRNA in Response to RNA-Triggers Having Specific SNPs Discrimination of single nucleotide polymorphisms is difficult because of the small difference in the free energy of binding between two oligonucleotides that vary by only a single base. In some embodiments, a toehold domain can be used to identify a specific SNP in a trigger RNA. Strand displacement is a process that is kinetically inhibited by SNP presence in a RNA trigger. Alternatively, the toehold domain is specific for a particular SNP, thereby producing the miRNA from the output domain only when the RNA-trigger comprises the particular SNP.

In some embodiments, the toehold of the ORIENTR recognizes a RNA-trigger with a specific SNP. This way, only the RNA-trigger with the SNP results in miRNA production. In some embodiments, the target gene of the miRNA is the mRNA comprising the SNP, resulting in degradation of the mRNA comprising the specific SNP.

Methods of administration of an ORIENTR (and in some embodiments, a RNA-trigger) as disclosed herein can be delivered by vectors, and/or nanoparticles. In some embodiments, the administration of vectors (e.g., viral vectors) and/or nanoparticles such as lipid nanoparticles, include, but are not limited to, intradermal, intramuscular, intraperitoneal, intravenous, subcutaneous, intranasal, epidural, and oral routes. In some embodiments, an ORIENTR (and in some embodiments, a RNA-trigger) as disclosed herein, or compositions thereof, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

It may be desirable to administer an ORIENTR (and in some embodiments, a RNA-trigger) locally to the area in need of treatment; this may be achieved by, for example, local infusion during surgery, topical application, by injection, by means of a catheter, by means of a suppository, or by means of an implant, said implant being of a porous, non-porous, or gelatinous material, including membranes, such as sialastic membranes, or fibers.

In some embodiments, an ORIENTR (and in some embodiments, a RNA-trigger) can be delivered in a controlled release system placed in proximity of the therapeutic target, thus requiring only a fraction of the systemic dose (see, e.g., Goodson, in Medical Applications of Controlled Release 2:115-138 (1984)).

Intravenous infusion of a compositions comprising a system (e.g., an ORIENTR (and in some embodiments, a RNA-trigger) may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

In some embodiments, continuous intravenous infusion of a composition comprising a system (e.g, an ORIENTR (and in some embodiments, a RNA-trigger)) may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period. Regardless of the precise administration or infusion protocol adopted, it will be understood that continuous infusion of a composition comprising one or more ORIENTRs (and in some embodiments, a RNA-trigger) will continue until either desired efficacy is achieved or an unacceptable level of toxicity becomes evident.

VIII. Kits

The invention further provides a variety of kits. For example, the invention provides a kit comprising a plasmid, wherein a first plasmid comprises (i) a template for transcription of an ORIENTR, and (ii) a promoter located upstream of the template for transcription of the ORIENTR, and optionally a second plasmid that comprises (i) a template for transcription of a cognate (complementary) RNA-trigger element, and (ii) a promoter located upstream of the template for transcription of the RNA-trigger element. The promoters may be the same or, preferably, different. One or more of the promoters may be inducible. The plasmids may have the same or different copy numbers. The invention further provides a kit comprising a single plasmid that comprises a template for transcription of a ORIENTR element and a promoter located upstream of the template for transcription of the ORIENTR and further comprises a template for transcription of a cognate RNA-trigger element and a promoter located upstream of the template for transcription of the cognate RNA-trigger element. In certain embodiments, the plasmids comprise one or more restriction sites upstream or downstream of the template for transcription of the ORIENTR element. If downstream, the restriction sites may be used for insertion of an open reading frame of choice. The kits may further include one or more of the following components: (i) one or more inducers; (ii) host cells (e.g., prokaryotic or eukaryotic host cells); (iii) one or more buffers; (iv) one or more enzymes, e.g., a restriction enzyme; (v) nucleic acid isolation and/or purification reagents; (vi) a control plasmid lacking a ORIENTR or RNA-trigger sequence; (vii) a control plasmid containing a ORIENTR or RNA-trigger sequence or both; (viii) sequencing primers; (ix) instructions for use. The control plasmids may comprise a reporter sequence.

Some embodiments of the technology described herein can be defined according to any of the following numbered paragraphs:

1. An ORIENTR riboregulator, comprising a nucleic acid construct that is an Orthogonal RNA Interference induced by Trigger RNA (ORIENTR) molecule, the ORIENTR molecule comprising, in a 5' to 3' order:
   i. a single stranded 5' toehold domain (T1),
   ii. a fully or partially double-stranded RNA sequestering-Loop domain (SLD) comprising:
      i. a 3' sequestering arm region comprising a 5' region (S1) and a 3' region (S2),
      ii. a loop,
      iii. a 3' flanking sequence (S2'), wherein 3' flanking sequence forms a RNA duplex with a 3' region (S2) of the sequestering arm region,
      iv. a 5' basal stem (5'-BS) sequence, wherein 5' basal stem sequence forms a RNA duplex with a 5' region (S1) of the sequestering arm, and
   iii. an output domain, the output domain comprising a fully or partially double-stranded RNAi hairpin, comprising
      i. a guide strand sequence targeting a nucleic acid of interest,
      ii. a loop sequence, and
      iii. a passenger strand sequence to the guide strand sequence, where the passenger strand forms a partially or full double stranded stem with the guide strand sequence;
      iv. a 3' basal stem (3' BS) sequence, wherein 3' basal stem sequence capable of complementary base pairing with 5' basal stem sequence to form a basal stem structure that is recognized and can be bound by Drosha.
2. The ORIENTR riboregulator of paragraph 1, wherein the RNAi hairpin in the output domain is a pri-miRNA hairpin structure, and wherein the loop sequence in the output domain is an aptical loop.
3. The ORIENTR riboregulator of any of paragraphs 1-2, wherein the loop is part of a hairpin-stem loop (HSL) structure.
4. The ORIENTR riboregulator of any of paragraphs 1-3, wherein the ORIENTR further comprises a spacer sequence located 3' of 3' basal stem sequence.
5. The ORIENTR riboregulator of any of paragraphs 1-4, wherein the ORIENTR comprises a RNA Pol III terminator sequence located 3' of 3' basal stem sequence or 3' of the spacer sequence.
6. The ORIENTR riboregulator any of paragraphs 1-5, wherein 3' basal stem sequence is a single stranded RNA.
7. The ORIENTR riboregulator of any of paragraphs 1-6, further comprising a spacer sequence located 3' of 3' basal stem sequence.
8. The ORIENTR riboregulator of any of paragraphs 1-7, further comprising a small hairpin sequence (SHS) located 3' of 3' basal stem sequence, wherein SHS is capable of forming a partial or full RNA-duplex with a 3' portion of 3' basal stem sequence to form a leak-reduction motif.
9. The ORIENTR riboregulator of any of paragraphs 1-8, wherein the SHS is at least 5 bp in length, and can weakly complementary base pair with at least 5 bp of 3' basal stem sequence.
10. The ORIENTR riboregulator of any of paragraphs 1-8, wherein the ORIENTR molecule is in the ORIENTR-OFF configuration.
11. The ORIENTR riboregulator of any of paragraphs 1-10, wherein in the presence of a RNA-trigger sequence, the ORIENTR molecule is reconfigured to comprise a secondary structure, in a 5' to 3' order:
    a. a RNA duplex comprising 5' toehold domain (T1) and S1 and S2 regions of 3' sequestering arm duplexed with a cognate RNA sequence of a RNA-trigger sequence,
    b. a single stranded 3' flanking sequence (S2'), and
    c. a pri-miRNA scaffold comprising a fully or partially double stranded RNA duplex comprising, in a 5' to 3' order:
       i. 5' basal stem (5'-BS) sequence,
       ii. the output domain, the output domain comprising a fully or partially double-stranded RNAi hairpin, comprising the guide strand sequence targeting a nucleic acid of interest, the loop sequence, and the passenger strand sequence, and
       iii. 3' basal stem (3'-BS) sequence, wherein 5' basal stem sequence and 3' basal stem sequence exist in a RNA-duplex that serves as a basal stem structure that can be recognized and bound by Drosha.
12. The ORIENTR riboregulator of paragraph 11, wherein the ORIENTR molecule is in the ORIENTR-ON configuration.
13. The ORIENTR riboregulator of any of paragraphs 1-12, wherein 5' basal stem sequence is at least 11bp, and 3' basal stem sequence is at least 11bp.
14. The nucleic acid of paragraph 13, wherein the RNA-duplex formed by 5' basal stem sequence and 3' basal stem sequence is an imperfect RNA-duplex basal stem structure that can be recognized and bound by Drosha.
15. The ORIENTR riboregulator of any of paragraphs 11-14, wherein the RNA trigger comprises a T1* region, a S1* region and a S2* region, wherein the T1* region can complementary base pair with the toehold region T1 of the ORIENTR molecule, the S1* can complementary base pair with the S1 region of 3' sequestering arm sequence of the ORIENTR molecule, and the S2* can complementary pair with the S2* region of 3' sequestering arm sequence of the ORIENTR molecule.
16. The ORIENTR riboregulator of any of paragraphs 11-16, wherein the RNA trigger further comprises a stability hairpin at the 5' end.
17. The ORIENTR riboregulator of any of paragraphs 11-16, wherein the RNA trigger comprises, in a 5' to 3' orientation, a small stabilizing hairpin, a S2* region, a S1* region and a T1* region.
18. The ORIENTR riboregulator of any of paragraphs 11-17, wherein the T1*, S1* and S2* regions of the RNA trigger together is a RNA nucleotide sequence is between 9-50 nucleotides.
19. The ORIENTR riboregulator of paragraph 16, wherein the stability hairpin is a CRISPR RNA (crRNA) hairpin.
20. The nucleic acid of paragraph 19, wherein the crRNA hairpin is a rfxCas13d scaffold hairpin, or can be bound by dCas13d.
21. The ORIENTR riboregulator of any of paragraphs 1-20, wherein 5' toehold domain (T1) and the S1 or S2 regions, or both, 3' sequestering arm is a synthetic sequence and cognate RNA sequence of a RNA-trigger sequence is a synthetic sequence.
22. The ORIENTR riboregulator of any of paragraphs 1-20, wherein 5' toehold domain (T1) and the S1 or S2 regions, or both, 3' sequestering arm can form a double-stranded duplex with a cognate RNA sequence of a RNA-trigger sequence that is an endogenous RNA sequence.

23. The ORIENTR riboregulator of any of paragraphs 11-22, wherein endogenous RNA sequence is selected from the group consisting of: a tissue specific RNA sequence, a disease specific RNA sequence, an environmental RNA sequence, a developmental RNA sequence, a temporal RNA sequence, a cell-cycle specific sequence.

24. A system comprising:
   a. The ORIENTR riboregulator of any of paragraphs 1-11, and
   b. a RNA-trigger sequence.

25. The system of paragraph 24, wherein the RNA trigger comprises a T1* region, a S1* region and a S2* region, wherein the T1* region can complementary base pair with the toehold region T1 of the ORIENTR molecule, the S1* can complementary base pair with the S1 region of 3' sequestering arm sequence of the ORIENTR molecule, and the S2* can complementary pair with the S2* region of 3' sequestering arm sequence of the ORIENTR molecule.

26. The system any of paragraphs 24 or 25, wherein the RNA trigger further comprises a stability hairpin at the 5' end.

27. The system any of any of paragraphs 24-26, wherein the RNA trigger comprises, in a 5' to 3' orientation, a small stabilizing hairpin, a S2* region, a S1* region and a T1* region.

28. The system any of any of paragraphs 24-27, wherein the T1*, S1* and S2* regions of the RNA trigger together is a RNA nucleotide sequence is between 9-50 nucleotides.

29. The system any of paragraph 26, wherein the stability hairpin is a CRISPR RNA (crRNA) hairpin.

30. The system any of paragraph 29, wherein the crRNA hairpin is a rfxCas13d scaffold hairpin, or can be bound by dCas13d.

31. The system of any of paragraphs 24-30, wherein 5' toehold domain (T1) and the S1 or S2 regions, or both, 3' sequestering arm is a synthetic sequence and cognate RNA sequence of a RNA-trigger sequence is a synthetic sequence.

32. The system of any of paragraphs 24-31, wherein 5' toehold domain (T1) and the S1 or S2 regions, or both, 3' sequestering arm can form a double-stranded duplex with a cognate RNA sequence of a RNA-trigger sequence that is an endogenous RNA sequence.

33. The system of any of paragraphs 24-32, wherein endogenous RNA sequence is selected from the group consisting of: a tissue specific RNA sequence, a disease specific RNA sequence, an environmental RNA sequence, a developmental RNA sequence, a temporal RNA sequence, a cell-cycle specific sequence.

34. A vector comprising a first promoter operatively linked to a nucleic acid sequence encoding the ORIENTR construct of any of paragraphs 1-11.

35. The vector of paragraph 34, further comprising a nucleic acid encoding a RNA trigger sequence, wherein the nucleic acid encoding the RNA trigger sequence is operatively linked to the first promoter, or a second promoter.

36. The vector of paragraph 34, wherein the RNA trigger comprises a T1* region, a S1* region and a S2* region, wherein the T1* region can complementary base pair with the toehold region T1 of the ORIENTR molecule, the S1* can complementary base pair with the S1 region of 3' sequestering arm sequence of the ORIENTR molecule, and the S2* can complementary pair with the S2* region of 3' sequestering arm sequence of the ORIENTR molecule.

37. The vector of any of paragraphs 34 to 36, wherein the RNA trigger further comprises a stability hairpin at the 5' end.

38. The vector of any of paragraphs 34 to 37, wherein the RNA trigger comprises, in a 5' to 3' orientation, a small stabilizing hairpin, a S2* region, a S1* region and a T1* region.

39. The vector of any of paragraphs 34 to 38, wherein the T1*, S1* and S2* regions of the RNA trigger together is a RNA nucleotide sequence is between 9-50 nucleotides.

40. The vector of any of paragraphs 34 to 39, wherein the stability hairpin is a CRISPR RNA (crRNA) hairpin.

41. The vector of paragraphs 40, wherein the crRNA hairpin is a rfxCas13d scaffold hairpin, or can be bound by dCas13d.

42. The vector of any of paragraphs 34-41, wherein the first promoter is selected from any of: a constitutive promoter, a tissue specific promoter, inducible promoter, cell cycle dependent promoter, cell stress dependent promoter, inflammation inducible promoter, hypoxia induced promoter.

43. The vector of any of paragraphs 34-42, wherein the first or second promoter, or both, is a human U6 promoter.

44. The vector of any of paragraphs 34-43, wherein the first promoter is a different promoter to the second promoter.

45. The vector of any of paragraphs 34-44, wherein the vector is a viral vector.

46. The vector of any of paragraphs 34-45, wherein the viral vector is selected from the group consisting of: AAV, Adenovirus vector, lentivirus vector and HSV.

47. A cell comprising the ORIENTR riboregulator of any of paragraphs 1-23, or a system of any of paragraphs 24-33, or a vector of any of paragraphs 34-46.

48. The cell of paragraph 47, wherein the cell is a mammalian cell.

49. The cell of paragraph 47 or 48, wherein the cell is human cell.

50. The cell of any of paragraphs 47-49, wherein the cell is a living cell.

51. The cell of any of paragraphs 47-50, wherein the cell is an in vivo cell.

52. The cell of any of paragraphs 47-51, wherein the cell is present in a human subject in need of treatment.

53. A method for treating a subject with a disease or disorder, the method comprising administering a cell of any of paragraphs 47-52 to the subject, or administering an ORIENTR molecule of any of paragraphs 1-23 to the subject, or administering a vector of any of paragraphs 34-46 to the subject, wherein the subject is in need of treatment and wherein the subject in need of treatment is in need of RNA interference (RNAi) or a miRNA to reduce or repress a target nucleic acid in a cell in the subject.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used herein, the terms "synthetic," "engineered," and "genetically engineered" are used interchangeably and refer to the aspect of having been manipulated by the hand of man. The terms encompass a non-naturally occurring nucleic acid molecule that has been created or modified by the hand of man (e.g., using recombinant DNA technology) to differ from the sequence of the nuclease as it exists in nature, or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. In some embodiments, a synthetic nucleic acid sequence is a chimeric molecule comprising a collection of joined nucleic acid molecules which are not found joined in nature, and can comprise one or more artificial sequences between the joined nucleic acid sequences. A cell that contains a synthetic or engineered nucleic acid is considered to be an engineered cell. As is common practice and is understood by those in the art, progeny and copies of an engineered polynucleotide and/or polypeptide are typically still referred to as "engineered" even though the actual manipulation was performed on a prior entity.

As used herein, the term "nucleotide" or "nt" refers to a ribonucleotide or deoxyribonucleotide.

As used herein, the term "base pair" or "bp" is a fundamental unit of a double stranded nucleic acid, comprising two nucleotides or nucleobases that pair together by weak hydrogen bonds. As disclosed herein, two nucleotides from the same nucleotide strand can complementary base pair in cis, or alternatively, two nucleotides from different nucleic acid strands can complementary base pair in trans. In some embodiments, the complementary base pairing of a stretch of nucleotides with another stretch of nucleotides from the same nucleic acid strand can form a stem structure (i.e., secondary structure) via cis-base pairing. In some embodiments, the complementary base pairing of a stretch of nucleotides from one nucleic acid strand with a stretch of complementary bases from a different nucleic acid strand can form a stem structure via as trans-base pairing. In some embodiments, the RNA-trigger can trans-base pair with the RNA-trigger sensing domain. By way of example, in some embodiments, e.g., the S1 and 5' basal stem sequence of the ORIENTR can cis-base pair to form a stem structure, and 5' basal stem sequence can cis-base pair with 3' basal stem sequence to form a basal stem structure.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archacosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylamino nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide. The term "polynucleotide" refers to polymers of two or more nucleotides, and includes, but is not limited to, DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

The term "ribonucleotide" and the term "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

As used herein, the term "non-complementarity" refers to refers to an entity in a double stranded region of an RNA composition (wherein the double strand nature of the RNA composition may arise from intramolecular hybridization within one RNA molecule and/or arise from intermolecular hybridization between two RNA molecules) that comprises non-complementary nucleotides between the two strands of the double stranded region. Thus, the region may be defined as a region of non-complementary nucleotides flanked by regions of double stranded RNA. In specific embodiments, the length of non-complementation is at least about 5 nucleotides. In other specific embodiments, the junction between the bubble and double stranded region comprises at least two T's. The terms "bubble" or "bulge" may also be used for the term "region of non-complementarity." It will be understood that the terms "bubble" and "bulge" imply no specific shape of said region, although in some embodiments it is shaped as a bubble. Complementarity of two sequences is generally determined by dividing the total number of nucleotides that participate in complementary base pairs (GC, AU, AT) when the sequences are aligned to produce the maximum number of complementary base pairs, counting all nucleotides in the two sequences (including those in bulges, mismatches, or inner loops) by the total number of nucleotides contained in both sequences. For example, consider two sequences of 19 and 20 nucleotides in length in which alignment to produce the maximum number of complementary base pairs results in 16 base pairs, 1 inner loop of 2 nucleotides, 1 mismatch, and 1 bulge (in the sequence with 20 nucleotides). The percent complementarity of the two sequences is [(16+17)/39]100. It will be appreciated that complementarity may be determined with respect to the entire length of the two sequences or with respect to portions of the sequences. As used herein, two sequences are considered "substantially complementary" herein if their complementarity is at least 50%.

The term "complementary" refers to the liability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Partial complementarity, also referred to as "imperfect" base pairing refers to the situation in which some, but not all, nucleotide units of two strands can hydrogen bond with each other. For example, two strands are at least partially complementary when at least 6-7 base pairs can be formed over a stretch of about 19-25 nucleotides. Sequences are said to be "complementary" to one another when each sequence is the (partial or complete) reverse complement (RC) of the other. For example, the sequence 5' GATC 3' is perfectly complementary to its reverse complement sequence 3' CTAG 5'. Sequences can also have wobble base pairing.

The term "duplex" refers to a double stranded structure formed by two complementary or substantially complementary polynucleotides that form base pairs with one another, including Watson-Crick base pairs and U-G wobble pairs, which allows for a stabilized double stranded structure between polynucleotide strands that are at least partially complementary. The strands of a duplex need not be perfectly complementary for a duplex to form i.e. a duplex may include one or more base mismatches.

A single polynucleotide molecule can possess antiparallel and complementary polynucleotide strands capable of forming a duplex with intramolecular base pairs. Such polynucleotides frequently have a stem-loop structure where the strands of the stem are separated by a loop sequence (which is predominantly single stranded) and are thus able to adopt a mutually antiparallel orientation. Stem-loop structures are well known in the art. Pri-miRNAs often have one or more stem-loop structures in which the stem includes a mature strand-star strand duplex.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or disorder. A subject can be male or female.

A subject can be one who has been previously diagnosed with or identified as suffering from or having a condition in need of treatment or one or more complications related to such a condition, and optionally, have already undergone treatment for a condition to be treated, or the one or more complications related to a condition to be treated.

A "subject in need" of treatment for a particular condition can be a subject having that condition, diagnosed as having that condition, or at risk of developing that condition.

The term "effective amount" as used herein refers to the amount of (a) fusion protein, (b) RNA molecule, (c) nucleic acid, (d) vector, (e) system, (f) cell, (g) composition, and/or (g) pharmaceutical composition needed to alleviate at least one or more symptom of a disease or disorder in a subject in need thereof, and relates to a sufficient amount to provide the desired effect. The term "therapeutically effective amount" therefore refers to an amount of (a) fusion protein, (b) RNA molecule, (c) nucleic acid, (d) vector, (e) system, (f) cell, (g) composition, and/or (g) pharmaceutical composition that is sufficient to provide a particular effect, e.g., anti-cancer, e.g., anti-infectious disease, effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested by one of ordinary skill in the art to confirm that a desired activity, e.g. elimination of a STOP codon and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a polypeptide which retains at least 50% of the wild-type reference polypeptide's activity. A functional fragment can comprise conservative substitutions of the sequences disclosed herein.

In some embodiments, the polypeptide described herein can be a variant of a polypeptide sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a protein or fragment thereof that retains activity of the native or reference polypeptide. A wide variety of, for example, PCR-based, site-specific mutagenesis approaches are known in the art and can be applied by the ordinarily skilled artisan to generate and test artificial variants.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

A variant amino acid sequence can be at least 50%, at least 60%, at least 70%, at least 80%, at least 90%, at least 91%, at least 92%, at least 93%, at least 94%, at least 95%, at least 96%, at least 97%, at least 98%, at least 99%, or more, similar to a native or reference sequence. As used herein, "similarity" refers to an identical amino acid or a conservatively substituted amino acid, as described herein. Accordingly, the percentage of "sequence similarity" is the percentage of amino acids which is either identical or conservatively changed; e.g., "sequence similarity"=(% sequence identity)+ (% conservative changes). It should be understood that a sequence that has a specified percent similarity to a reference sequence necessarily encompasses a sequence with the same specified percent identity to that reference sequence. The skilled person will be aware of various computer programs, using different mathematical algorithms, that are available to determine the identity or similarity between two sequences. For instance, use can be made of a computer program employing the Needleman and Wunsch algorithm (Needleman et al. (1970)); the GAP program in the Accelrys GCG software package (Accelrys Inc., San Diego U.S.A.); the algorithm of E. Meyers and W. Miller (Meyers et al. (1989)) which has been incorporated into the ALIGN program (version 2.0); or more preferably the BLAST (Basic Local Alignment Tool using default parameters); see e.g., U.S. Pat. No. 10,023,890, the content of which is incorporated by reference herein in its entirety.

As used herein, the phrase "maintains the same function", when used in reference to an enzyme, catalyzes the same reaction as a reference enzyme. When used in reference to an ADAR or AR, it changes an A to an I in the same molecule, substance, or factor.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. A wide variety of, site-specific mutagenesis approaches, e.g., Kunkel's method, cassette mutagenesis, PCR site-directed mutagenesis (e.g., traditional PCR, primer extension, or inverse PCR), whole plasmid mutagenesis, in vivo site-directed mutagenesis, CRISPR/Cas-guided mutagenesis, are known in the art and can be applied by the ordinarily skilled artisan to introduce mutations into specific nucleic acid loci. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); Braman, Jeff, ed. (2002) In Vitro Mutagenesis Protocols, Methods in Molecular Biology, Vol. 182 (2nd ed.); Khudyakov and Fields (2002), Artificial DNA: Methods and Applications, CRC Press; Hsu et al. (2014), Cell 157 (6): 1262-78; Cerchione et al. (2020) PLOS ONE 15 (4): e0231716; and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA, including closed ended DNA (ceDNA) or other circular DNA systems. Suitable RNA can include, e.g., mRNA and circular RNA constructs.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

The term "Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5'UTR) or "leader" sequences and 3' UTR or "trailer" sequences, as well as intervening sequences (introns) between individual coding segments (exons).

In some embodiments, the methods described herein relate to measuring, detecting, or determining the level of at least one marker. As used herein, the term "detecting" or "measuring" refers to observing a signal from, e.g., a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes a substance, such as a polypeptide or nucleic acid that is not naturally found or expressed in a given cell in its natural environment.

As used herein, the term "heterologous" refers to that which is not endogenous to, or naturally occurring in, a referenced sequence, molecule (including e.g., a protein), virus, cell, tissue, or organism. For example, a heterologous sequence of the present disclosure can be derived from a different species, or from the same species but substantially modified from an original form. Also for example, a nucleic acid sequence that is not normally expressed in a cell or a virus is a heterologous nucleic acid sequence with regard to that cell or virus. The term "heterologous" can refer to DNA, RNA, or protein that does not occur naturally as part of the organism in which it is present or which is found in a location or locations in the genome that differ from that in which it occurs in nature. It is DNA, RNA, or protein that is not endogenous to the virus or cell and has been artificially introduced into the virus or cell.

The term "target RNA" refers to a specific RNA that is targeted by the RNAi pathway, resulting in a decrease in the functional activity of the RNA. In some cases, the RNA target is a mRNA whose functional activity is its ability to be translated. In such cases, the RNAi pathway will decrease the functional activity of the mRNA by translational attenuation or by cleavage. In the instant disclosure, target RNAs are targeted by non-naturally occurring miRNAs. The term "target" can also refer to DNA.

The term "endogenous miRNA" refers to a miRNA produced in an organism through transcription of sequences that naturally are present in the genome of that organism. Endogenous miRNA can be localized in, for example introns, open reading frames (ORFs), 5' or 3' untranslated regions (UTRs), or intergenic regions. The organism which produces an endogenous miRNA may be, without limitation, human (and other primates), mouse, rat, fly, worms, fish or other organisms that have an intact RNAi pathway.

In some embodiments, a nucleic acid as described herein is comprised by a vector. In some of the aspects described herein, a nucleic acid sequence as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine.

In some embodiments of any of the aspects, the cells can be maintained in culture. As used herein, "maintaining" refers to continuing the viability of a cell or population of cells. A maintained population of cells will have at least a subpopulation of metabolically active cells.

As used herein, the term "specific binding" refers to a chemical or physical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeck, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in the nucleic acid construct structure (e.g., the secondary structure) of the ORIENTR without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Materials and Methods

ORIENTR Computational Design

Designs for the ORIENTR and triggers were generated using the NUPACK complex design package[32], which enabled simultaneous structural optimization of the ORIENTR, trigger and trigger-ORIENTR complex. The prevented sequences were AAAA, CCCC, GGGG, UUUUU, KKKKKK, MMMMMMM, RRRRRRR, SSSSSSS, WWWWWWW and YYYYYYY (SEQ ID NOs: 78-87 respectively). The test tube capability or pseudoknot setting were not used in the designs. See Table 1 for the NUPACK design script used for generating the ORIENTRs.

TABLE 1

Parameters for the NUPACK complex design for ORIENTER

| | Parameters |
|---|---|
| General template configuration | material = RNA<br>temperature = 37<br>trials = 10<br>structure Hpin = U18 D13(U1 D8(U2 D10 U8 U2)U1)U1 D9(U2 D8 U23 U2) U30<br>structure Trigger = U3 D8 U6 U3 U37 U6<br>structure Complex = U3 D37(U2 D10 U8 U12 D6(U1 D4(U2 D9(U2 D8 U23 U2)U2)U1)U17 + U3 D8 U6 U3)U6 |
| Elements | domain preG = GGG<br>domain stem_loop = N30<br>domain trig = N37<br>domain Flank5 = N24<br>domain guide = ACCGUGUUGCUACAGCUAUAAG (SEQ ID NO: 7)<br>domain Loop = UAGUGAAAUAUAUAUUAAA (SEQ ID NO: 8)<br>domain passenger = CAUAUAGCUGAUGCAACACGGA (SEQ ID NO: 9)<br>domain Flank3 = N12GAUACAGCAACUUUUUU (SEQ ID NO: 10)<br>domain CapHp = N22<br>domain spacer = N3<br>domain pol_III_term = UUUUUU (SEQ ID NO: 11) |
| ORIENTR INACTIVE configuration | Hpin.seq = preG trig stem_loop Flank5 guide Loop passenger Flank3 |
| TRIGGER configuration | Trigger.seq = preG CapHp spacer trig* pol_III_term |
| ORIENTR-TRIGGER configuration (ORIENTR-Active confirmation) | Complex.seq = preG trig stem_loop Flank5 guide Loop passenger Flank3 preG CapHp spacer trig* pol_III_term |
| | Hpin.stop = 10<br>Trigger.stop = 10<br>Complex.stop = 10<br>prevent = AAAA (SEQ ID NO: 78), CCCC (SEQ ID NO: 79), GGGG (SEQ ID NO: 80), UUUUU (SEQ ID NO: 81), KKKKKK (SEQ ID NO: 82), MMMMMMM (SEQ ID NO: 83), RRRRRRR (SEQ ID NO: 84), SSSSSSS (SEQ ID NO: 85), WWWWWWW (SEQ ID NO: 86), YYYYYYY (SEQ ID NO: 87) |
| Positive control pri-miRNA sequence | #Positive priRNA =<br>GAACUGACAUACUUGUUCCACUCACCGUGUUGCUACAGCUAUAAGU<br>AGUGAAAUAUAUAUUAAACAUAUAGCUGAUGCAACACGGAUAGUGU<br>GACAGGGAUACAGCAACUUUUUU (SEQ ID NO: 12) |

Plasmid Construction

ORIENTR and trigger plasmids were constructed by site-directed mutagenesis (NEB Catalog No. E0054S). A Bluescript SK plasmid with a human U6 promoter was linearized by PCR with primers containing the insert fragment, and then sealed back by blunt end joining. The luciferase reporter plasmid was generated from the pmir-GLO Dual-Luciferase miRNA Target Expression Vector (Promega catalog No. E1330) by inserting two miR-HSUR4 target sites between SacI and NheI at 3' end of the firefly luciferase gene. For generation of the GFP reporter plasmid, two miR-HSUR4 target sites were inserted into pTYF-U6-stuffer-PGK-EGFP via KpnI sites.

Cell Culture and Transfection

HEK 293T cells were cultured in DMEM with 1% penicillin and streptomycin, and 10% fetal bovine serum at 37° C. with 5% $CO_2$. For plasmid transfection experiments, $2.5 \times 10^5$ cells/well of HEK 293T cells were seeded in 12-well plates. For GFP reporter assay, 1.4 µg of plasmids (0.4 µg ORIENTR plasmid, 0.8 µg trigger plasmid, 0.2 µg GFP reporter plasmid) were transfected into one well with 2.5 µL Lipofectamine 3000 (Invitrogen) according to the manufacturer's instructions. For dCas13d experiments, 1.4 µg of plasmids (0.4 µg ORIENTR plasmid, 0.8 µg trigger plasmid, 0.2 µg dCas13d plasmid) were transfected into one well. Total RNA was extracted by the Trizol reagent (Invitrogen, L3000015) 48 hr after transfection. Northern blots were used to detect target RNAs. Northern blots using near-infrared probes was performed as described previously[41].

Luciferase Assay

The ORIENTR plasmid, trigger plasmid, and luciferase reporter plasmid were transfected into HEK293T cells. The luciferase assay was performed with Dual-Glo® Luciferase Assay System from Promega (Catalog No. E2920) according to manufacture protocol. Luciferase signal was read with a plate reader (BMG Labtech, CLARIOstar), and firefly luciferase was normalized by Renilla luciferase. Firefly luciferase signal was then normalized by signal from RNAi (—) control.

Example 1

Herein the inventors demonstrate a conditional RNAi system that functions robustly in mammalian cells and responds to specific RNA stimuli by harnessing cis-regulatory RNA elements to control recognition by the Microprocessor. The system, referred to herein as Orthogonal RNA Interference induced by Trigger RNA (ORIENTR), consists of a conditional pri-miRNA that requires binding of a cognate trigger RNA to form an active Microprocessor substrate that can in turn be processed into miRNA for induced target gene suppression. In the absence of the trigger RNA, the conditional pri-miRNA adopts an inactive secondary structure that precludes Microprocessor recognition. The inventors discovered the sequence and structural requirements for a functional pri-miRNA scaffold, and identified functional orthogonal ORIENTR devices in human cells. The inventors demonstrate herein the use of deactivated CRISPR nuclease dCas13d to facilitate RNA-RNA interaction, as well as nuclear localization for improved performance.

Importantly, the ORIENTRs device and system disclosed herein completely decouple the trigger RNA sequence from output miRNA sequence such that an arbitrary RNA input can be used to silence any desired mRNA. Accordingly, the inventors demonstrate a ORIENTRs device and system as disclosed herein for establishing programmable conditional RNAi synthetic circuits in mammalian cells.

RNA interference (RNAi) is a powerful tool for sequence-specific knockdown of gene expression in therapeutic and research applications. However, spatiotemporal control of RNAi is required to decrease nonspecific targeting, potential toxicity, and allow targeting of essential genes. Herein the inventors describe a class of de-novo-designed RNA switches that enable sequence-specific regulation of RNAi in mammalian cells. Using cis-repressing RNA elements, the inventors engineered RNA devices that only initiate microRNA biogenesis in response to the binding of a cognate trigger RNA. The inventors demonstrate that this conditional RNAi system, termed Orthogonal RNA Interference induced by Trigger RNA (ORIENTR), provides up to 14-fold increases in miRNA biogenesis upon activation in orthogonal libraries. The inventors show that integration of ORIENTR triggers with deactivated Cas13d enhances dynamic range up to 31-fold. ORIENTRs enable conditional RNAi activation using diverse potential cellular RNA signals, enabling new regulatory possibilities including cell-type-specific RNAi and rewiring of transcriptional networks via RNA profile.

To develop ORIENTRs, the inventors first investigated the impact of different cis-regulatory RNA elements on recognition by the Microprocessor. Previous studies[23,26] indicate that the typical Microprocessor substrate RNA consists of an apical loop, a ~22-nt stem with guide RNA and passenger RNA on each side, an imperfect 11-bp basal stem as a molecular ruler to direct Drosha cleavage, and flanking single-stranded RNA at both sides. Aside from these structural requirements, certain conserved sequence motifs are also required for efficient and homogeneous enzyme processing, including the UG motif at the basal junction, UGU/GUG motif in the apical loop, the mismatched GHG (mGHG) motif in basal stem, and CNNC in 3' flanking sequence[25,28] [25] (FIG. 1A). Although cleavage efficiency and homogeneity are correlated with the number of these cis elements in the substrate, it is believed that a pri-miRNA with a stable basal stem plus only one sequence motif is adequate to define a Microprocessor substrate[29]. Based on the above molecular features, the inventors identified the basal stem of the pri-miRNA, which adopts a conserved structure with relatively flexible sequence requirements, as an ideal target to regulate substrate accessibility through structural manipulations.

Pri-miRNA 16-2 was chosen as the Microprocessor substrate scaffold to study experimentally as it possesses signature pri-miRNA structures and has a clear preference in processing into a single miRNA from the 5' arm of the hairpin (5p-miRNA) to reduce potential off-target effects[18]. By swapping the original miR16-2 sequence with a viral miRNA sequence (miR-HSUR4)[30], the pri-miRNA was repurposed to silence a green fluorescent protein (GFP) reporter harboring a miR-HSUR4 target site to directly monitor RNAi activity (FIG. 4A). To investigate the design flexibility of an effective pri-miRNA scaffold, the inventors first modified the upstream sequence flanking the scaffold basal stem by modifying its sequence, structure, or both its sequence and structure (FIG. 4B). All three altered scaffolds retained their effectiveness in silencing GFP, demonstrating that the upstream sequence of the pri-miRNA basal stem does not possess essential RNA motifs for a functional pri-miRNA scaffold and that upstream hairpin structure does not sterically hinder downstream miRNA biogenesis (see Table 2 for sequences). The sequence/structure flexibility can facilitate integration of cis-regulatory RNA motifs for our later conditional pri-miRNA designs.

TABLE 2

Plasmids for testing pri-miRNA 5' flank region sequence and structure requirements. Sequence information: the following sequences are inserted following a U6 promoter for transcription in cells.

| Plasmid ID | Plasmid Name | cDNA Sequence encoding the miRNA's | SEQ ID NO: |
|---|---|---|---|
| ZY-34 | pri-miR-16_2 | GCGCTAATACGACTCACTATAGGGATAAACATACATGCGCAACTG ACATACTTGTTCCACTCTAGCAGCACGTAAATATTGGCGTAGTGAA ATATATATTAAACACCAATATTACTGTGCTGCTTTAGTGTGACAGG GATACAGCAACTTTTTT | 13 |
| ZY-35 | pri-miR-HSUR4 | GCGCTAATACGACTCACTATAGGGATAAACATACATGCG CAACTGACATACTTGTTCCACTCACCGTGTTGCTACAGCT ATAAGTAGTGAAATATATATTAAACATATAGCTGATGCA ACACGGATAGTGTGACAGGGATACAGCAACTTTTTT | 14 |
| ZY-71 | pri-miR-HSUR4_5'hpin | GGTCAGTTCGCGCTAATACGACTCACTATAGGGATAAACATACAT GCGCGAACTGACATACTTGTTCCACTCACCGTGTTGCTACAGCTAT AAGTAGTGAAATATATATTAAACATATAGCTGATGCAACACGGAT AGTGTGACAGGGATACAGCAACTTTTTT | 15 |
| ZY-72 | pri-miR-HSUR4_5'altseq | GCGCTAATACGACTCACTATAGGGATAAACATACATGCGCCCTCA ACGATACTTGTTCCACTCACCGTGTTGCTACAGCTATAAGTAGTGA AATATATATTAAACATATAGCTGATGCAACACGGATAGTGTGACA GGGATACAGCAACTTTTTT | 16 |
| ZY-73 | pri-miR-HSUR4_5'altseq + hpin | GCGTTGAGGGCGCTAATACGACTCACTATAGGGATAAACATACAT GCGCCCTCAACGATACTTGTTCCACTCACCGTGTTGCTACAGCTAT AAGTAGTGAAATATATATTAAACATATAGCTGATGCAACACGGAT AGTGTGACAGGGATACAGCAACTTTTTT | 17 |

Next, to investigate the structural and sequence constraints for pri-miRNA, the inventors swapped the native pri-miR 16-2 basal stem region (m and m'*, where '* designates imperfect reverse complement) with scrambled sequences (n and n'*) (FIG. 1B, FIG. 4C, see Table 3A for sequences). As expected, when either m or m'* strand was replaced by n or n'* to disrupt the basal stem, the scaffold lost its capacity to produce miRNA and was thus ineffective in silencing GFP (FIG. 1b). However, when both sequences were replaced while preserving the structure, the pri-miRNA scaffold recovered its potency in repressing the GFP. Based on these results, it was determined that the mGHG and UG motifs are dispensable for a functional pri-miRNA in the ORIENTR system, and that the basal stem requires a conserved structure instead of a conserved sequence, providing flexibility in conditional pri-miRNA design.

TABLE 3A

Plasmids for testing pri-miRNA basal stem region sequence and structure requirements

| Plasmid ID | Plasmid Name | Sequence | SEQ ID NO: |
|---|---|---|---|
| ZY-35 | pri-miR-HSUR4 | GCGCTAATACGACTCACTATAGGGATAAACATACATGCGCAAC TGACATACTTGTTCCACTCACCGTGTTGCTACAGCTATAAGTAG TGAAATATATATTAAACATATAGCTGATGCAACACGGATAGTG TGACAGGGATACAGCAACTTTTTT | 13 |
| ZY-129 | basal_stem_n + m* | GCGCTAATACGACTCACTATAGGGATAAACATACATGCGCAAC TGACATAAGCCATAACTCCACCGTGTTGCTACAGCTATAAGTAG TGAAATATATATTAAACATATAGCTGATGCAACACGGATAGTG TGACAGGGATACAGCAACTTTTTT | 18 |
| ZY-130 | basal_stem_m + n* | GCGCTAATACGACTCACTATAGGGATAAACATACATGCGCAAC TGACATACTTGTTCCACTCACCGTGTTGCTACAGCTATAAGTAG TGAAATATATATTAAACATATAGCTGATGCAACACGGATGAGT CATGGCTGATACAGCAACTTTTTT | 19 |
| ZY-131 | basal_stem_n + n* | GCGCTAATACGACTCACTATAGGGATAAACATACATGCGCAAC TGACATAAGCCATAACTCCACCGTGTTGCTACAGCTATAAGTAG TGAAATATATATTAAACATATAGCTGATGCAACACGGATGAGT CATGGCTGATACAGCAACTTTTTT | 20 |

TABLE 3B

RNA sequences of exemplary pri-miRNA and miRNAs shown in FIG. 4A-4C and assessed in the Examples:

| Plasmid Name | miRNA sequence (RNA) | |
|---|---|---|
| miR-HSUR4 | 5'-ACUUGUUCCACUCACCGUGUUGCUACAGCUAUAAGUAGUGAAAUAUAUAUU AAA*CAUAUAGCUGAUGCAACACGGAU*AGUGUGACAGGGAUACAGC-3' | SEQ ID NO: 89 (FIG. 4A) |
| miR-16-2 | 5'-ACUUGUUCCACUCUAGCAGCACGUAAAUAUUGGCGUAGUGAAAUAUAUAUU AAA*CACCAAUAUUACUGUGCUGCUUU*AGUGUGACAGGGAUACAGC-3' | SEQ ID NO: 88 (FIG. 4A and FIG. 4C) |
| pri-miR-16_2 | 5'-AUAAACAUACAUGCGCAACUGACAUACUUGUUCCACUCUAGCAGCACGUAAA UAUUGGCGUAGUGAAAUAUAUAUUAAA*CACCAAUAUUACUGUGCUGCUUU*A GUGUGACAGGGAUACAGCAAC-3' | SEQ ID NO: 94 |
| pri-miR-HSUR4 | 5'-AUAAACAUACAUGCGCAACUGACAUACUUGUUCCACUCACCGUGUUGCUACA GCUAUAAGUAGUGAAAUAUAUAUUAAA*CAUAUAGCUGAUGCAACACGGAUA* GUGUGACAGGGAUACAGC-3' | 90 (FIG. 4B) |
| pri-miR-HSUR4_5'hpin | 5' GGUCAGUUCGCGCUAAUACGACUCACUAUAGGGAUAAACAUACAUGCGCAA CUGACAUACUUGUUCCACUCACCGUGUUGCUACAGCUAUAAGUAGUGAAAU AUAUAUUAAA*CAUAUAGCUGAUGCAACACGGAU*AGUGUGACAGGGAUACAG C-3' | 91 (FIG. 4B) |
| pri-miR-HSUR4_5'altseq | 5'-GCGCUAAUACGACUCACUAUAGGGAUAAACAUACAUGCGCCCUCAACGAUAC UUGUUCCACUCACCGUGUUGCUACAGCUAUAAGUAGUGAAAUAUAUAUUAA A*CAUAUAGCUGAUGCAACACGGAU*AGUGUGACAGGGAUACAGC-3' | 92 (FIG. 4B) |
| pri-miR-HSUR4_5'altseq + hpin | 5'-GCGUUGAGGGCGCUAAUACGACUCACUAUAGGGAUAAACAUACAUGCGCCCU CAACGAUACUUGUUCCACUCACCGUGUUGCUACAGCUAUAAGUAGUGAAAU AUAUAUUAAA*CAUAUAGCUGAUGCAACACGGAU*AGUGUGACAGGGAUACAG C-3' | 93 (FIG. 4B) |
| pri-miR-HSUR4 | 5'-AUAAACAUACAUGCGCAACUGACAUACUUGUUCCACUCACCGUGUUGCUACA GCUAUAAGUAGUGAAAUAUAUAUUAAA*CAUAUAGCUGAUGCAACACGGAUA* GUGUGACAGGGAUACAGC-3' | 90 (FIG. 4B) |
| basal_stem_n + m* | 5'-AAGCCAUAACUCCACCGUGUUGCUACAGCUAUAAGUAGUGAAAUAUAUAUU AAA*CAUAUAGCUGAUGAUGCAACACGGAU*AGUGUGACAGGGAUACAGC-3' | 95 (FIG. 4C) |
| basal_stem_m + n* | 5'-ACUUGUUCCACUCACCGUGUUGCUACAGCUAUAAGUAGUGAAAUAUAUAUU AAA*CAUAUAGCUGAUGCAACACGGAU*GAGUCAUGGCUGAUACAGC-3' | 96 (FIG. 4C) |
| basal_stem_n + n* | 5'-AAGCCAUAACUCCACCGUGUUGCUACAGCUAUAAGUAGUGAAAUAUAUAUU AAA*CAUAUAGCUGAUGCAACACGGAU*GAGUCAUGGCUGAUACAGC-3' | 97 (FIG. 4C) |

((underlined = 5' basal stem, double underlined = 3' basal stem, bold = guide strand, italics = passenger strand, grey highlight- apical loop, thick underline = 5' scaffold flanking sequence of a pri-miRNA scaffold)

Example 2

ORIENTR Design and Performance

Based on the above results, the inventors devised a design for ORIENTRs that built upon earlier work on aptamer-based RNA switches used for in vitro diagnostics[16,51]. In the present ORIENTR design, the 11-nt sequence in 5' half of the basal stem was sequestered in a hairpin structure to preclude the correct pri-miRNA substrate structure from folding (FIG. 1C and FIG. 5A). Disruption of basal stem folding prevents Drosha acquisition and processing of the substrate pri-miRNA. This upstream hairpin can be opened by interacting with a 37-nt cognate RNA trigger as input through toehold-mediated strand displacement[17] in the sensing domain (FIG. 1C, left). This transition releases the sequestered 11-nt sequence and reconstitutes the basal stem in the reconfiguration domain to activate Drosha recognition, and therefore initiates miRNA biogenesis to generate a mature functional miRNA as the output (FIG. 1C, right). The binding signal recorded by the sensing domain is transmitted to the output domain via structural refolding of the reconfiguration domain, rather than the miRNA-encoding region, successfully decoupling the input sequence from the output sequence.

Figure 6:
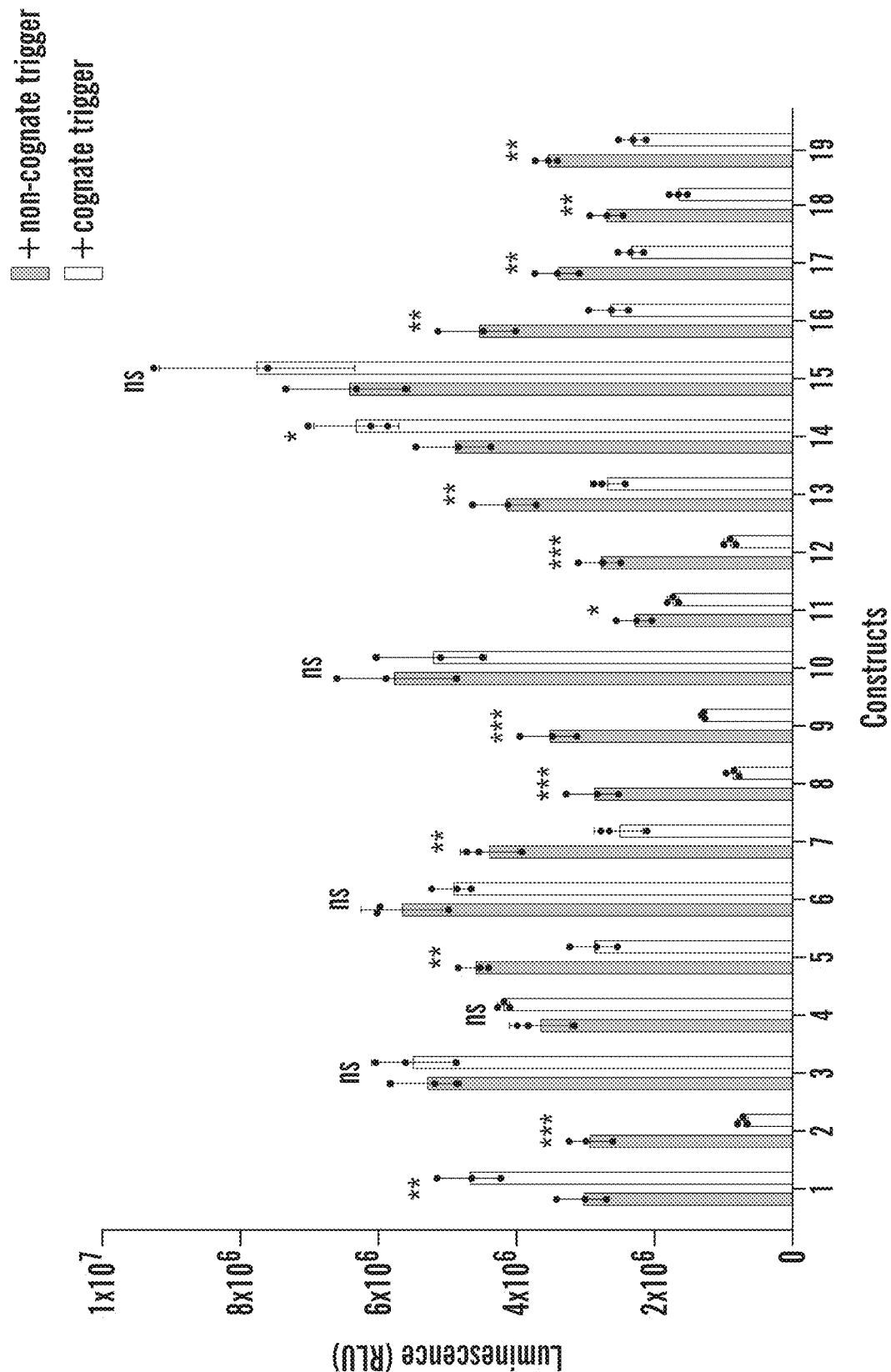
FIG. 6 shows luciferase reporter signal for 19 different ORIENTR devices with non-cognate or cognate triggers. Arrows indicate the constructs with lower luminescence signal in response to the cognate trigger. (ns) P>0.05, (*) P<0.05, () P<0.01, (*) P<0.001, t test, n=3 biological replicates, bars represent the mean±s.d.

With de novo computational RNA design by NUPACK[32] (FIG. 5), 19 different ORIENTR molecules (also referred to herein as ORIENTR devices) were generated with corresponding cognate trigger RNAs (see Table 4 for sequences) and constructed them in separate plasmids with transcription initiated by the human U6 promoter. To inhibit RNA degradation, a small protecting hairpin was included at the 5' end of the trigger RNA[33]. ORIENTR and trigger RNA plasmids, together with a reporter GFP plasmid, were co-transfected into HEK293T cells. For many of the ORIENTRs, cells displayed lower GFP fluorescence in the presence of the cognate trigger compared to the non-cognate trigger (FIG. 1D), and similar results were achieved from a luciferase reporter (FIG. 6), indicating a cognate trigger RNA induced RNAi activity.

TABLE 4

Sequences for exemplary ORIENTR molecules and corresponding their RNA-trigger sequences

| Plasmid ID | Plasmid Name | Sequence | SEQ ID NO: |
|---|---|---|---|
| ZY-132 | ORIENTR_1 | GGGTGAAATGAAATGAAAGCAGAGTGACAATAGAGGTAAGACGCAGT ATCTGTATCCCGACAGATACTGCAACTTACCTCCATTGTCACTCTGCACC GTGTTGCTACAGCTATAAGTAGTGAAATATATATTAAACATATAGCTGA TGCAACACGGAACAGAATGACAAGATACAGCAACTTTTTT | 21 |
| ZY-133 | ORIENTR_2 | GGGTGAGATGGATGTGATTGATAGGTAAGATTGTATTGCTCCTCGCCG ACGCCTCCATCTGCGTCGGCGACAAGCAATACTATCTTACCTATCAACC GTGTTGCTACAGCTATAAGTAGTGAAATATATATTAAACATATAGCTGA TGCAACACGGAGGATAAGTAAGAGATACAGCAACTTTTTT | 22 |
| ZY-134 | ORIENTR_3 | GGGTGATGGAGTAGAGAATGTATTAGGAGTTAGAATTAGACTACGAG GCTGCTGCTCGTCGCAGCCTCGTTTTCTAATTCTAACTCCTAATACAACC GTGTTGCTACAGCTATAAGTAGTGAAATATATATTAAACATATAGCTGA TGCAACACGGAAGTATGAGGAGTGATACAGCAACTTTTTT | 23 |
| ZY-135 | ORIENTR_4 | GGGTGAATAAGAATGAAAGTATGGAAGATGTAGTCGTGTAACGGATA TGCAACTGCGGCTTTGCATATCCTATACACGACAACATCTTCCATACAC CGTGTTGCTACAGCTATAAGTAGTGAAATATATATTAAACATATAGCTG ATGCAACACGGAATATGCAAGATGGATACAGCAACTTTTTT | 24 |
| ZY-151 | ORIENTR_5 | GGGTCGAATGTTAGTGTGCGCTGTTGAGGTATGTAGTTGATATTCCGG GCAGAAACATGACTGCCCGGAACCTCAACTACCTACCTCAACAGCGAC CGTGTTGCTACAGCTATAAGTAGTGAAATATATATTAAACATATAGCTG ATGCAACACGGAAGCTGGTGAGGTGATACAGCAACTTTTTT | 25 |
| ZY-152 | ORIENTR_6 | GGGTGATGAGAGTAAATGGACGAAATGTAGTAAGTAATGATATCTTCC ATCCAAATCAAAGGATGGAAGACTTCATTACTAACTACATTTCGTCACC GTGTTGCTACAGCTATAAGTAGTGAAATATATATTAAACATATAGCTGA TGCAACACGGACACGACATGTAGGATACAGCAACTTTTTT | 26 |
| ZY-153 | ORIENTR_7 | GGGTCGAATGGTAGTAAGTTAAGGATAATGTAATGTGTCTCACGAGGC TCTGTGGCTTACCAGAGCCTCGATAGACACATAACATTATCCTTAAACC GTGTTGCTACAGCTATAAGTAGTGAAATATATATTAAACATATAGCTGA TGCAACACGGAATAAGAATAATGGATACAGCAACTTTTTT | 27 |
| ZY-154 | ORIENTR_8 | GGGTGAATGGCGTAAGTAGATGGTAGGATGACAGTTGAGTTCGCAGT GGAAACCTACTATTTTCCACTGCACACTCAACTCTCATCCTACCATCACC GTGTTGCTACAGCTATAAGTAGTGAAATATATATTAAACATATAGCTGA TGCAACACGGAGATGGCAGGATGGATACAGCAACTTTTTT | 28 |
| ZY-155 | ORIENTR_9 | GGGTCGTTAGTTATTAGAGGTATGCTTAAGTTCGTATAGTCCTCGGTCT CGACCGGATCATCGAGACCGATTACTATACGCACTTAAGCATACCACC GTGTTGCTACAGCTATAAGTAGTGAAATATATATTAAACATATAGCTGA TGCAACACGGAAGTATACTTAAGGATACAGCAACTTTTTT | 29 |
| ZY-156 | ORIENTR_10 | GGGTGAGAGCATAGAGACGTGAAGATGGGATAGGAAGTGACATGGC GTCTCTACGTTGTAAGAGACGCCACTTCACTTCCCATCCCATCTTCACAC | 30 |

TABLE 4-continued

Sequences for exemplary ORIENTR molecules and corresponding their RNA-trigger sequences

| Plasmid ID | Plasmid Name | Sequence | SEQ ID NO: |
|---|---|---|---|
| | | CGTGTTGCTACAGCTATAAGTAGTGAAATATATATTAAACATATAGCTG ATGCAACACGGAATGAACATGGGAGATACAGCAACTTTTTT | |
| ZY-157 | ORIENTR_11 | GGGTGATTAGTTGAAAGATATAGAAAGCGAAGTCGGTAAATCCGCGG TAAGCTGGTGAGGGCTTACCGCGTCTTTACCGAATTCGCTTTCTATAAC CGTGTTGCTACAGCTATAAGTAGTGAAATATATATTAAACATATAGCTG ATGCAACACGGACATAGCAAGCGAGATACAGCAACTTTTTT | 31 |
| ZY-158 | ORIENTR_12 | GGGTGCCCTGTCGTTCTAGTATGTAGCTTGTCGTGTTAGTGACTCTACC ACTGGCTGGGTAGTGGTAGAGCGACTAACACTACAAGCTACATACACC GTGTTGCTACAGCTATAAGTAGTGAAATATATATTAAACATATAGCTGA TGCAACACGGATTATGAAGCTTGGATACAGCAACTTTTTT | 32 |
| ZY-159 | ORIENTR_13 | GGGTCATTATGTTATTTCGCTAATCAGGCACGGTGTAGTTCCGCATAGC CCAACTTTCCGTGGGCTATGCATAACTACACAGTGCCTGATTAGCACCG TGTTGCTACAGCTATAAGTAGTGAAATATATATTAAACATATAGCTGAT GCAACACGGATCTAAGCAGGCAGATACAGCAACTTTTTT | 33 |
| ZY-160 | ORIENTR_14 | GGGTGAGGGCAAATTGAGGCGCGTTTAGGCTGGTTAGATTATTGGCT GGAAATCAGCACATTTCCAGCCACGAATCTAACGAGCCTAAACGCGCA CCGTGTTGCTACAGCTATAAGTAGTGAAATATATATTAAACATATAGCT GATGCAACACGGAACGCGGTTAGGCGATACAGCAACTTTTTT | 34 |
| ZY-162 | ORIENTR_15 | GGGTGATAATAGAATAATGGAGTAAACGAATGCGCTAGAACCCGGTT ACTCATCTGAATGTGAGTAACCGACTTCTAGCGAATTCGTTTACTCCAC CGTGTTGCTACAGCTATAAGTAGTGAAATATATATTAAACATATAGCTG ATGCAACACGGACGAGTTAACGAAGATACAGCAACTTTTTT | 35 |
| ZY-163 | ORIENTR_16 | GGGTGCCTTTAGCTTGCAATGTCGTTTCTGTTCGTGTTAGAACGTGAAG CTTGCAGAACAAAGCTTCACGGCCTAACACGCACAGAAACGACATACC GTGTTGCTACAGCTATAAGTAGTGAAATATATATTAAACATATAGCTGA TGCAACACGGACTGTCATTTCTGGATACAGCAACTTTTTT | 36 |
| ZY-164 | ORIENTR_17 | GGGTGATTAGATGACATACCCTTAACGAACCGGGATTTAGTCGGATGG CTCGACCGGATCCGAGCCATCCATCTAAATCCAGGTTCGTTAAGGGAC CGTGTTGCTACAGCTATAAGTAGTGAAATATATATTAAACATATAGCTG ATGCAACACGGAACCTTTACGAACGATACAGCAACTTTTTT | 37 |
| ZY-165 | ORIENTR_18 | GGGTCTCTACGCCGCTTCGAATGTTTATGTTATCGCTTGTAACCAGCGC TCCGTTTAAGTGGAGCGCTGGACACAAGCGACAACATAAACATTCACC GTGTTGCTACAGCTATAAGTAGTGAAATATATATTAAACATATAGCTGA TGCAACACGGACAATGATTATGTGATACAGCAACTTTTTT | 38 |
| ZY-166 | ORIENTR_19 | GGGTCATATAGGTTAGGCAGCAGGTATCACAGTGTATCTCTGAGATGT ATAGCCATAGCACTATACATCTATGAGATACAATGTGATACCTGCTACC GTGTTGCTACAGCTATAAGTAGTGAAATATATATTAAACATATAGCTGA TGCAACACGGATGCAGCTATCACGATACAGCAACTTTTTT | 39 |
| ZY-140 | trigger1 | GGGCCCATAGGATTTTACCTATGGGAAACTTACCTCTATTGTCACTCTG CTTTCATTTCATTTCATTTTTT | 40 |
| ZY-141 | trigger2 (trigger_A) | GGGCTCGATAGCGCAGACTATCGAGACAAGCAATACAATCTTACCTAT CAATCACATCCATCTCATTTTTT | 41 |
| ZY-142 | trigger3 | GGGCACGTTCCTTAGTTGGAACGTGATTTCTAATTCTAACTCCTAATAC ATTCTCTACTCCATCATTTTTT | 42 |
| ZY-143 | trigger4 | GGGCCTAAGTTGAGAATAACTTAGGAATTACACGACTACATCTTCCATA CTTTCATTCTTATTCATTTTTT | 43 |
| ZY-167 | trigger5 | GGGAGGTCGTGCAATAACACGACCTACTTCAACTACATACCTCAACAG CGCACACTAACATTCGATTTTTT | 44 |
| ZY-168 | trigger6 (trigger_F) | GGGCTCAGCCAGCACTGTGGCTGAGCGTTCATTACTTACTACATTTCGT CCATTTACTCTCATCATTTTTT | 45 |
| ZY-169 | trigger7 (trigger_D) | GGGCGCAGTTATTTGCTTAACTGCGGACAGACACATTACATTATCCTTA ACTTACTACCATTCGATTTTTT | 46 |
| ZY-170 | trigger8 | GGGAGCCATGACCCTTATCATGGCTCTTACTCAACTGTCATCCTACCAT CTACTTACGCCATTCATTTTTT | 47 |

TABLE 4-continued

Sequences for exemplary ORIENTR molecules and corresponding their RNA-trigger sequences

| Plasmid ID | Plasmid Name | Sequence | SEQ ID NO: |
|---|---|---|---|
| ZY-171 | trigger9 (trigger_C) | GGGCCATAGATATTTCAATCTATGGAATACTATACGAACTTAAGCATACCTCTAATAACTAACGATTTTTT | 48 |
| ZY-172 | trigger10 | GGGCCTTTGGCATCCCTGCCAAAGGCATTCACTTCCTATCCCATCTTCACGTCTCTATGCTCTCATTTTTT | 49 |
| ZY-173 | trigger11 (trigger_E) | GGGCCAACTCATAACTATGAGTTGGAACTTTACCGACTTCGCTTTCTATATCTTTCAACTAATCATTTTTT | 50 |
| ZY-174 | trigger12 | GGGACGGCACTGGGACAAGTGCCGTATAACTAACACGACAAGCTACATACTAGAACGACAGGGCATTTTTT | 51 |
| ZY-175 | trigger13 (trigger_B) | GGGAGCCGACGACCGACCGTCGGCTAAGAACTACACCGTGCCTGATTAGCGAAATAACATAATGATTTTTT | 52 |
| ZY-176 | trigger14 | GGGACGTCTGCTACGCTGCAGACGTCTGAATCTAACCAGCCTAAACGCGCCTCAATTTGCCCTCATTTTTT | 53 |
| ZY-178 | trigger15 | GGGCACCAGAGCTGCGCCTCTGGTGATTTTCTAGCGCATTCGTTTACTCCATTATTCTATTATCATTTTTT | 54 |
| ZY-179 | trigger16 | GGGACCTGCGAACGAGGTCGCAGGTAAACTAACACGAACAGAAACGACATTGCAAGCTAAAGGCATTTTTT | 55 |
| ZY-180 | trigger17 | GGGTGCCGGTCTTATGCGACCGGCACATCTAAATCCCGGTTCGTTAAGGGTATGTCATCTAATCATTTTTT | 56 |
| ZY-181 | trigger18 | GGGTGCCCTCGCGGAGTCGAGGGCATGAACAAGCGATAACATAAACATTCGAAGCGGCGTAGAGATTTTTT | 57 |
| ZY-182 | trigger19 | GGGCCCTTACCTGTTTAGGTAAGGGACTGAGATACACTGTGATACCTGCTGCCTAACCTATATGATTTTTT | 58 |
| ZY-18 | noncognate trigger | GGGCCGTACTAAGGTGCTAGTACGGCATACTAACTCTACCTTACCTTCACTTCACTTCATTTTT | 59 |

Example 3

Optimizing ORIENTR Structure

Figure 1D:
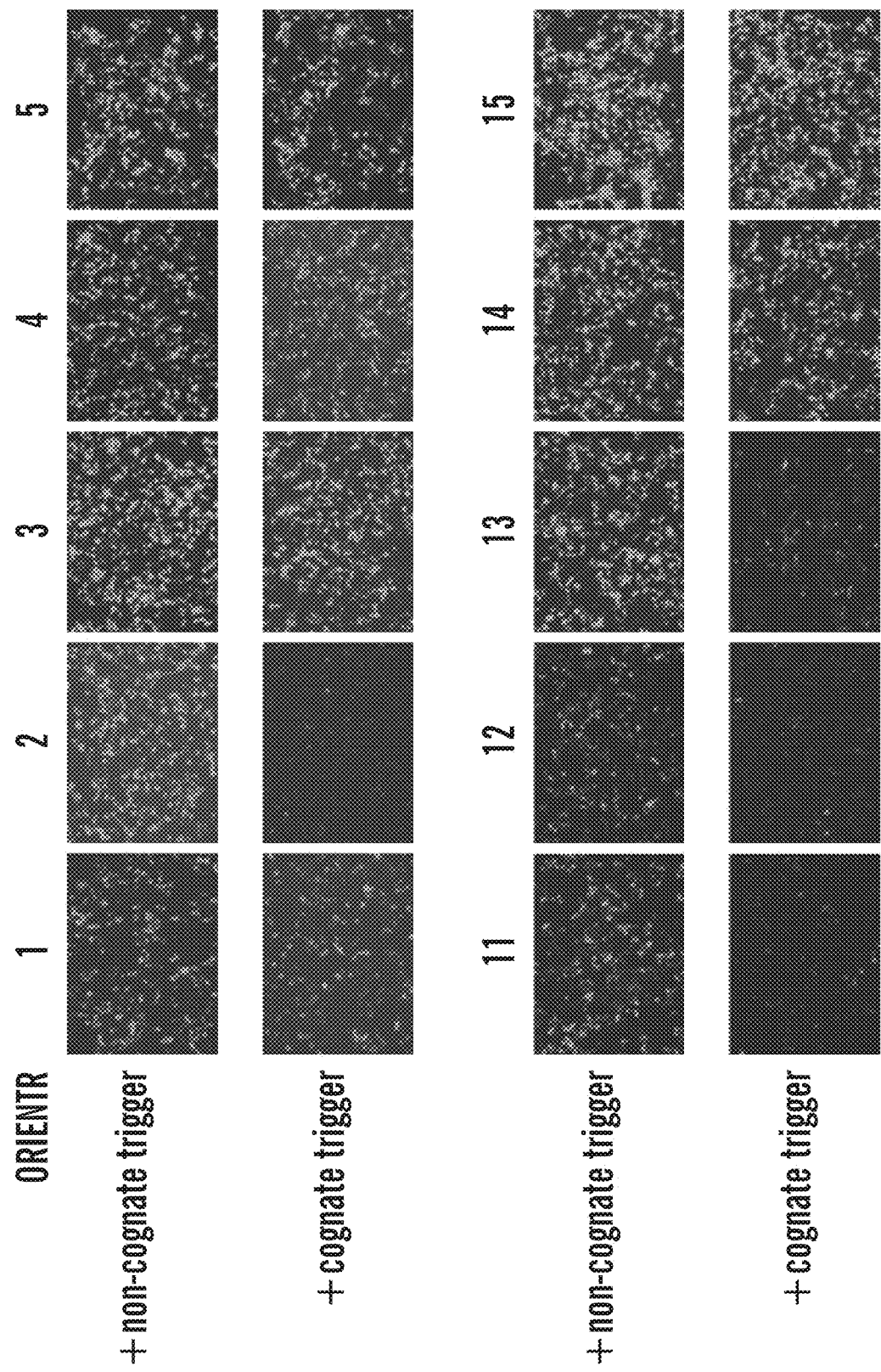
Figure 1D:
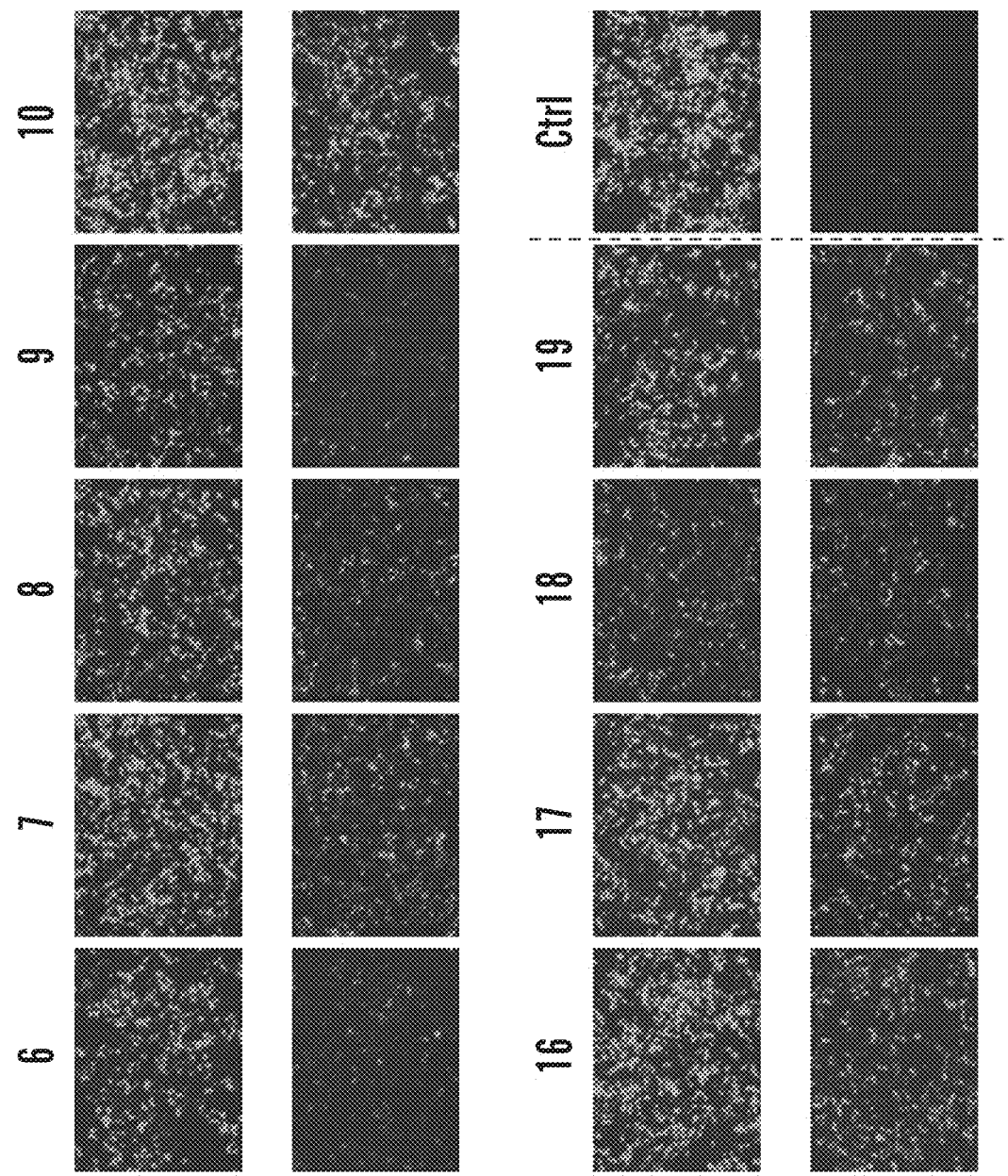

Although the 19 exemplary ORIENTR molecules and design strategy were demonstrated to be effective in generating RNAi in response to specific cellular RNAs, the inventors optimized the ORIENTR molecule design to address two major challenges: firstly, some ORIENTR molecules had reduced folding and formation of the reconfiguration domain that led some devices to display leaky miRNA production resulting in repressed target gene expression in the absence of cognate trigger RNA (e.g. ORIENTR_12 in FIG. 1D); and secondly, the dynamic range of regulation is limited, suggesting only partial activation of ORIENTRs by the RNA triggers (e.g. ORIENTR_7 in FIG. 1D).

To investigate the effect of ORIENTR structure on performance, the inventors optimized and modulated the secondary structure of the sequestration arm by varying the stem length and bulge size as well as the flexibility of 3' basal stem for ORIENTR_2 (FIG. 2a, Table 5). The results demonstrated that the conformation of the sequestration arm and the downstream flanking sequence affects signal leakage and the sensitivity of the response to the RNA trigger (FIG. 2B). Thus, it is possible to tune ORIENTR design parameters to achieve minimum background activation or maximum output response to suit specific requirements in certain applications.

TABLE 5

Design optimization for ORIENTR_2

| Plasmid ID | Plasmide Name | Sequence | SEQ ID NO |
|---|---|---|---|
| ZY-148 | ORIENTR 2_1 | GGGTGAGATGGATGTGATTGATAGGTAAGATTGTATTGCTCCTACAAGCAATACTATCTTACCTATCAACCGTGTTGCTACAGCTATAAGTAGTGAAATATATATTAAACATATAGCTGATGCAACACGGAGGATAAGTAAGAGATACAGCAACTTTTTTT | 60 |
| ZY-149 | ORIENTR 2_2 | GGGTGAGATGGATGTGATTGATAGGTAAGATTGTATTGCTCTGATTTCACTCAGAGCAATACTATCTTACCTATCAACCGTGTTGCTACAGCTATAAGTAGTGAAATATATATTAAACATATAGCTGATGCAACACGGAGGATAAGTAAGAGATACAGCAACTTTTTT | 61 |

TABLE 5-continued

Design optimization for ORIENTR_2

| Plasmid ID | Plasmide Name | Sequence | SEQ ID NO |
|---|---|---|---|
| ZY-150 | ORIENTR 2_3 | GGGTGAGATGGATGTGATTGATAGGTAAGATTGTATTGCTCTGAT TTCACTAAAATCAGAGCAACCCAATCTTACCTATCAACCGTGTTGC TACAGCTATAAGTAGTGAAATATATATTAAACATATAGCTGATGCA ACACGGAGGATAAGTAAGAGATACAGCAACTTTTTT | 62 |
| ZY-206 | ORIENTR 2_4 | GGGTGAGATGGATGTGATTGATAGGTAAGATTGTATTGCTCCTAC AAGCAATACTATCTTACCTATCAACCGTGTTGCTACAGCTATAAGT AGTGAAATATATATTAAACATATAGCTGATGCAACACGGAGGATA AGTAAGAGATACAGCAACCTTATCATTTTTTT | 63 |

Figure 2E:
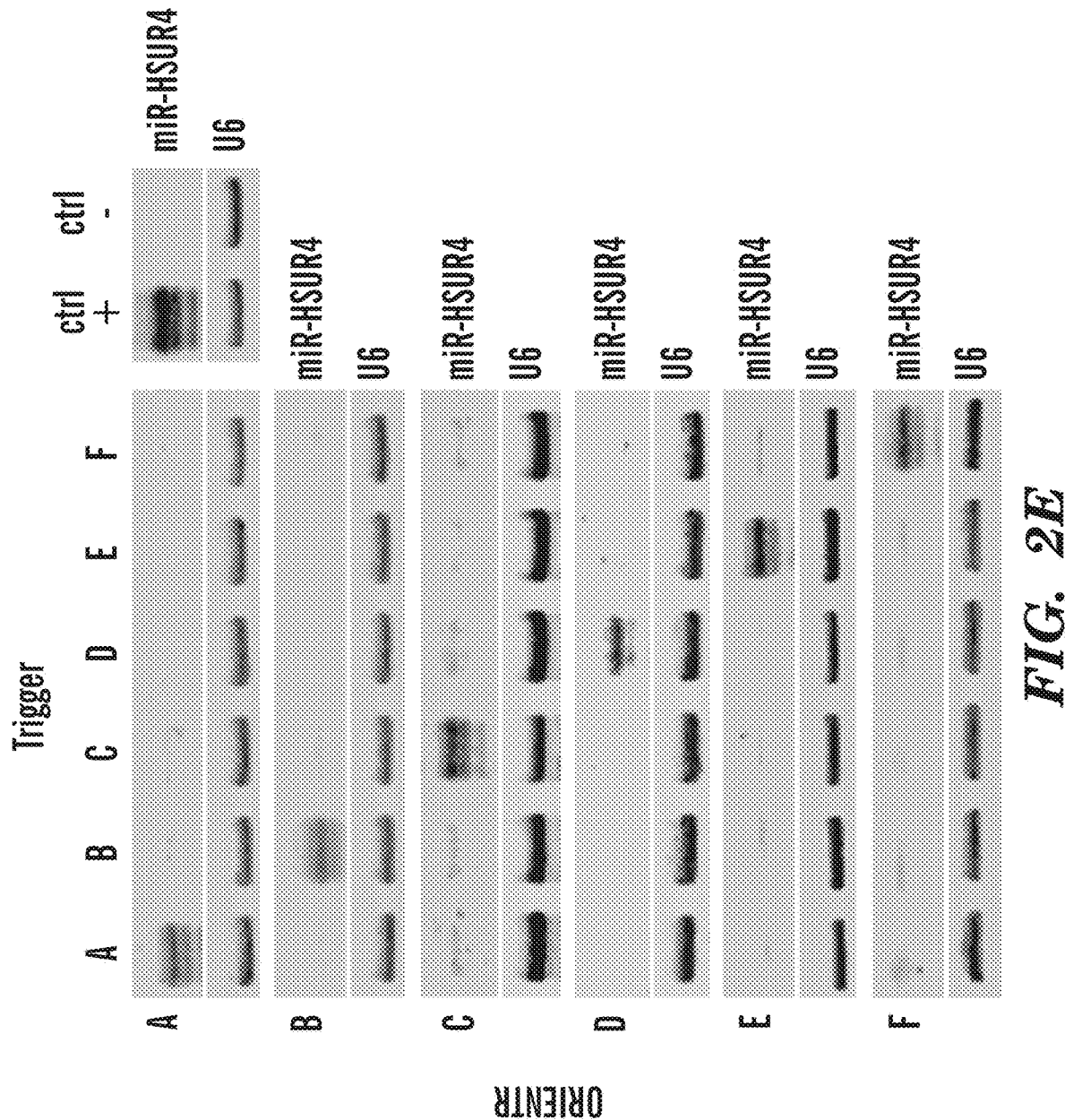
Figure 7:
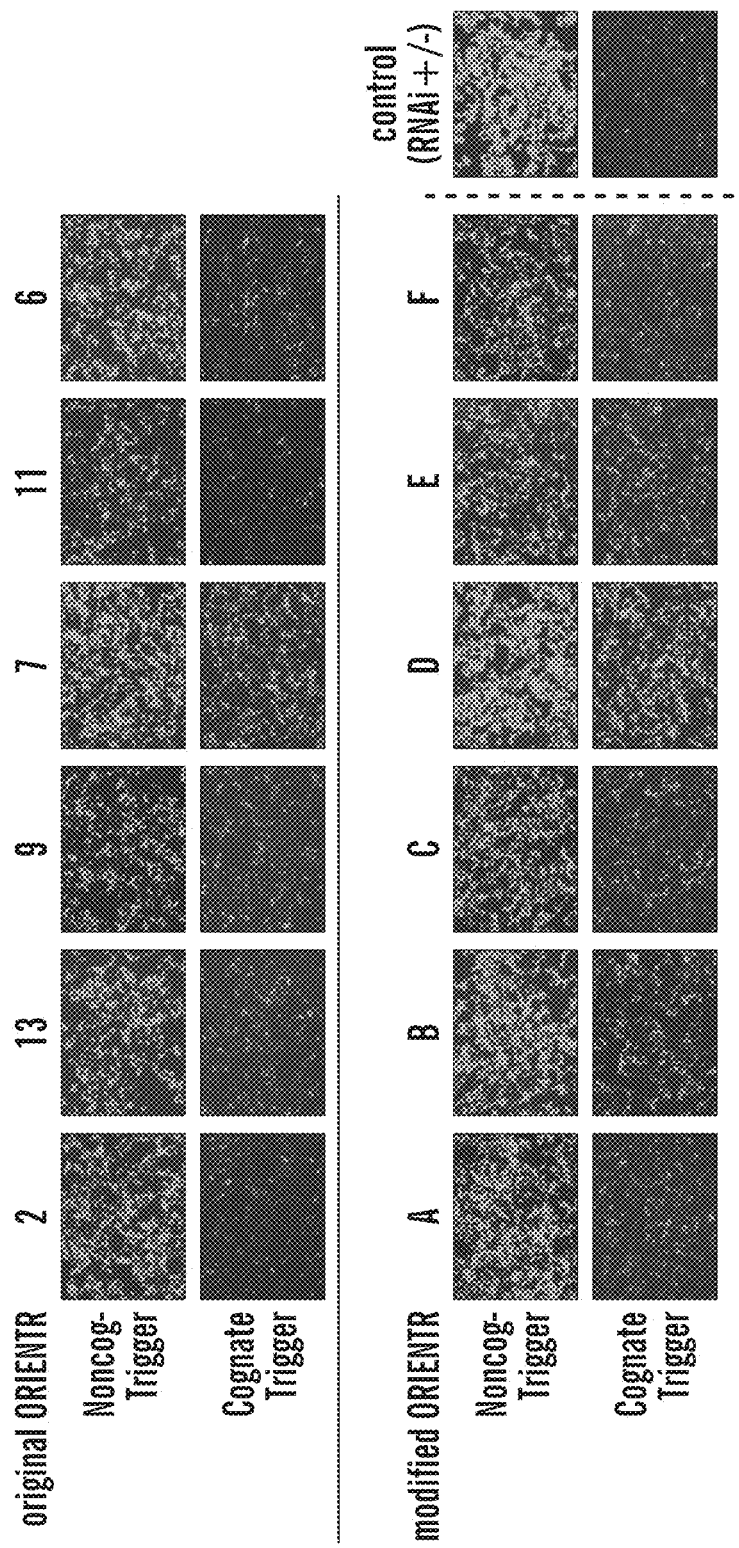
FIG. 7 shows results of six exemplary ORIENTRs before and after modification with the leak-reduction motif in response to non-cognate/cognate triggers with a GFP reporter. ORIENTRs 2, 13, 9, 7, 11 and 6 were modified to have a 3' leak-reduction motif, and were referred to as A, B, C, D, E, F, respectively. RNAi positive control is from pri-miR-HSUR4; RNAi negative control is from pri-miR-16-2.

It was demonstrated that in ORIENTR_2_4, the 6-nt domain that weakly base-paired with the 3' basal stem decreased leaky expression while preserving responsiveness against its trigger (FIG. 2B). The inventors included this leak-reduction motif for another five representative ORIENTR switches (ORIENTR 13, 9, 7, 11, 6, FIG. 1D), and together named them ORIENTRs A through E (FIG. 2c, Table 6). In general, these ORIENTRs with the leak-reduction showed slightly increased reporter signal in the presence of the non-cognate trigger (FIG. 2D, compare dark grey to light grey bars), and thus provided less leaky regulation of miRNA production (FIG. 2d, FIG. 7). The inventors tested the orthogonality of the six ORIENTR devices and their triggers by co-transfecting each ORIENTR with all six triggers individually and used Northern blots to quantify the miRNA production from whole-cell extract (FIG. 2E). Although some ORIENTR devices still showed leaky miRNA generation, all six devices demonstrated high orthogonality with increased miRNA production observed only in the presence of the cognate triggers.

TABLE 6

Representative ORIENTRs with leak-reduction motif

| Plasmid ID | Plasmid Name | Sequence | SEQ ID NO: |
|---|---|---|---|
| ZY-206 | ORIENTR_A (modified ORIENTR_2) | GGGTGAGATGGATGTGATTGATAGGTAAGATTGTATTG CTCCTACAAGCAATACTATCTTACCTATCAACCGTGTTGC TACAGCTATAAGTAGTGAAATATATATTAAACATATAGC TGATGCAACACGGAGGATAAGTAAGAGATACAGCAACC TTATCATTTTTT | 64 |
| ZY-212 | ORIENTR_B (modified ORIENTR_13) | GGGTCATTATGTTATTTCGCTAATCAGGCACGGTGTAGT TCCGCATAGCCCAACTTTCCGTGGGCTATGCATAACTAC ACAGTGCCTGATTAGCACCGTGTTGCTACAGCTATAAGT AGTGAAATATATATTAAACATATAGCTGATGCAACACGG ATCTAAGCAGGCAGATACAGCAACGCTTAGTTTTTTT | 65 |
| ZY-202 | ORIENTR_C (modified ORIENTR_9) | GGGTCGTTAGTTATTAGAGGTATGCTTAAGTTCGTATAG TCCTCGGTCTCGACCGGATCATCGAGACCGATTACTATA CGCACTTAAGCATACCACCGTGTTGCTACAGCTATAAGT AGTGAAATATATATTAAACATATAGCTGATGCAACACGG AAGTATACTTAAGGATACAGCAACGTATACTATTTTTTT | 66 |
| ZY-208 | ORIENTR_D (modified ORIENTR_7) | GGGTCGAATGGTAGTAAGTTAAGGATAATGTAATGTGT CTCACGAGGCTCTGTGGCTTACCAGAGCCTCGATAGACA CATAACATTATCCTTAAACCGTGTTGCTACAGCTATAAGT AGTGAAATATATATTAAACATATAGCTGATGCAACACGG AATAAGAATAATGGATACAGCAACTTCTTAATTTTTTT | 67 |
| ZY-210 | ORIENTR_E (modified ORIENTR_11) | GGGTGATTAGTTGAAAGATATAGAAAGCGAAGTCGGTA AATCCGCGGTAAGCTGGTGAGGGCTTACCGCGTCTTTAC CGAATTCGCTTTCTATAACCGTGTTGCTACAGCTATAAGT AGTGAAATATATATTAAACATATAGCTGATGCAACACGG ACATAGCAAGCGAGATACAGCAACTGCTATATTTTTTT | 68 |
| ZY-207 | ORIENTR_F (modified ORIENTR_6) | GGGTGATGAGAGTAAATGGACGAAATGTAGTAAGTAAT GATATCTTCCATCCAAATCAAAGGATGGAAGACTTCATT ACTAACTACATTTCGTCACCGTGTTGCTACAGCTATAAGT AGTGAAATATATATTAAACATATAGCTGATGCAACACGG ACACGACATGTAGGATACAGCAACTGTCGTATTTTTTT | 69 |

TABLE 7

Additional sequence information for miRNA target sequence and Northern probes

| Description | Sequence | SEQ ID NO: |
|---|---|---|
| miR-HSUR4 target site | TTATAGCTGTAGCAACACGGT | 70 |
| miR-HSUR4 sequence | ACCGUGUUGCUACAGCUAUAA | 71 |
| miR-HSUR4 northern probe sequence | TTATAGCTGTAGCAACACGGT/3AzideN/ | 72 |
| U6 northern probe sequence | GCAGGGGCCATGCTAATCTTCTCTGTATCG/3AzideN/ | 73 |
| noncognate trigger northern probe sequence | GTGAAGTGAAGGTAAGGTAGAG/3AzideN/ | 74 |
| miR-7 northern probe sequence | AACAACAAAATCACTAGTCTTCCA/3AzideN/ | 75 |

Example 4

Improving ORIENTR Regulation Dynamics with dCas13d

Figure 8:
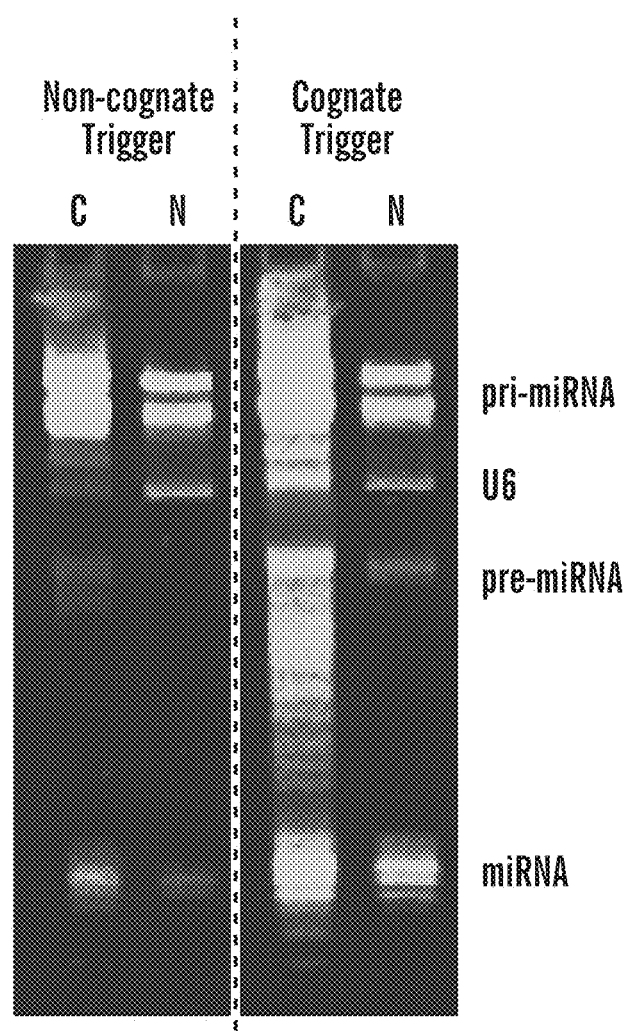
FIG. 8 shows results of a northern blot for ORIENTR_2 in response to non-cognate and cognate trigger RNAs. C denotes the cytoplasm; N denotes the nucleus. The HSUR4 probe was used to image pri-miRNA, pre-miRNA, and miRNA localization. U6 RNA blotting was used as the control.

Next, the inventors optimized the ORIENTR molecule to increase the regulation dynamics by enhancing the ORIENTR interaction with the trigger RNA. Since Microprocessor regulation occurs in the nucleus, the inventors first investigated the localization of ORIENTR and trigger RNA. It was discovered that the majority of ORIENTR (FIG. 8) and trigger RNAs (FIG. 3A) were exported to the cytoplasm. The inventors assessed if the trigger RNA interaction with ORIENTR was limited by RNA abundance and stability in the nucleus.

Figure 3D:
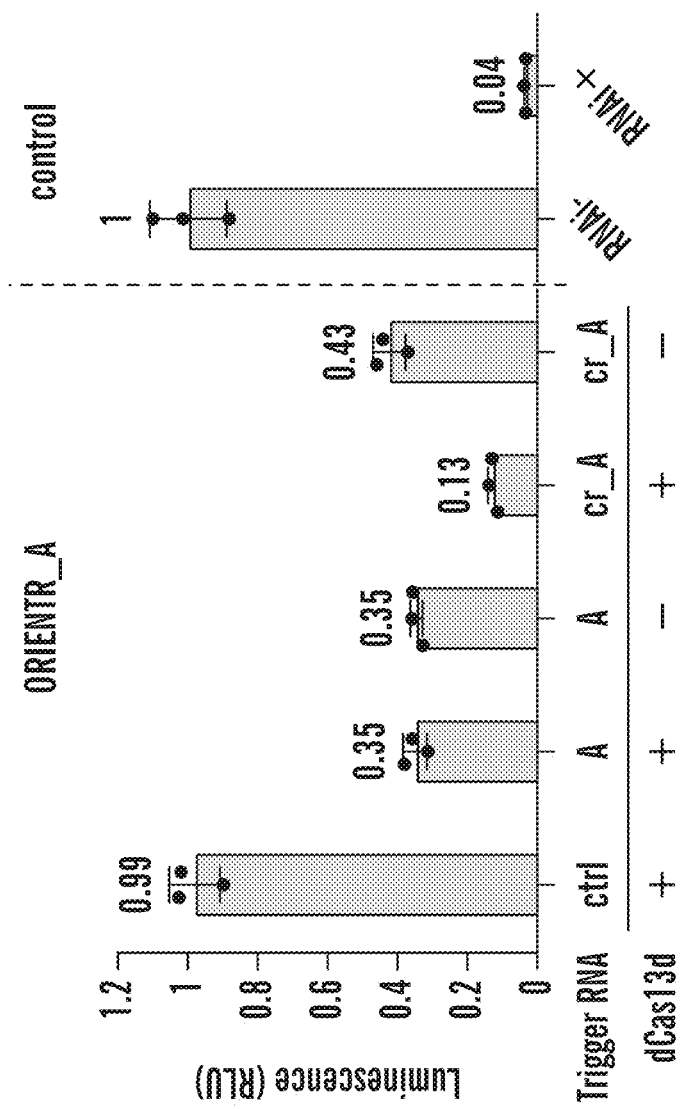
FIG. 3D shows results from a RNAi assay with luciferase reporter in cells for ORIENTR_A with the original trigger or a cr-trigger with or without dCas13d. n=3 biological replicates, bars represent the mean+s.d.

To improve the performance of the trigger RNA, the inventors replaced 5' protecting hairpin in RNA-triggers A and B with the CRISPR RNA (ORIENTR) scaffold hairpin used by rfxCas13d[34] to form new chimeric triggers cr-A and cr-B (see Table 8 for sequences) that can be bound by deactivated rfxCas13d (dCas13d) (FIG. 3B). The RNA-dCas13d complex formed between these chimeric CRISPR triggers (cr-triggers) and dCas13d mimics the natural RNA/RBP (RNA-binding protein) interactions in mammalian cells to protect the small trigger RNAs from degradation. Moreover, the use of a nuclear localization signal peptide on dCas13d can help transport the trigger RNA back into the nucleus. It was discovered that the chimeric RNA-triggers alone were less effective at generating miRNAs than the original triggers (compare lane 5 to lane 3 for ORIENTR_A and B in FIG. 3C), possibly because the ORIENTR scaffold hairpin is less stable than the original 5' hairpin at protecting the RNA from degradation. However, in the presence of dCas13d (lane 4 in FIG. 3A), the cr-trigger RNAs significantly promoted miRNA production, each giving 31.7-fold and 15.4-fold increases in miRNA levels compared with the non-cognate trigger RNA and significantly higher than the 14.7-fold and 8.8-fold increases observed for the original trigger RNAs without dCas13d present. The RNAi efficiency of ORIENTR_A was also quantitatively measured with a luciferase reporter (FIG. 3D). It was demonstrated that there is minimal miRNA biogenesis from ORIENTR alone with the luciferase activity retained at 99%. The cr-trigger significantly induced RNAi, decreasing luciferase activity to 13%, corresponding to a 7.7-fold reduction in gene expression. The improvement of cr-trigger/dCas13d compared with the original trigger (35% luciferase activity) demonstrates that RNA localization and stability have significant impact on ORIENTR performance in mammalian cells. Importantly, the inventors determined that incorporating protein components to facilitate programmed RNA interactions is useful and that protein-mediated RNA stabilization and localization can be used as a general strategy for enhancing RNA switch performance in mammalian cells.

TABLE 8 trigger sequence with Cas13d ORIENTR scaffold

| Plasmid ID | Plasmid Name | Sequence | SEQ ID NO: |
|---|---|---|---|
| ZY-248 | cr_trigA | ggaaacccctaccaactggtcggggtttgaaacAGCAATACAA TCTTACCTATCAATCACATCCATCTCATTTTTTT | 76 |
| ZY-250 | cr_trigB | ggaaacccctaccaactggtcggggtttgaaacAACTACACCG TGCCTGATTAGCGAAATAACATAATGATTTTTTT | 77 |

Example 5

By systematically examining the sequence and structural requirements for functional pri-miRNAs, the inventors have developed and successfully implemented RNA switches that provide conditional pri-miRNA activity. The ORIENTR molecules disclosed herein employ cis-repressing RNA secondary structures to prevent miRNA biogenesis, while interactions with cognate RNA triggers stimulate miRNA biogenesis and activate RNAi against a desired target gene. To do this, ORIENTRs encode within a single RNA molecule a sensing domain, a reconfiguration domain, and an output domain that all fold faithfully into a prescribed structure in the complex cellular environment (FIG. 1C). These domains also undergo substantial structural rearrangements upon binding to the RNA trigger to enable recognition by Drosha. Use of sensing and output domains that are not correlated in sequence provides ORIENTRs the capacity to direct a tissue-specific signature RNA to a targeted RNA interference response. Using de novo RNA sequence design, the inventors demonstrated six exemplary orthogonal ORIENTR/trigger pairs, and demonstrated that (i) signal leakage from ORIENTRs can be tuned through modification to RNA structure, and also (ii) that regulation dynamics can be improved by transporting the trigger RNA back to the nucleus with dCas13d (FIGS. 2 and 3). Thus the inventors have demonstrated the use of programmable cellular RNAs to regulate RNA interference in living cells, which is an important advance toward introducing synthetic regulatory links into mammalian cells and organisms. ORIENTRs, for instance, could be applied to programming and rewiring cell behavior in response to RNA expression profiles for diagnostic or therapeutic purposes.

It is envisioned that ORIENTRs could have important applications for the precise control of RNAi activity. By ensuring that RNAi is only activated when desired, ORIENTRs can help avoid over-burdening the endogenous miRNA biogenesis machinery[35] and thus minimize their impact on host cell function. Furthermore, ORIENTRs are compatible with tissue specific promoters enabling enhanced tissue-targeting precision[36], particularly when coupled with tissue-specific triggers for added regulatory control. ORIENTRs can be delivered to mammalian cells, e.g., in vivo or in vitro via gene vectors, including but not limited to viral vectors. As an exemplary example, ORIENTRs can be delivered via AAV delivery for long-term efficacy and penetration into otherwise challenging tissue targets like the central nervous system[37,38]. It is envisioned that ORIENTRs can be used for next-generation selective and safe RNA mediated gene therapy, including but not limited to AAV mediated RNAi gene therapy[39]. The ORIENTRs disclosed herein can be further refined by a person of ordinary skill in the art, e.g., for example, to decrease signal leakage and/or enhance the strength of RNAi produced when activated (e.g.m in the presence of a RNA-trigger molecule). Such improvements are envisioned by a person of ordinary skill in the art and are encompassed in the present invention, and can be used to maximize the range of triggers and target genes to which ORIENTRs can be applied. Lastly, the inventors have demonstrated herein the use of de novo design of RNAs for conditional RNAi, demonstrating that natural mechanisms for RNAi regulation can be optimized by modulation of pri-miRNA secondary structure.

REFERENCES

The references cited in the specification and Examples are incorporated herein in their entirety by reference.
1. Setten, R. L., Rossi, J. J. & Han, S. The current state and future directions of RNAi-based therapeutics. Nature Reviews Drug Discovery 2019 18:6 18, 421-446 (2019).
2. Tatiparti, K., Sau, S., Kashaw, S. K. & Iyer, A. K. siRNA Delivery Strategies: A Comprehensive Review of Recent Developments. Nanomaterials 7, 77 (2017).
3. Fu, Y., Chen, J. & Huang, Z. Recent progress in microRNA-based delivery systems for the treatment of human disease. ExRNA 1, 1-14 (2019).
4. Grimm, D. The dose can make the poison: lessons learned from adverse in vivo toxicities caused by RNAi overexpression. Silence 2, 1-6 (2011).
5. Borel, F., Kay, M. A. & Mueller, C. Recombinant AAV as a Platform for Translating the Therapeutic Potential of RNA Interference. Molecular Therapy 22, 692 (2014).
6. Wiznerowicz, M., Szulc, J. & Trono, D. Tuning silence: conditional systems for RNA interference. Nat Methods 3, 682-688 (2006).
7. Chandran, V. et al. Inducible and reversible phenotypes in a novel mouse model of Friedreich's Ataxia. Elife 6, e30054 (2017).
8. Mcjunkin, K. et al. Reversible suppression of an essential gene in adult mice using transgenic RNA interference. Proc Natl Acad Sci USA 108, 7113-7118 (2011).
9. An, C.-I., Trinh, V. B. & Yokobayashi, Y. Artificial control of gene expression in mammalian cells by modulating RNA interference through aptamer-small molecule interaction. RNA 12, 710-716 (2006).
10. Kumar, D., An, C.-I. & Yokobayashi, Y. Conditional RNA Interference Mediated by Allosteric Ribozyme. J Am Chem Soc 131, 13906-13907 (2009).
11. Beisel, C. L., Chen, Y. Y., Culler, S. J., Hoff, K. G. & Smolke, C. D. Design of small molecule-responsive microRNAs based on structural requirements for Drosha processing. Nucleic Acids Res 39, 2981-2994 (2011).
12. Kumar, D., Kim, S. H. & Yokobayashi, Y. Combinatorially Inducible RNA Interference Triggered by Chemically Modified Oligonucleotides. J Am Chem Soc 133, 2783-2788 (2011).
13. Hochrein, L. M., Schwarzkopf, M., Shahgholi, M., Yin, P. & Pierce, N. A. Conditional Dicer Substrate Formation via Shape and Sequence Transduction with Small Conditional RNAs. J Am Chem Soc 135, 17322-17330 (2013).
14. Hochrein, L. M., Ge, T. J., Schwarzkopf, M. & Pierce, N. A. Signal Transduction in Human Cell Lysate via Dynamic RNA Nanotechnology. ACS Synth Biol 7, 2796-2802 (2018).
15. Kim, J. et al. De novo-designed translation-repressing riboregulators for multi-input cellular logic. Nat Chem Biol 15, 1173-1182 (2019).
16. Yan, Z. et al. Rapid and Multiplexed Nucleic Acid Detection using Programmable Aptamer-Based RNA Switches. medRxiv preprint (2023) doi: 10.1101/2023.06.02.23290873.
17. Green, A. A., Silver, P. A., Collins, J. J. & Yin, P. Toehold Switches: De-Novo-Designed Regulators of Gene Expression. Cell 159, 925-939 (2014).
18. Griffiths-Jones, S., Grocock, R. J., Van Dongen, S., Bateman, A. & Enright, A. J. miRBase: microRNA sequences, targets and gene nomenclature. Nucleic Acids Res 34, D140-D144 (2006).
19. Qian, Y. et al. Programmable RNA sensing for cell monitoring and manipulation. Nature 610, 713 (2022).
20. Kaseniit, K. E. et al. Modular, programmable RNA sensing using ADAR editing in living cells. Nat Biotechnol 41, 482-487 (2022).
21. Jiang, K. et al. Programmable eukaryotic protein synthesis with RNA sensors by harnessing ADAR. Nat Biotechnol 41, 698-707 (2022).
22. Oesinghaus, L. & Simmel. F. Controlling Gene Expression in Mammalian Cells Using Multiplexed Conditional Guide RNAs for Cas12a**. Angew. Chem. Int. Ed 60, 23894-23902 (2021).
23. Treiber, T., Treiber, N. & Meister, G. Regulation of microRNA biogenesis and its crosstalk with other cellular pathways. Nat Rev Mol Cell Biol 20, 5-20 (2019).
24. Ha, M. & Kim, V. N. Regulation of microRNA biogenesis. Nature Reviews Molecular Cell Biology vol. 15 509-524 Preprint at https://doi.org/10.1038/nrm3838 (2014).
25. Jin, W., Wang, J., Liu, C. P., Wang, H. W. & Xu, R. M. Structural Basis for pri-miRNA Recognition by Drosha. Mol Cell 78, 423-433.e5 (2020).

26. MacRae, I. J. et al. Structural basis for double-stranded RNA processing by Dicer. Science (1979) 311, 195-198 (2006).
27. MacRae, I. J., Zhou, K. & Doudna, J. A. Structural determinants of RNA recognition and cleavage by Dicer. Nat Struct Mol Biol 14, 934-940 (2007).
28. Nguyen, T. A. et al. Functional Anatomy of the Human Microprocessor. Cell 161, 1374-1387 (2015).
29. Kim, K. et al. A quantitative map of human primary microRNA processing sites. Mol Cell 81, 3422-3439 (2021).
30. Xie, M. et al. The host Integrator complex acts in transcription-independent maturation of herpesvirus microRNA 3' ends. Genes Dev 29, 1552-1564 (2015).
31. Green, A., Ma, D. & Tang, A. Unimolecular aptamer-based sensors for pathogen detection. US Patent Application. PCT/US2017/056960 (2017).
32. Zadeh, J. N. et al. NUPACK: Analysis and design of nucleic acid systems. J Comput Chem 32, 170-173 (2011).
33. Zhang, Q. et al. Predictable control of RNA lifetime using engineered degradation-tuning RNAs. Nat Chem Biol 17, 828-836 (2021).
34. Yan, W. X. et al. Cas13d Is a Compact RNA-Targeting Type VI CRISPR Effector Positively Modulated by a WYL-Domain-Containing Accessory Protein. Mol Cell 70, 327-339.e5 (2018).
35. Grimm, D. et al. Fatality in mice due to oversaturation of cellular microRNA/short hairpin RNA pathways. Nature 441, 537-541 (2006).
36. Rao, M. K. & Wilkinson, M. F. Tissue-specific and cell type-specific RNA interference in vivo. Nat Protoc 1, 1494-1501 (2006).
37. Hocquemiller, M., Giersch, L., Audrain, M., Parker, S. & Cartier, N. Adeno-Associated Virus-Based Gene Therapy for CNS Diseases. Hum Gene Ther 27, 478 (2016).
38. Wang, W. et al. Efficient and Precise Processing of the Optimized Primary Artificial MicroRNA in a Huntingtin-Lowering Adeno-Associated Viral Gene Therapy in Vitro and in Mice and Nonhuman Primates. Hum Gene Ther 33, 37-60 (2022).
39. Harper, S. Q. Progress and Challenges in RNA Interference Therapy for Huntington Disease. Arch Neurol 66, 933-938 (2009).
40. Hennig. T. et al. Selective inhibition of miRNA processing by a herpesvirus-encoded miRNA. Nature 605, 539-544 (2022).
41. Miller, B. R., Wei, T., Fields, C. J., Sheng, P. & Xie, M. Near-infrared fluorescent northern blot. RNA 24, 1871-1877 (2018).
42. Gruber, A. R., Lorenz, R., Bernhart, S. H., Ck, R. N. & Hofacker, I. L. The Vienna RNA Websuite. Nucleic Acids Res 36, w70-w74 (2008).
Beisel at al., Nucleic Acids Research, 2011; 39 (7); 2981-2994;
U.S. Pat. No. 11,802,318,
U.S. Pat. No. 9,518,263,
U.S. Pat. No. 9,550,987,
U.S. Pat. No. 10,550,440,
International Patent Application: WO2021/062096,
US Patent Application US2006/0178327

Example 2

ORIENTR Design and Performance

Based on the above results, the inventors devised a design for ORIENTRs that built upon earlier work on aptamer-based RNA switches used for in vitro diagnostics[16,31]. In the present ORIENTR design, the 11-nt sequence in 5' half of the basal stem was sequestered in a hairpin structure to

The invention claimed is:

1. A nucleic acid construct comprising an Orthogonal RNA Interference induced by Trigger RNA (ORIENTR) molecule, the ORIENTR molecule having a secondary structure in the absence of a RNA trigger sequence as follows, in a 5' to 3' order:
   a) a single-stranded 5' toehold domain (T1),
   b) a fully or partially double-stranded RNA sequestering-Loop domain (SLD) comprising:
      i) a 3' sequestering arm region comprising a 5' region (S1) and a 3' region (S2),
      ii) a stem-loop comprising at least 5 nucleotides,
      iii) a 3' flanking sequence (S2f), wherein 3' flanking sequence forms a RNA duplex with 3' region (S2) of the sequestering arm region,
      iv) a 5' basal stem (5'-BS) sequence, wherein 5' basal stem sequence forms a RNA duplex with a 5' region (S1) of the sequestering arm,
   c) an output domain, the output domain comprising a fully or partially double-stranded RNAi hairpin, comprising:
      i) a guide strand sequence targeting a nucleic acid of interest,
      ii) a loop sequence, and
      iii) a passenger strand sequence to the guide strand sequence, where the passenger strand forms a partially or full double-stranded stem with the guide strand sequence;
   d) a 3' basal stem (3' BS) sequence, wherein 3' basal stem sequence is capable of complementary base pairing with 5' basal stem sequence to form a basal stem structure that is recognized and can be bound by Drosha; and
   e) a spacer sequence located 3' of the basal stem sequence, wherein the spacer sequence comprises a small hairpin sequence (SHS) that is capable of forming a partial or full RNA-duplex with a 3' portion of 3' basal stem sequence to form a leak-reduction motif, and wherein the spacer sequence further comprises a CNNC motif.

2. The nucleic acid construct of claim 1, wherein the RNAi hairpin in the output domain is a pri-miRNA hairpin structure, and wherein the loop sequence in the output domain is an apical loop.

3. The nucleic acid construct of claim 1, wherein the ORIENTR further comprises a RNA Pol III terminator sequence located 3' of 3' basal stem sequence or 3' of the spacer sequence.

4. The nucleic acid construct of claim 1, wherein 3' basal stem sequence is a single stranded RNA.

5. The nucleic acid construct of claim 1, wherein the SHS is at least 5 bp in length, and can partially base pair with at least 5 bp of 3' basal stem sequence.

6. The nucleic acid construct of claim 1, wherein in the presence of a RNA trigger sequence, the ORIENTR molecule forms a complex with a RNA trigger sequence, and reconfigures to comprise a secondary structure having, in a 5' to 3' order:
   a) a RNA duplex comprising 5' toehold domain (T1) and S1 and S2 regions of 3' sequestering arm duplexed with of a RNA-trigger sequence, wherein the RNAtrigger comprises a T1* region, a S1* region and a S2* region, and wherein the T1*, S1* and S2* regions base pair with the T1, S1 and S2 regions respectively, of 3' sequestering arm sequence of the ORIENTR molecule;
   b) a single-stranded 3' flanking sequence (S2$^f$), and
   c) a pri-miRNA scaffold comprising a fully or partially double-stranded RNA duplex comprising, in a 5' to 3' order:
      i) 5' basal stem (5'-BS) sequence,
      ii) the output domain, the output domain comprising a fully or partially double-stranded RNAi hairpin, comprising the guide strand sequence targeting a nucleic acid of interest, the loop sequence, and the passenger strand sequence, and
      iii) 3' basal stem (3'-BS) sequence, wherein 5' basal stem sequence and 3' basal stem sequence exist in a RNA-duplex that serves as a basal stem structure that can be recognized and bound by Drosha.

7. The nucleic acid construct of claim 6, wherein 5' basal stem sequence is at least 11 nucleotides, and 3' basal stem sequence is at least 11 nucleotides and can form an imperfect basal stem structure that can be recognized by Drosha.

8. The nucleic acid construct of claim 6, wherein the RNA trigger further comprises a stability hairpin at the 5' end.

9. The nucleic acid construct of claim 6, wherein the T1*, S1* and S2* regions of the RNA trigger sequence comprise a RNA nucleotide sequence between 9-50 nucleotides.

10. The nucleic acid construct of claim 8, wherein the stability hairpin is a CRISPR RNA (crRNA) hairpin or a rfxCas13d scaffold hairpin, or can be bound by dCas13d.

11. The nucleic acid construct of claim 6, wherein any one or more of: 5' toehold domain (T1), S1 region, S2 region, and 3' sequestering arm of the ORIENTR is a synthetic sequence and the RNA sequence of a RNA-trigger sequence is a synthetic RNA sequence.

12. The nucleic acid construct of claim 6, wherein any one or more of: 5' toehold domain (T1), S1 region, S2 region, and 3' sequestering arm can form a double-stranded duplex with the RNA sequence of the RNA-trigger sequence, wherein the RNA sequence is selected from any of: a tissue specific RNA sequence, a disease specific RNA sequence, an environmental RNA sequence, a developmental RNA sequence, a temporal RNA sequence, or a cell-cycle specific sequence.

13. A system comprising:
   d) the nucleic acid construct comprising the ORIENTR of claim 1, and
   e) a RNA-trigger sequence.

14. The system of claim 13, wherein the RNA trigger comprises a T1* region, a S1* region and a S2* region, wherein the T1* region can base pair with the toehold region T1 of the ORIENTR molecule, the S1* can base pair with the S1 region of 3' sequestering arm sequence of the ORIENTR molecule, and the S2* can base pair with the S2* region of 3' sequestering arm sequence of the ORIENTR molecule.

15. The system of claim 13, wherein the RNA trigger further comprises a stability hairpin at the 5' end.

16. The system of claim 13, wherein the T1*, S1* and S2* regions of the RNA trigger comprise a RNA sequence between 9-50 nucleotides, and wherein the RNA sequence is a synthetic RNA sequence.

17. The system of claim 15, wherein the stability hairpin is a CRISPR RNA (crRNA) hairpin or a rfxCas13d scaffold hairpin, or a hairpin that can be bound by dCas13d.

18. The system of claim 16, wherein any one of: 5' toehold domain (T1), the S1, the S2 region and 3' sequestering arm sequence is a synthetic sequence, and wherein the RNA sequence of the RNA-trigger sequence is a synthetic sequence.

19. The system of claim 13, wherein the T1*, S1*, and S2* regions of the RNA trigger comprise a RNA sequence between 9-50 nucleotides, and wherein the RNA sequence of the RNA trigger is selected from the group consisting of: a tissue specific RNA sequence, a disease specific RNA sequence, an environmental RNA sequence, a developmental RNA sequence, a temporal RNA sequence, and a cell-cycle specific sequence.

20. A vector comprising a first promoter operatively linked to a nucleic acid sequence encoding the nucleic acid construct of claim 1.

21. The nucleic acid construct of claim 20, wherein the vector further comprises a nucleic acid encoding a RNA trigger sequence, wherein the nucleic acid encoding the RNA trigger sequence is operatively linked to the first promoter, or a second promoter.

22. The nucleic acid construct of claim 21, wherein the RNA trigger comprises a T1* region, a S1* region and a S2* region, wherein the T1* region can base pair with the toehold region T1 of the ORIENTR molecule, the S1* can base pair with the S1 region of 3' sequestering arm sequence of the ORIENTR molecule, and the S2* can base pair with the S2* region of the 3' sequestering arm sequence of the ORIENTR molecule.

23. The nucleic acid construct of claim 21, wherein the first promoter or second promoter, or both, is selected from any of: a constitutive promoter, a tissue specific promoter, inducible promoter, cell cycle dependent promoter, cell stress dependent promoter, inflammation inducible promoter, hypoxia induced promoter.

24. The nucleic acid construct of claim 20, wherein the vector is a viral vector.

25. A cell comprising the nucleic acid molecule of claim 1, wherein the cell is a living mammalian cell or a living human cell.

26. The cell of claim 25, wherein the cell is present in a human subject in need of a treatment, or a cell is an ex vivo cell for delivery to a subject.

* * * * *